(12) United States Patent
Blagg et al.

(10) Patent No.: US 9,422,320 B2
(45) Date of Patent: Aug. 23, 2016

(54) C-TERMINAL HSP90 INHIBITORS

(71) Applicant: University of Kansas, Lawrence, KS (US)

(72) Inventors: Brian S. J. Blagg, Lawerence, KS (US); Bhaskar Reddy Kusuma, Lawrence, KS (US); Teather Sundstrom, Canton, MO (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 0 days.

(21) Appl. No.: 14/377,616

(22) PCT Filed: Feb. 8, 2013

(86) PCT No.: PCT/US2013/025387
§ 371 (c)(1),
(2) Date: Aug. 8, 2014

(87) PCT Pub. No.: WO2013/119985
PCT Pub. Date: Aug. 15, 2013

(65) Prior Publication Data
US 2015/0057240 A1 Feb. 26, 2015

Related U.S. Application Data

(60) Provisional application No. 61/597,004, filed on Feb. 9, 2012.

(51) Int. Cl.
C07C 211/17 (2006.01)
C07H 15/203 (2006.01)

(52) U.S. Cl.
CPC ............ *C07H 15/203* (2013.01); *C07C 211/17* (2013.01)

(58) Field of Classification Search
None
See application file for complete search history.

(56) References Cited

U.S. PATENT DOCUMENTS

| | | | |
|---|---|---|---|
| 7,608,594 B2 | 10/2009 | Blagg et al. | |
| 7,622,451 B2 | 11/2009 | Blagg et al. | |
| 7,811,998 B2 | 10/2010 | Blagg et al. | |
| 7,960,353 B2 | 6/2011 | Blagg | |
| 8,212,011 B2 | 7/2012 | Blagg | |
| 8,212,012 B2 | 7/2012 | Blagg | |
| 2006/0199776 A1 | 9/2006 | Blagg et al. | |
| 2007/0270452 A1 | 11/2007 | Blagg et al. | |
| 2008/0146547 A1 | 6/2008 | Araldi et al. | |
| 2009/0163709 A1 | 6/2009 | Blagg | |
| 2009/0187014 A1 | 7/2009 | Blagg | |
| 2010/0048882 A1 | 2/2010 | Blagg et al. | |
| 2010/0105630 A1 | 4/2010 | Blagg | |
| 2011/0082098 A1 | 4/2011 | Calvet et al. | |
| 2012/0252745 A1 | 10/2012 | Blagg et al. | |
| 2012/0309702 A1 | 12/2012 | Blagg et al. | |
| 2013/0116227 A1 | 5/2013 | Katayama et al. | |

FOREIGN PATENT DOCUMENTS

| | | |
|---|---|---|
| WO | WO 2006/050501 | 5/2006 |
| WO | WO 2010/096650 | 8/2010 |
| WO | WO 2011/041593 | 4/2011 |
| WO | WO 2012/162054 | 11/2012 |
| WO | WO 2015/200514 | 12/2015 |

OTHER PUBLICATIONS

Alzheimer's disease, PubMed Health, Nov. 17, 2010.*
Roos, Orphanet Journal of Rare Diseases 2010, 5:40.*
Parkinson's: Overview—PubMed Health, Apr. 8, 2015.*
Office Communication issued in corresponding European Application No. 13706822.7, dated Jun. 22, 2015.
Office Communication issued in corresponding Chinese Application No. 201380019057.X, dated Jul. 24, 2015. [English Translation].
Office Communication issued in corresponding Eurasian Application No. 201491496, dated Aug. 10, 2015. [English Translation].
Ansar et al., "A non-toxic HSp90 inhibitor protects neurons from Abeta-induced toxicity," *Bioorg Med Chem Lett*, 17(7):1984-90, 2007.
Avila et al., "High-throughput screening for Hsp90 ATPase inhibitors," *Bioorg Med. Chem. Lett.*, 16(11):3005-08, 2006.
Burlison and Blagg, "Synthesis and Evaluation of coumermycin A1 analogues that inhibit the Hsp90 protein folding machinery," *Org Lett.*, 8(21):4855-8, 2006.
Burlison et al., "Development of novobiocin analogues that manifest anti-proliferative activity against several cancer cell lines", *J Org Chem.*, 73 (6): 2130-7, 2008.
Burlison et al., "Novobiocin: redesigning a DNA gyrase inhibitor for selective inhibition of Hsp90", *Journal of the American Chemical Society*, 128 (48): 15529-15536, 2006.
Comer et al., "Characterization of a novel novobiocin analogue as a putative C-terminal inhibitor of heat shock protein 90 in prostate cancer cells," *Prostate*, 70(1):27-36, 2010.
Donnelly and Blagg, "Novobiocin and additional inhibitors of the Hsp90 C-terminal nucleotide-binding pocket," *Curr. Med. Chem.*, 15(26):2702-17, 2008.
Donnelly et al., "The Design, Synthesis, and Evaluation of Coumarin Ring Derivatives of the Novobiocin Scaffold that Exhibit Antiproliferative Activity", *J. Org. Chem.*, 73(22): 8901-8920, 2008.
Farmer et al., "KU-32, a novel drug for diabetic neuropathy, is safe for human islets and improves in vitro insulin secretion and viability," *Experimental Diabetes Research*, 671-673, 2012.
Hadden et al., "Synthesis and evaluation of Hsp90 inhibitors that contain the 1,4-naphthoquinone scaffold," *Bioorg Med Chem.*, 17(2):634-40, 2009.
Huang and Blagg, "A library of noviosylated coumarin analogues," *J. Org. Chem.*, 72(10):3609-3613, 2007.
International Preliminary Report on Patentability issued in International Application No. PCT/US2013/025387, issued Aug. 12, 2014.
International Search Report and Written Opinion issued in International Application No. PCT/US2013/025387, mailed Apr. 2, 2013.
Kusuma et al., "Synthesis and Evaluation of Novologues as C-Terminal Hsp90 Inhibitors with Cytoprotective Activity against Sensory Neuron Glucotoxicity," *J. Med. Chem.*, 55(12):5797-5812, 2012.
Kusuma et al., "Targeting the Heat Shock Protein 90 Dimer with Dimeric Inhibitors", *Journal of Medicinal Chemistry*, 54(18):6234-6253, 2011.

(Continued)

*Primary Examiner* — Layla Berry

(74) *Attorney, Agent, or Firm* — Parker Highlander PLLC

(57) ABSTRACT

Hsp90 C-terminal inhibitors and pharmaceutical compositions containing such compounds are provided. The compounds of the disclosure are useful for the treatment and/or prevention of neurodegenerative disorders such as diabetic peripheral neuropathy.

19 Claims, 5 Drawing Sheets

(56) References Cited

OTHER PUBLICATIONS

Lu et al., "Neuroprotective activity and evaluation of Hsp90 inhibitors in an immortalized neuronal cell line," *Bioorg. Med. Chem.*, 17(4):1709-15, 2009.

Matts et al., "Elucidation of the Hsp90 C-Terminal Inhibitor Binding Site", *ACS Chem Biol.*, 6(8):800-807, 2011.

Mayer et al., "Hsp70 chaperones: cellular functions and molecular mechanism", *Cell Mol Life Sci.*, 62 (6): 670-84, 2005.

Mays et al., "The synthesis and evaluation of flavone and isoflavone chimeras of novobiocin and derrubone," *Bioorg Med. Chem.*, 18(1):249-66, 2010.

Peterson and Blagg, "Click chemistry to probe Hsp90: synthesis and evaluation of a series of triazole-containing novobiocin analogues," *Bioorg Med Chem Lett*, 20(13):3957-60, 2010.

Peterson and Blagg, "To fold or not to fold: modulation and consequences of Hsp90 inhibition" *Future Med Chem.*, 1 (2): 267-283, 2009.

Shelton et al., "KU135, a novel novobiocin-derived C-terminal inhibitor of the 90-kDa heat shock protein, exerts potent antiproliferative effects in human leukemia cells," *Mol. Pharmacol.*, 76(6):1314-22, 2009.

Shen et al., "Synthesis of photolabile novobiocin analogues," *Bioorg Med Chem Lett.*, 14(23):5903-6, 2004.

Urban et al., "Inhibiting Heat Shock Protein 90 Reverses Sensory Hypoalgesia in Diabetic Mice", *ASN Neuro.*, 2(4): 189-199, 2010.

Urban et al., "Modulating Molecular Chaperones Improves Sensory Fiber Recovery and Mitochondrial Function in Diabetic Peripheral Neuropathy," *Experimental Neurology*, 235(1):388-396, 2012.

Vincent et al., "Cell culture modeling to test therapies against hyperglycemia-mediated oxidative stress and injury", *Antioxid Redox Signal*, 7:(11-12):1494-506, 2005.

Vincent et al., "Sensory Neurons and Schwann Cells Respond to Oxidative Stress by Increasing Antioxidant Defense Mechanisms", *Antioxid Redox Signal*, 11:425-438, 2009.

Yu et al., "Hyperglycemia and downregulation of caveolin-1 enhance neuregulin-induced demyelination", *Glia*, 56: 877-887, 2008.

Yu, et al., "Hsp90 inhibitors identified from a library of novobiocin analgoues," *J. Am. Chem. Soc.*, 127(37):12778-79, 2005.

Zhang et al, "Hyperglycemia alters the schwann cell mitochondrial proteome and decreases coupled respiration in the absence of superoxide production", *J Proteome Res.*, 9(1):458-71, 2010.

Zhang, et al., "C-Terminal Heat Shock Protein 90 Inhibitor Decreases Hyperglycemia-induced Oxidative Stress and Improves Mitochondrial Bioenergetics in Sensory Neurons," *J. Proteome Research*, 11(4):2581-2593, 2012.

Zhao et al., "3D-QSAR-assisted design, synthesis and evaluation of novobiocin analogues", *ACS Med Chem Lett.*, 4(1): 57-62, 2013.

Zhao et al., "Engineering an antibiotic to fight cancer: optimization of the novobiocin scaffold to produce anti-proliferative agents," *J. Med. Chem.*, 54(11):3839-53, 2011.

Zhao et al., "Synthesis and Evaluation of Noviose Replacements on Novobiocin that Manifest Anti-proliferative activity," *ACS Med Chem Lett.*, 1(7):311-315, 2010.

Anyika et al., "Development of Noviomimetics as C-Terminal Hsp90 Inhibitors", *ACS Medicinal Chemistry Letters*, 7: 67-71, 2016.

* cited by examiner

C-TERMINAL HSP90 INHIBITORS

RELATED APPLICATIONS

This application is a National Stage Application of PCT/US2013/025387, filed Feb. 9, 2013, which claims the benefit of U.S. Provisional Ser. No. 61/597,004, filed Feb. 9, 2012. The foregoing applications are incorporated herein by reference.

STATEMENT REGARDING FEDERALLY SPONSORED RESEARCH OR DEVELOPMENT

This invention was made with government support under Grant Nos. CA120458, CA109265, NS054847 and DK073594, awarded by the National Institutes of Health. The government has certain rights in the invention.

FIELD OF THE INVENTION

The present invention is directed to novel C-terminal heat shock protein 90 (Hsp 90) inhibitors with cytoprotective activity against sensory neuron glucotoxicity.

DESCRIPTION OF RELATED ART

Approximately 26 million Americans are afflicted with either Type 1 or Type 2 diabetes. Despite the use of insulin and oral anti-diabetic medications to help maintain euglycemia, about 60-70% of these individuals develop diabetic peripheral neuropathy (DPN). Veves, A.; Backonja, M.; Malik, R. A., Painful diabetic neuropathy: Epidemiology, natural history, early diagnosis, and treatment options. *Pain Med.* 2008, 9, 660-674.

To date, approaches toward the treatment of DPN have centered on pathways/targets directly limited to hyperglycemia (i.e., polyol & hexosamine pathways, advanced glycation end products (AGEs), enhanced oxidative stress, PKC activation). Tomlinson, D. R.; Gardiner, N. J., Glucose neurotoxicity. *Nat Rev Neurosci* 2008, 9 (1), 36-45.

Unfortunately, the contribution of these targets/pathways to the progression of DPN differs between individuals and does not occur with biochemical uniformity, and consequently, these approaches have resulted in little success for the management of DPN. As an alternative approach, we have explored the pharmacologic modulation of molecular chaperones to promote a broad cytoprotective response that may enhance a patient's ability to tolerate hyperglycemic insults and improve the symptoms of DPN.

Molecular chaperones, such as heat shock proteins 90 and 70 (Hsp90, Hsp70), are essential for folding nascent polypeptides into their biologically active structures and for the refolding of aggregated and denatured proteins that occur upon cellular stress. Mayer, M. P.; Bukau, B., Hsp70 chaperones: cellular functions and molecular mechanism. *Cell Mol Life Sci* 2005, 62 (6), 670-84; Peterson, L. B.; Blagg, B. S., To fold or not to fold: modulation and consequences of Hsp90 inhibition. *Future Med Chem* 2009, 1 (2), 267-283.

Numerous conditions that cause cell stress can also induce the "heat shock response" (HSR); the transcriptional upregulation of antioxidant genes and chaperones such as Hsp70. Importantly, small molecule inhibition of Hsp90 is sufficient to induce the HSR. KU-32 (FIG. 1) is a small molecule Hsp90 C-terminal inhibitor that is based on novobiocin, a naturally occurring antimicrobial agent that inhibits DNA gyrase. KU-32 is disclosed in U.S. Pat. No. 7,622,451 to Blagg et al. and U.S. Pat. No. 7,960,353 to Blagg. Although the etiology of DPN is unrelated to the accumulation of one specific misfolded or aggregated protein, hyperglycemia can increase oxidative stress and the oxidative modification of amino acids (Obrosova, I. G., Diabetes and the peripheral nerve. *Biochim Biophys Acta* 2009, 10, 931-940; Akude, E.; Zherebitskaya, E.; Roy Chowdhury, S. K.; Girling, K.; Fernyhough, P., 4-Hydroxy-2-Nonenal Induces Mitochondrial Dysfunction and Aberrant Axonal Outgrowth in Adult Sensory Neurons that Mimics Features of Diabetic Neuropathy. *Neurotox Res* 2009, 1, 28-38) that impair protein folding, (Muchowski, P. J.; Wacker, J. L., Modulation of neurodegeneration by molecular chaperones. *Nat Rev Neurosci* 2005, 6 (1), 11-22) decrease mitochondrial protein import (Baseler, W. A.; Dabkowski, E. R.; Williamson, C. L.; Croston, T. L.; Thapa, D.; Powell, M. J.; Razunguzwa, T. T.; Hollander, J. M., Proteomic alterations of distinct mitochondrial subpopulations in the type 1 diabetic heart: contribution of protein import dysfunction. *Am J Physiol Regul Integr Comp Physiol* 2011, 300 (2), R186-200) and promote mitochondrial dysfunction. Tomlinson et al., 2008 Id.; Obrosova et al., 2009 Id.

Even in the absence of a single, disease-specific protein aggregate, it has been shown that pharmacologic induction of cytoprotective molecular chaperones can improve myelinated and unmyelinated fiber function in cellular models of glucotoxic stress and animal models of DPN. Urban, M. J.; Li, C.; Yu, C.; Lu, Y.; Krise, J. M.; McIntosh, M. P.; Rajewski, R. A.; Blagg, B. S. J.; Dobrowsky, R. T., Inhibiting Heat Shock Protein 90 Reverses Sensory Hypoalgesia in Diabetic Mice. *ASN Neuro* 2010, 2, e00040 DOI:189-199.

Mechanistically, KU-32 was ineffective at preventing neuregulin-induced demyelination of myelinated cultures of sensory neurons prepared from Hsp70.1 and 70.3 double knockout mice, indicating that Hsp70 is necessary for the neuroprotective activity manifested by KU-32. Similarly, weekly treatment with KU-32 restored normal sensory and motor nerve function in diabetic wild type mice, but was unable to reverse multiple clinical indices of DPN in the diabetic Hsp70 knockout mice. Urban et al., 2010 Id. Collectively, these studies provide the biological and clinical rationale to support the modulation of molecular chaperones as a viable approach toward the treatment of DPN.

An enviable aspect of KU-32 is that it induces Hsp70 at concentrations well below those needed to inhibit Hsp90's protein folding ability. Urban et al., 2010 Id. Thus, KU-32 possesses a rather broad therapeutic window that dissociates cytoprotective properties from potentially cytotoxic effects resulting from the degradation of Hsp90-dependent client proteins. Peterson et al., 2009 Id. This lab previously demonstrated that molecules containing a benzamide, as found in novobiocin, exhibit anti-proliferative activities, whereas molecules containing an acetamide (e.g., KU-32) manifest neuroprotective properties. However, these prior studies sought to evaluate structure-activity relationships for novobiocin analogues as anti-cancer agents, (Burlison, J. A.; Avila, C.; Vielhauer, G.; Lubbers, D. J.; Holzbeierlein, J.; Blagg, B. S., Development of novobiocin analogues that manifest anti-proliferative activity against several cancer cell lines. *J Org Chem* 2008, 73 (6), 2130-7; Donnelly, A. C.; Mays, J. R.; Burlison, J. A.; Nelson, J. T.; Vielhauer, G.; Holzbeierlein, J.; Blagg, B. S. J., The Design, Synthesis, and Evaluation of Coumarin Ring Derivatives of the Novobiocin Scaffold that Exhibit Antiproliferative Activity. *J. Org. Chem.* 2008, 73 (22), 8901-8920) rather than exploring chemical attributes that enhance the neuroprotective properties of novobiocin-based analogs. Therefore, diversification of the KU-32 scaffold was explored to identify novel compounds which lack

BRIEF SUMMARY OF THE INVENTION the coumarin ring system yet surprisingly enhance the neuroprotective properties manifested by Hsp90 C-terminal inhibitors.

The present invention is directed to novel compounds useful as Hsp90 inhibitors, and in particular as neuroprotective agents. In particular, the present invention is directed to the therapeutic use of such compounds in the treatment and/or prevention of diabetic peripheral neuropathy or other neurodegenerative disorders in a subject in need thereof.

In one embodiment, the disclosure provides a compound or pharmaceutically acceptable salt according to Formula (I):

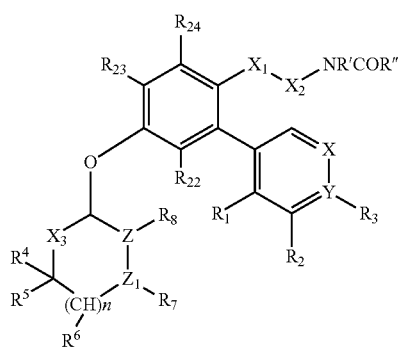

(I)

wherein $R_1$ is hydrogen, hydroxy, halo, trifluoroalkyl, alkyl, alkenyl, alkynyl, carbocyclic, heterocyclic, aryl, aralkyl, carboxyl, amido, amino, alkoxy, halo, trifluoromethyl, sulfanyl, sulfenyl, sulfonyl, or ether;

$R_2$ is hydrogen, halo, hydroxy, trifluoromethyl, alkoxy, alkyl, alkenyl, alkynyl, carbocyclic, alkylcarbocyclic, alkylheterocyclic, heterocyclic, or $-R^9-OR^{10}$, wherein $R^9$ is a covalent bond or alkyl, and $R^{10}$ is hydrogen, alkyl, C-amido or acyl; or $R_2$ together with $R_3$ and the atoms to which they are attached form a carbocyclic ring with 5 to 7 ring members or a heterocyclic ring having 4 to 8 ring members with at least one heteroatom selected from oxygen or nitrogen;

$R_3$ is hydrogen, hydroxy, halo, trifluoroalkyl, alkyl, alkoxy, sulfanyl, or $-R^{11}-O-R^{12}$, wherein $R^{11}$ is a covalent bond or alkyl, and $R^{12}$ is alkyl, C-amido or acyl; or $R_3$ together with $R_2$ and the atoms to which they are attached form a carbocyclic ring with 5 to 7 ring members or a heterocyclic ring having 4 to 8 ring members with at least one heteroatom selected from oxygen or nitrogen;

$R_4$ is hydrogen, hydroxy, alkyl, arylalkoxy, carboxyl, $-R^{13}-O-R^{14}$, or $-R^{13}-R^{15}$; and wherein $R^{13}$ is a covalent bond or alkyl, and $R^{14}$ is hydrogen, C-amido or acyl, and $R^{15}$ is N-amido, $-POR^{16}R^{17}-SO_2R^{18}$, or sulfonamido, and wherein $R^{16}$, $R^{17}$, $R^{18}$ are independently alkoxy;

$R_5$ is hydrogen, hydroxy, alkyl, arylalkoxy, alkenyl, alkynyl, aryl, or aralkyl;

$R_6$ is hydrogen, hydroxy, sulfanyl, alkyl, alkenyl, alkynyl, aryl, arylalkyl, alkoxy, aryloxy, arylalkoxy or a heterocyclic ring having 4 to 8 ring members with at least one heteroatom selected from oxygen or nitrogen;

$R_7$ is hydrogen, hydroxyl, arylalkoxy, alkyl, acyl, carboxyl or absent;

$R_8$ is hydrogen, hydroxyl, or arylalkoxy;

$R_{22}$ is hydrogen, hydroxy, amino, amido, cyano, alkoxy, halogen, trifluoroalkyl, alkyl, alkenyl, alkynyl, ester, nitro, carboxyl, aralkyl, aryl, carbocyclic, heterocyclic, trifluoromethyl, sulfonyl, sulfanyl, sulfenyl, ether, $R^{25}-OR^{26}$, or $R^{25}-NR^{26}$; where $R^{25}$ is a covalent bond or alkyl and $R^{26}$ is a hydrogen, alkyl, C-amido, or acyl;

$R_{23}$ is hydrogen, hydroxy, amino, amido, cyano, alkoxy, halogen, trifluoroalkyl, alkyl, alkenyl, alkynyl, ester, nitro, carboxyl, aralkyl, aryl, carbocyclic, heterocyclic, trifluoromethyl, sulfonyl, sulfanyl, sulfenyl, ether, $R^{27}-OR^{28}$, or $R^{27}-NR^{28}$; where $R^{27}$ is a covalent bond or alkyl and $R^{28}$ is a hydrogen, alkyl, C-amido, or acyl; or $R_{23}$ together with $R_{24}$ and the atoms to which they are attached form a carbocyclic ring with 5 to 7 ring members or a heterocyclic ring having 4 to 8 members with at least one heteroatom selected from oxygen or nitrogen;

$R_{24}$ is hydrogen, hydroxy, amino, amido, cyano, alkoxy, halogen, trifluoroalkyl, alkyl, alkenyl, alkynyl, ester, nitro, carboxyl, aralkyl, aryl, carbocyclic, heterocyclic, trifluoromethyl, sulfonyl, sulfanyl, sulfenyl, ether, $R^{29}-OR^{30}$, or $R^{29}-NR^{30}$, where $R^{29}$ is a covalent bond or alkyl and $R^{30}$ is a hydrogen, alkyl, C-amido, or acyl; or $R_{24}$ together with $R_{23}$ and the atoms to which they are attached form a carbocyclic ring with 5 to 7 ring members or a heterocyclic ring having 4 to 8 members with at least one heteroatom selected from oxygen or nitrogen;

$X_1$ is $-CHR^{19}-$, or $=CR^{19}-$, and wherein $R^{19}$ is selected from hydrogen, halo, alkyl, alkenyl, or alkynyl; or $X_1$ together with $X_2$ form a carbocyclic ring having 3 to 7 ring members; or wherein $X_1-X_2$ is $-C\equiv C-$;

$X_2$ is $-CHR^{20}-$, or $=CR^{20}-$, and wherein $R^{20}$ is selected from hydrogen, halo, alkyl, alkenyl, or alkynyl; or $X_2$ together with $X_1$ form a carbocyclic ring having 3 to 7 ring members; or wherein $X_1-X_2$ is $-C\equiv C-$;

$X_3$ is O, or $CH_2$;

X is $=CR^{21}-$, or $=N-$, wherein $R^{21}$ is hydrogen, halo, trifluoromethyl, alkyl, alkenyl, alkynyl, alkoxy, or hydroxy;

R' is H, or alkyl;

R" is alkyl, alkoxy, haloalkyl, alkylcycloalkyl or alkylamidoalkyl;

Y is $=CR_3-$ or $=N-$;

Z is CH, or $Z-Z_1$ is $-C\equiv C-$;

$Z_1$ is CH, O, S, N, or $Z-Z_1$ is $-C\equiv C-$; and n is 0, 1, 2, or 3.

In some embodiments, the disclosure provides a compound or salt according to Formula (I) wherein $X_1$ is $-CHR^{19}-$, and $R^{19}$ is hydrogen or alkyl; or $X_1$ together with $X_2$ form a carbocyclic ring having 3 to 7 ring members; and $X_2$ is $-CHR^{20}-$, and wherein $R^{20}$ is hydrogen or alkyl; or $X_2$ together with $X_1$ form a carbocyclic ring having 3 to 7 ring members.

In some embodiments, the disclosure provides a compound or salt according to Formula (I) wherein $X_1$ is $CH_2$, and $X_2$ is $CH_2$.

In some embodiments, the disclosure provides a compound or salt according to Formula (I) wherein R' is H and R" is $CH_3$.

In a further aspect, the disclosure provides a compound or salt according to Formula (I) wherein $R_4$ and $R_5$ are independently methyl or hydrogen.

In another aspect, the disclosure provides a compound or salt according to Formula (I) wherein $R_6$ is selected from hydrogen, hydroxy, methoxy, sulfanyl, or alkyl.

In another aspect, the disclosure provides a compound or salt according to Formula (I) wherein $R_7$ and $R_8$ are hydroxy.

In another aspect, the disclosure provides compounds of Formula (II):

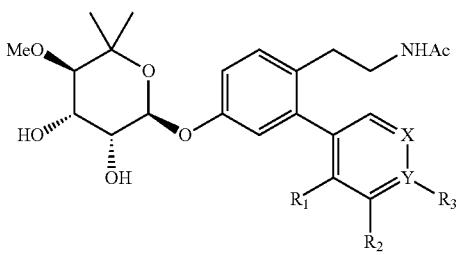

wherein

R₁ is hydrogen, halo, hydroxy, trifluoroalkyl, alkoxy, or sulfanyl;

R₂ is hydrogen, halo, hydroxy, trifluoroalkyl, alkoxy, sulfanyl, or alkyl, or R₂ together with R₃ and the atoms to which they are attached form a carbocyclic ring with 5 to 7 ring members or a heterocyclic ring having 4 to 8 ring members with at least one heteroatom selected from oxygen or nitrogen;

R₃ is hydrogen, halo, hydroxy, trifluoroalkyl, alkoxy, sulfanyl, alkyl; or R₃ together with R₂ and the atoms to which they are attached form a carbocyclic ring with 5 to 7 ring members or a heterocyclic ring having 4 to 8 ring members with at least one heteroatom selected from oxygen or nitrogen;

X is =CR²¹—, or =N—, wherein R²¹ is hydrogen, halo, or trifluoromethyl; and

Y is =CR₃— or =N—.

In another aspect, the disclosure provides a compound or salt according to Formula (II) wherein R₁ is hydrogen, halo, alkoxy, or sulfanyl; R₂ is hydrogen, hydroxy, halo, trifluoroalkyl, alkoxy, or sulfanyl; R₃ is hydrogen, hydroxy, halo, trifluoroalkyl, alkoxy, or sulfanyl; X is =CR²¹—, wherein R²¹ is hydrogen, halo, or trifluoromethyl; and Y is =CR₃—.

In specific aspects, the disclosure provides compounds useful for treating or preventing a neurodegenerative disorder selected from N-(2-(5-(((3R,4S,5R)-3,4-dihydroxy-5-methoxy-6,6-dimethyltetrahydro-2H-pyran-2-yl)oxy)-[1,1'-biphenyl]-2-yl)ethyl)acetamide (11a); N-(2-(5-(((3R,4S,5R)-3,4-dihydroxy-5-methoxy-6,6-dimethyltetrahydro-2H-pyran-2-yl)oxy)-3'-fluoro-[1,1'-biphenyl]-2-yl)ethyl)acetamide (11b); N-(2-(5-(((3R,4S,5R)-3,4-dihydroxy-5-methoxy-6,6-dimethyltetrahydro-2H-pyran-2-yl)oxy)-4'-fluoro-[1,1'-biphenyl]-2-yl)ethyl)acetamide (11c); N-(2-(2'-chloro-5-(((3R,4S,5R)-3,4-dihydroxy-5-methoxy-6,6-dimethyltetrahydro-2H-pyran-2-yl)oxy)-[1,1'-biphenyl]-2-yl)ethyl)acetamide (11d); N-(2-(3'-chloro-5-(((3R,4S,5R)-3,4-dihydroxy-5-methoxy-6,6-dimethyltetrahydro-2H-pyran-2-yl)oxy)-[1,1'-biphenyl]-2-yl)ethyl)acetamide (11e); N-(2-(5-(((3R,4S,5R)-3,4-dihydroxy-5-methoxy-6,6-dimethyltetrahydro-2H-pyran-2-yl)oxy)-3'-(trifluoromethyl)-[1,1'-biphenyl]-2-yl)ethyl)acetamide (11f); N-(2-(5-(((3R,4S,5R)-3,4-dihydroxy-5-methoxy-6,6-dimethyltetrahydro-2H-pyran-2-yl)oxy)-4'-(trifluoromethyl)-[1,1'-biphenyl]-2-yl)ethyl)acetamide (11g); N-(2-(5-(((3R,4S,5R)-3,4-dihydroxy-5-methoxy-6,6-dimethyltetrahydro-2H-pyran-2-yl)oxy)-2'-(methylthio)-[1,1'-biphenyl]-2-yl)ethyl)acetamide (11h); N-(2-(5-(((3R,4S,5R)-3,4-dihydroxy-5-methoxy-6,6-dimethyltetrahydro-2H-pyran-2-yl)oxy)-2'-methoxy-[1,1'-biphenyl]-2-yl)ethyl)acetamide (11i); N-(2-(5-(((3R,4S,5R)-3,4-dihydroxy-5-methoxy-6,6-dimethyltetrahydro-2H-pyran-2-yl)oxy)-3'-methoxy-[1,1'-biphenyl]-2-yl)ethyl)acetamide (11j); N-(2-(5-(((3R,4S,5R)-3,4-dihydroxy-5-methoxy-6,6-dimethyltetrahydro-2H-pyran-2-yl)oxy)-3'-methyl-[1,1'-biphenyl]-2-yl)ethyl)acetamide (11k); N-(2-(5-(((3R,4S,5R)-3,4-dihydroxy-5-methoxy-6,6-dimethyltetrahydro-2H-pyran-2-yl)oxy)-3'-(morpholinomethyl)-[1,1'-biphenyl]-2-yl)ethyl)acetamide (11l); N-(2-(5-(((3R,4S,5R)-3,4-dihydroxy-5-methoxy-6,6-dimethyltetrahydro-2H-pyran-2-yl)oxy)-4'-hydroxy-[1,1'-biphenyl]-2-yl)ethyl)acetamide (11m); N-(2-(5-(((3R,4S,5R)-3,4-dihydroxy-5-methoxy-6,6-dimethyltetrahydro-2H-pyran-2-yl)oxy)-4'-hydroxy-[1,1'-biphenyl]-2-yl)ethyl)acetamide (11m): N-(2-(benzo[d][1,3]dioxol-5-yl)-4-(((3R,4S,5R)-3,4-dihydroxy-5-methoxy-6,6-dimethyltetrahydro-2H-pyran-2-yl)oxy)phenethyl)acetamide (11n): N-(4-(((3R,4S,5R)-3,4-dihydroxy-5-methoxy-6,6-dimethyltetrahydro-2H-pyran-2-yl)oxy)-2-(pyridin-3-yl)phenethyl)acetamide (11o); N-(4-(((3R,4S,5R)-3,4-dihydroxy-5-methoxy-6,6-dimethyltetrahydro-2H-pyran-2-yl)oxy)-2-(pyridin-4-yl)phenethyl)acetamide (11p); N-(4'-(((3R,4S,5R)-3,4-dihydroxy-5-methoxy-6,6-dimethyltetrahydro-2H-pyran-2-yl)oxy)-3''-fluoro-1,2,3,6-tetrahydro-[1,1':2',1''-terphenyl]-2-yl)acetamide (20a); N-(4'-(((3R,4S,5R)-3,4-dihydroxy-5-methoxy-6,6-dimethyltetrahydro-2H-pyran-2-yl)oxy)-3''-(trifluoromethyl)-1,2,3,6-tetrahydro-[1,1':2',1''-terphenyl]-2-yl)acetamide (20b); N-(2-(5-((4-(benzyloxy)cyclohexyl)oxy)-3'-fluoro-[1,1'-biphenyl]-2-yl)ethyl)acetamide (24); N-(2-(5-((4-(benzyloxy)cyclohex-2-en-1-yl)oxy)-3'-fluoro-[1,1'-biphenyl]-2-yl)ethyl)acetamide (36); N-(2-(5-((4-(benzyloxy)-2,3-dihydroxycyclohexyl)oxy)-3'-fluoro-[1,1'-biphenyl]-2-yl)ethyl)acetamide (37); N-(2-(5-((4-(tert-butyl)cyclohexyl)oxy)-3'-fluoro-[1,1'-biphenyl]-2-yl)ethyl)acetamide (39); N-(2-(3'-fluoro-5-((4-(piperidin-4-yl)cyclohexyl)oxy)-[1,1'-biphenyl]-2-yl)ethyl)acetamide (40); N-(2-(5-(((3R,4S,5R)-3,4-dihydroxy-5-methoxy-6,6-dimethyltetrahydro-2H-pyran-2-yl)oxy)-3'-fluoro-6-hydroxy-[1,1'-biphenyl]-2-yl)ethyl)acetamide (41); N-(2-(5-(((3R,4S,5R)-3,4-dihydroxy-5-methoxy-6,6-dimethyltetrahydro-2H-pyran-2-yl)oxy)-3'-fluoro-3-methoxy-[1,1'-biphenyl]-2-yl)ethyl)acetamide (42); and N-(2-(5-(((3R,4S,5R)-3,4-dihydroxy-5-methoxy-6,6-dimethyltetrahydro-2H-pyran-2-yl)oxy)-3'-fluoro-4-methyl-[1,1'-biphenyl]-2-yl)ethyl)acetamide (43).

In a specific aspect, the compound is selected from: N-(2-(5-(((3R,4S,5R)-3,4-dihydroxy-5-methoxy-6,6-dimethyltetrahydro-2H-pyran-2-yl)oxy)-3'-fluoro-[1,1'-biphenyl]-2-yl)ethyl)acetamide (11b); N-(2-(5-(((3R,4S,5R)-3,4-dihydroxy-5-methoxy-6,6-dimethyltetrahydro-2H-pyran-2-yl)oxy)-4'-fluoro-[1,1'-biphenyl]-2-yl)ethyl)acetamide (11c); N-(2-(2'-chloro-5-(((3R,4S,5R)-3,4-dihydroxy-5-methoxy-6,6-dimethyltetrahydro-2H-pyran-2-yl)oxy)-[1,1'-biphenyl]-2-yl)ethyl)acetamide (11d); N-(2-(3'-chloro-5-(((3R,4S,5R)-3,4-dihydroxy-5-methoxy-6,6-dimethyltetrahydro-2H-pyran-2-yl)oxy)-[1,1'-biphenyl]-2-yl)ethyl)acetamide (11e); N-(2-(5-(((3R,4S,5R)-3,4-dihydroxy-5-methoxy-6,6-dimethyltetrahydro-2H-pyran-2-yl)oxy)-3'-(trifluoromethyl)-[1,1'-biphenyl]-2-yl)ethyl)acetamide (11f); or N-(2-(5-(((3R,4S,5R)-3,4-dihydroxy-5-methoxy-6,6-dimethyltetrahydro-2H-pyran-2-yl)oxy)-4'-(trifluoromethyl)-[1,1'-biphenyl]-2-yl)ethyl)acetamide (11g).

In another specific aspect, the compound is selected from N-(2-(5-(((3R,4S,5R)-3,4-dihydroxy-5-methoxy-6,6-dimethyltetrahydro-2H-pyran-2-yl)oxy)-3'-fluoro-[1,1'-biphenyl]-2-yl)ethyl)acetamide (11b); N-(2-(3'-chloro-5-(((3R,4S,5R)-3,4-dihydroxy-5-methoxy-6,6-dimethyltetrahydro-2H-pyran-2-yl)oxy)-[1,1'-biphenyl]-2-yl)ethyl)acetamide (11e); or N-(2-(5-(((3R,4S,5R)-3,4-dihydroxy-5-methoxy-6,6-dimethyltetrahydro-2H-pyran-2-yl)oxy)-3'-(trifluoromethyl)-[1,1'-biphenyl]-2-yl)ethyl)acetamide (11f).

In some embodiments, the disclosure provides a pharmaceutical composition comprising a therapeutically effective amount of a compound or pharmaceutically acceptable salt of a compound of Formula (I) wherein the substituents are as defined above for $R_1$, $R_2$, $R_3$, $R_4$, $R_5$, $R_6$, $R_7$, $R_8$, $R_{22}$, $R_{23}$, $R_{24}$, Z, $Z_1$, $X_1$, $X_2$, $X_3$, R', R", X, Y and n in combination with a pharmaceutically acceptable carrier.

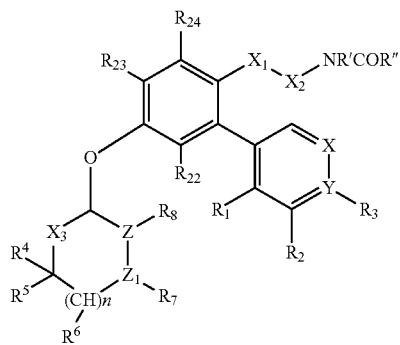

(I)

In some embodiments, the disclosure provides a compound of Formula (I) wherein $X_3$ is O. In some embodiments, the disclosure provides a compound of Formula (I) wherein $X_3$ is $CH_2$. In some embodiments, the disclosure provides a compound of Formula (I) wherein one of $R_1$, $R_2$ and $R_3$ is not H. In some embodiments, the disclosure provides a compound of Formula (I) wherein one of $R_1$, $R_2$ and $R_3$ is halo. In some embodiments, the disclosure provides a compound of Formula (I) wherein one of $R_{22}$, $R_{23}$ and $R_{24}$ is not H. In some embodiments, the disclosure provides a compound of Formula (I) wherein one of $R_{22}$, $R_{23}$ and $R_{24}$ is hydroxyl, alkoxy or alkyl. In some embodiments, the disclosure provides a compound of Formula (I) wherein $X_1$ is —CH═, and $X_2$ is ═CH—. In some embodiments, the disclosure provides a compound of Formula (I) wherein $X_1$ and $X_2$ are both $CH_2$. In some embodiments, the disclosure provides a compound of Formula (I) wherein Z-$Z_1$ is —C═C—. In some embodiments, the disclosure provides a compound of Formula (I) wherein $R_4$ and $R_5$ are independently alkyl. In some embodiments, the disclosure provides a compound of Formula (I) wherein $R_6$ is alkoxy, aralkoxy or alkyl. In some embodiments, n=1.

In some embodiments, $Z_1$ is O and $R_7$ is absent. In some embodiments, $Z_1$ is S and $R_7$ is absent. In some embodiments, $Z_1$ is N and $R_7$ is alkyl, hydrogen or carboxyl.

In some embodiments, the compound of Formula (I) is selected from a compound of Formula (Ia) wherein the substituents are as defined above for $R_1$, $R_2$, $R_3$, $R_4$, $R_5$, $R_6$, $R_7$, $R_8$, $X_1$, $X_2$, R', R", X, Y and n.

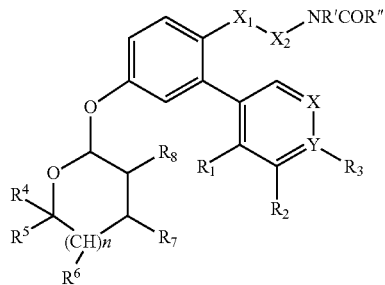

(Ia)

In some embodiments, the compound of Formula (I) is selected from a compound of Formula (Ia) wherein the substituents are as defined above for $R_1$, $R_2$, $R_3$, $R_4$, $R_5$, $R_6$, $R_7$, $R_8$, $X_1$, $X_2$, R', R", X, Y and n.

In other embodiments, the disclosure provides a method for treating or preventing a neurodegenerative disorder in a subject in need thereof comprising administering to the subject a therapeutically effective amount of a compound or pharmaceutically acceptable salt of a compound of Formula (I), wherein the substituents are defined above.

In other embodiments, the disclosure provides for use of a compound of Formula (I), or a pharmaceutically acceptable salt thereof, in the manufacture of a composition for treating a neurodegenerative disorder in a subject in need thereof; wherein the composition is to be administered in an amount effective to alleviate or prevent symptoms of neuronal glucotoxicity. In a specific embodiment, the neuronal glucotoxicity is sensory neuron glucotoxicity.

In another specific embodiment, the neurodegenerative disorder is diabetic peripheral neuropathy.

In still another embodiment, the compounds of the present invention exhibit neuroprotective effects by upregulation of Hsp70.

DETAILED DESCRIPTION OF PREFERRED EMBODIMENT

Figure 1:
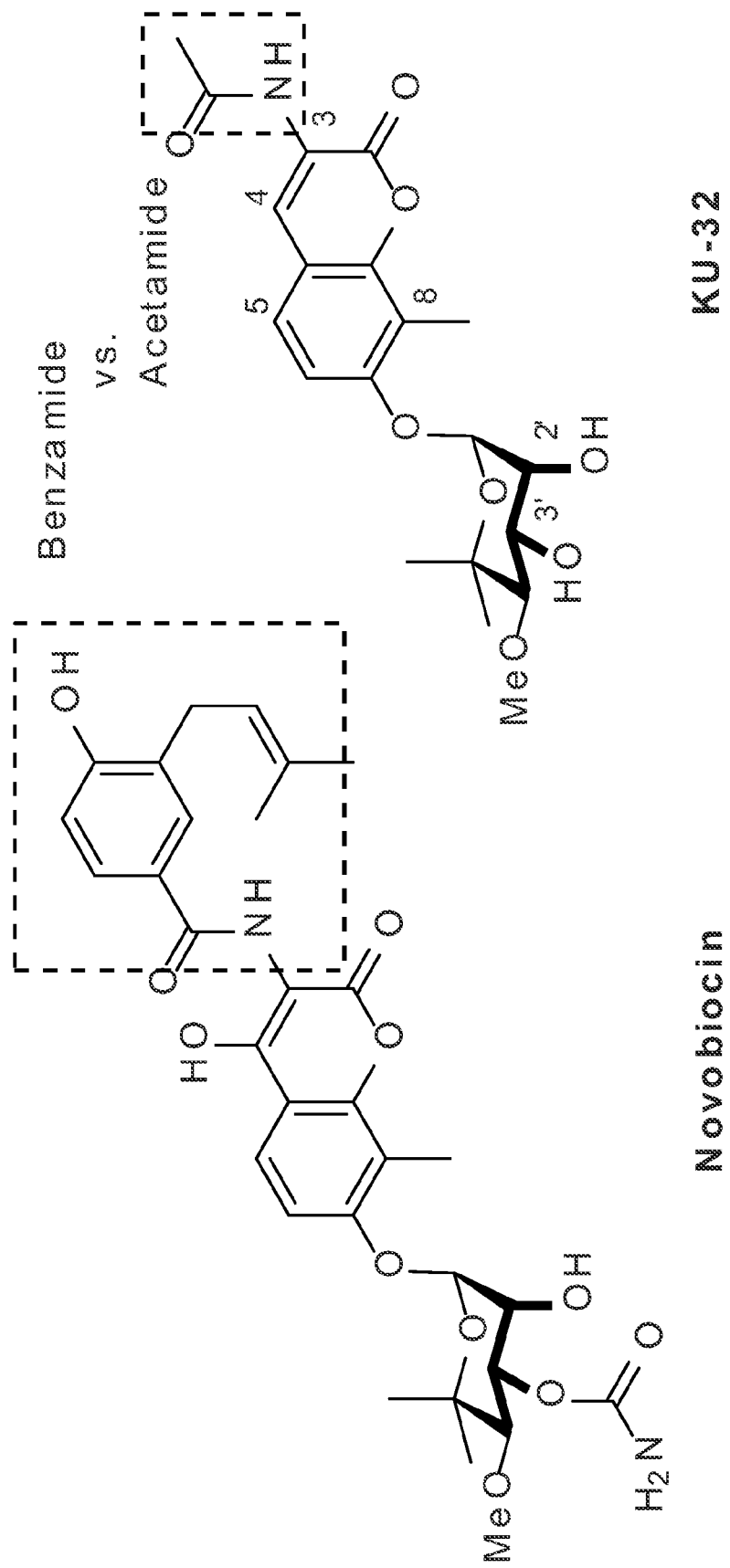
FIG. 1 shows chemical structures of novobiocin and KU-32.

Molecular terms, when used in this application, have their common meaning unless otherwise specified. It should be noted that the alphabetical letters used in the formulas of the present invention should be interpreted as the functional groups, moieties, or substituents as defined herein. Unless otherwise defined, the symbols will have their ordinary and customary meaning to those skilled in the art.

The term "acyl" refers to —COR wherein R used in this definition is hydrogen, alkyl, alkenyl, alkynyl, carbocyclic, heterocylic, aryl, or aralkyl. Most preferably, R is hydrogen, alkyl, aryl, or aralkyl.

The term "amido" indicates either a C-amido group such as —CONR'R" or an N-amido group such as —NR'COR" wherein R' and R" as used in this definition are independently hydrogen, alkyl, alkenyl, alkynyl, alkoxy, carbocyclic, heterocylic, aryl, or aralkyl. A "sulfoamido" group includes the —NR'—SO$_2$—R". Most preferably, R' and R" are hydrogen, alkyl, aryl, or aralkyl.

The term "amino" signifies a primary, secondary or tertiary amino group of the formula —NR'R" wherein R' and R" as used in this definition are independently hydrogen, alkyl, alkyenyl, alkynyl, aralkyl, carbocyclic, heterocyclic, aralkyl, or other amino (in the case of hydrazide) or R' and R" together with the nitrogen atom to which they are attached, form a ring having 4 to 8 atoms. Thus, the term "amino," as used herein, includes unsubstituted, monosubstituted (e.g., monoalkylamino or monoarylamino), and disubstituted (e.g., dialkylamino or aralkylamino) amino groups. Amino groups include —NH$_2$, methylamino, ethylamino, dimethylamino, diethylamino, methyl-ethylamino, pyrrolidin-1-yl, or piperidino, morpholino, etc. Other exemplary "amino" groups forming a ring include pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, quinolizinyl. The ring containing the amino group may be optionally substituted with another amino, alkyl, alkenyl, alkynyl, halo, or hydroxyl group.

The term "alkyl" refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl, and the like. Preferred "alkyl" groups herein contain 1 to 12 carbon atoms. Most preferred are "lower alkyl" which refer to an alkyl group of one to six, more preferably one to four, carbon atoms. The alkyl group may be optionally substituted with an amino, alkyl, cycloalkyl, halo, or hydroxyl group.

The term "alkoxy" denotes oxy-containing groups substituted with an alkyl, or cycloalkyl group. Examples include, without limitation, methoxy, ethoxy, tert-butoxy, and cyclohexyloxy. Most preferred are "lower alkoxy" groups having one to six carbon atoms. Examples of such groups include methoxy, ethoxy, propoxy, butoxy, isopropoxy, and tert-butoxy groups.

The terms "alkenyl" and "alkynyl" refer to unsaturated aliphatic groups analogous in length and possible substitution to the alkyls described above, but that contain at least one double bond or triple bond respectively.

The term "aryl" means a carbocyclic aromatic system containing one, two, or three rings wherein such rings may be attached together in a pendant manner or may be fused. The term "fused" means that a second ring is present (i.e., attached or formed) by having two adjacent atoms in common (i.e., shared) with the first ring. The term "fused" is equivalent to the term "condensed." The term "aryl" embraces aromatic groups such as phenyl, naphthyl, tetrahydronaphthyl, indane, and biphenyl. The aryl group may optionally be substituted with an amino, alkyl, halo, hydroxyl, carbocyclic, heterocyclic, or another aryl group.

The term "aralkyl" embraces aryl-substituted alkyl moieties. Preferable aralkyl groups are "lower aralkyl" groups having aryl groups attached to alkyl groups having one to six carbon atoms. Examples of such groups include benzyl, diphenylmethyl, triphenylmethyl, phenylethyl, and diphenylethyl. The terms benzyl and phenylmethyl are interchangeable.

The term "aryloxy" embraces aryl groups, as defined above, attached to an oxygen atom. The aryloxy groups may optionally be substituted with a halo, hydroxyl, or alkyl group. Examples of such groups include phenoxy, 4-chloro-3-ethylphenoxy, 4-chloro-3-methylphenoxy, 3-chloro-4-ethylphenoxy, 3,4-dichlorophenoxy, 4-methylphenoxy, 3-trifluoromethoxyphenoxy, 3-trifluoromethylphenoxy, 4-fluorophenoxy, 3,4-dimethylphenoxy, 5-bromo-2-fluorophenoxy, 4-bromo-3-fluorophenoxy, 4-fluoro-3-methylphenoxy, 5,6,7,8-tetrahydronaphthyloxy, 3-isopropylphenoxy, 3-cyclopropylphenoxy, 3-ethylphenoxy, 4-tert-butylphenoxy, 3-pentafluoroethylphenoxy, and 3-(1,1,2,2-tetrafluoroethoxy)phenoxy.

The term "arylalkoxy" embraces oxy-containing aralkyl groups attached through an oxygen atom to other groups. "Lower arylalkoxy" groups are those phenyl groups attached to lower alkoxy group as described above. Examples of such groups include benzyloxy, 1-phenylethoxy, 3-trifluoromethoxybenzyloxy, 3-trifluoromethylbenzyloxy, 3,5-difluorobenzyloxy, 3-bromobenzyloxy, 4-propylbenzyloxy, 2-fluoro-3-trifluoromethylbenzyloxy, and 2-phenylethoxy.

The term "carboxyl" refers to —R'C(=O)OR", wherein R' and R" as used in this definition are independently hydrogen, alkyl, alkenyl, alkynyl, carbocyclic, heterocyclic, aryl, or aralkyl or R' can additionally be a covalent bond. "Carboxyl" includes both carboxylic acids, and carboxylic acid esters. The term "carboxylic acid" refers to a carboxyl group in which R" is hydrogen. Such acids include formic, acetic, propionic, butyric, valeric acid, 2-methyl propionic acid, oxirane-carboxylic acid, and cyclopropane carboxylic acid. The term "carboxylic acid ester" or "ester" refers to a carboxyl group in which R" is alkyl, alkenyl, alkynyl, carbocyclic, heterocyclic, aryl, or aralkyl.

The term "carbocyclic" refers to a group that contains one or more covalently closed ring structures, and that the atoms forming the backbone of the ring are all carbon atoms. The ring structure may be saturated or unsaturated. The term thus distinguishes carbocyclic from heterocyclic rings in which the ring backbone contains at least one non-carbon atom. The term carbocylic encompasses cycloalkyl ring systems.

The terms "cycloalkane" or "cyclic alkane" or "cycloalkyl" refer to a carbocyclic group in which the ring is a cyclic aliphatic hydrocarbon, for example, a cyclic alkyl group preferably with 3 to 12 ring carbons. "Cycloalkyl" includes, by way of example, cyclopropyl, cyclobutyl, cyclopentyl, cyclohexyl, cycloheptyl, or cyclooctyl, and the like. The cycloalkyl group may be optionally substituted with an amino, alkyl, halo, or hydroxyl group.

The term "ether" refers to the group —R'—O—R" wherein R' and R" as used in this definition are independently hydrogen, alkyl, alkenyl, alkynyl, carbocyclic, heterocyclic, aryl, or aralkyl, and R' can additionally be a covalent bond attached to a carbon.

The terms "halo" or "halogen" refer to fluoro, chloro, bromo, or iodo, usually regarding halo substitution for a hydrogen atom in an organic compound.

The term "heterocyclic", "het", or "heterocycle" means an optionally substituted, saturated or unsaturated, aromatic or non-aromatic cyclic hydrocarbon group with 4 to about 12 carbon atoms, preferably about 5 to about 6, wherein 1 to about 4 carbon atoms are replaced by nitrogen, oxygen or sulfur. Exemplary heterocyclic which are aromatic include groups piperidinyl, pyridinyl, furanyl, benzofuranyl, isobenzofuranyl, pyrrolyl, thienyl, 1,2,3-triazolyl, 1,2,4-triazolyl, indolyl, imidazolyl, thiazolyl, thiadiazolyl, pyrimidinyl, oxazolyl, triazinyl, and tetrazolyl. Exemplary heterocycles include benzimidazole, dihydrothiophene, dioxin, dioxane, dioxolane, dithiane, dithiazine, dithiazole, dithiolane, furan, indole, 3-H indazole, 3-H-indole, imidazole, indolizine, isoindole, isothiazole, isoxazole, morpholine, oxazole, oxadiazole, oxathiazole, oxathiazolidine, oxazine, oxadiazine, piperazine, piperidine, purine, pyran, pyrazine, pyrazole, pyridine, pyrimidine, pyrimidine, pyridazine, pyrrole, pyrrolidine, tetrahydrofuran, tetrazine, thiadiazine, thiadiazole, thiatriazole, thiazine, thiazole, thiomorpholine, thiophene, thiopyran, triazine, and triazole. The heterocycle may be optionally substituted with an amino, alkyl, alkenyl, alkynyl, halo, hydroxyl, carbocyclic, thio, other heterocyclic, or aryl group. Exemplary heterocyclic groups include 1-piperidinyl, 2-piperidinyl, 3-piperidinyl, 4-piperidinyl, 1-pyrrolyl, 2-pyrrolyl, 3-pyrrolyl, 1-indolyl, 2-indolyl, 3-indolyl, 1-pyridyl, 2-pyridyl, 3-pyridyl, 4-pyridyl, 1-imidazolyl, 2-imidazolyl, 3-imidazolyl, 4-imidazolyl, 1-pyrazolyl, 2 pyrazolyl, 3-pyrazolyl, 4-pyrazolyl, 5-pyrazolyl, 1-pyrazinyl, 2-pyrazinyl, 1-pyrimidinyl, 2-pyrimidinyl, 4-pyrimidinyl, 5-pyrimidinyl, 1-pyridazinyl, 2-pyridazinyl, 3-pyridazinyl, 4-pyridizinyl, 1-indolizinyl, 2-indolizinyl, 3-indolizinyl, 4-indolizinyl, 5-indolizinyl, 6-indolizinyl, 7-indolizinyl, 8-indolizinyl, 1-isoindolyl, 2-isoindolyl, 3-isoindolyl, 4-isoindolyl, 5-isoindolyl.

The term "hydroxy" or "hydroxyl" refers to the substituent —OH.

The term "oxo" shall refer to the substituent =O.

The term "nitro" means —NO$_2$.

The term "sulfanyl" refers to —SR' where R' as used in this definition is hydrogen, alkyl, alkenyl, alkynyl, carbocyclic, heterocyclic, aryl, or aralkyl.

The term "sulfenyl" refers to —SOR' where R' as used is this definition is hydrogen, alkyl, alkenyl, alkynyl, carbocyclic, heterocyclic, aryl, or aralkyl.

The term "sulfonyl" refers to —SOR' where R' as used in this definition is hydrogen, alkyl, alkenyl, alkynyl, carbocyclic, heterocyclic, aryl, or aralkyl.

"Optional" or "optionally" means that the subsequently described event or circumstance may or may not occur, and that the description includes instances where said event or circumstance occurs and instances in which it does not. "Optionally" is inclusive of embodiments in which the described conditions is present and embodiments in which the described condition is not present. For example, "optionally substituted phenyl" means that the phenyl may or may not be substituted, and that the description includes both unsubstituted phenyl and phenyl wherein there is substitution. "Optionally" is inclusive of embodiments in which the described conditions is present and embodiments in which the described condition is not present.

The compounds of the present invention can exist in tautomeric, geometric, or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof, as falling within the scope of the invention.

Also included in the family of compounds of the present invention are the pharmaceutically acceptable salts, esters, and prodrugs thereof. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of compounds of the present invention be prepared from inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of the present invention include metallic salts made from aluminum, calcium, lithium, magnesium, potassium, sodium and zinc or organic salts made from N,N'-dibenzylethylenel-diamine, choline, chloroprocaine, diethanolamine, ethylenediamine, meglumine (N-methylglucamine) and procain. All of these salts may be prepared by conventional means from the corresponding compounds of by reacting, for example, the appropriate acid or base with the compounds of the present invention.

As used herein, the term "pharmaceutically acceptable ester" refers to esters which hydrolyze in vivo and include, but are not limited to, those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates, and ethyl succinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, *Prodrugs as Novel delivery Systems*, Vol. 14 of the A.C.S. Symposium Series and in Edward B. Roche, ed., *Bioreversible Carriers in Drug Design, American Pharmaceutical Association and Pergamon Press*, (1987), both of which are incorporated by reference herein.

The term "neuroprotection" embraces inhibition of progressive deterioration of neurons that leads to cell death.

The term "neurodegenerative disorder" embraces a disorder in which progressive loss of neurons occurs either in the peripheral nervous system or in the central nervous system. In one embodiment, the condition treated and/or prevented by the compounds, compositions and methods of the disclosure is a neurodegenerative disorder. Without being bound by theory, it is believed that the compounds and compositions of the present disclosure provide neuroprotective effects of the Hsp90 inhibitor(s) during the treatment of the neurodegenerative disorder by inhibiting the progressive deterioration of neurons that leads to cell death.

In one aspect, the neurodegenerative disorder is sensory neuron glucotoxicity resultant from, e.g., hyperglycemia associated with a diabetic condition, and resultant in, e.g., diabetic peripheral neuropathy.

Examples of neurodegenerative disorders include, but are not limited to chronic neurodegenerative diseases such as diabetic peripheral neuropathy (including third nerve palsy, mononeuropathy, mononeuropathy multiplex, diabetic amyotrophy, autonomic neuropathy and thoracoabdominal neuropathy), Alzheimer's disease, age-related memory loss, senility, age-related dementia, Pick's disease, diffuse Lewy body disease, progressive supranuclear palsy (Steel-Richardson syndrome), multisystem degeneration (Shy-Drager syndrome), motor neuron diseases including amyotrophic lateral sclerosis ("ALS"), degenerative ataxias, cortical basal degeneration, ALS-Parkinson's-Dementia complex of Guam, subacute sclerosing panencephalitis, Huntington's disease, Parkinson's disease, multiple sclerosis ("MS"), synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Wernicke-Korsakoff s related dementia (alcohol induced dementia), Werdnig-Hoffmann disease, Kugelberg-Welander disease, Tay-Sach's disease, Sandhoff disease, familial spastic disease, Wohifart-Kugelberg-Welander disease, spastic paraparesis, progressive multifocal leukoencephalopathy, and prion diseases (including Creutzfeldt-Jakob, Gerstmann-Straussler-Scheinker disease, Kuru and fatal familial insomnia). Other conditions also included within the methods of the present invention include age-related dementia and other dementias, and conditions with memory loss including vascular dementia, diffuse white matter disease (Binswanger's disease), dementia of endocrine or metabolic origin, dementia of head trauma and diffuse brain damage, dementia pugilistica, and frontal lobe dementia. Also other neurodegenerative disorders resulting from cerebral ischemia or infarction including embolic occlusion and thrombotic occlusion as well as intracranial hemorrhage of any type (including, but not limited to, epidural, subdural, subarachnoid, and intracerebral), and intracranial and intravertebral lesions (including, but not limited to, contusion, penetration, shear, compression, and laceration). Thus, the term also encompasses acute neurodegenerative disorders such as those involving stroke, traumatic brain injury, schizophrenia, peripheral nerve damage, hypoglycemia, spinal cord injury, epilepsy, and anoxia and hypoxia.

In some embodiments, the neurodegenerative disorder is amyloidosis. Amyloidosis is observed in Alzheimer's Disease, hereditary cerebral angiopathy, nonneuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis arthropathy, and Finnish and Iowa amyloidosis. In preferred embodiments, the neurodegenerative disorder treated and/or prevented using the methods and compositions of the disclosure is diabetic peripheral neuropathy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the analogue or derivative from one organ, or portion of the body, to another organ, or portion of the body. Each carrier must be "acceptable" in the sense of being compatible with the other ingredients of the formulation and not injurious to the patient. Some examples of materials which may serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The "patient" or "subject" to be treated with the compounds of the present invention can be any animal, e.g., dogs, cats, mice, monkeys, rats, rabbits, horses, cows, guinea pigs, sheep, and is preferably a mammal, such as a domesticated animal or a livestock animal. In another aspect, the patient is a human.

The term "inhibit" or "inhibiting" refers to a statistically significant and measurable reduction in neurotoxicity, preferably as measured by one or more of the assays discussed herein, preferably a reduction of at least about 10% versus control, more preferably a reduction of about 50% or more, still more preferably a reduction of about 60%, 70%, 80%, 90%, or more.

The term "preventing" as used herein means that the compounds of the present invention are useful when administered to a patient who has not been diagnosed as possibly having the disorder or disease at the time of administration, but who would normally be expected to develop the disorder or disease or be at increased risk for the disorder or disease. The compounds of the invention will slow the development of the disorder or disease symptoms, delay the onset of the disorder or disease, or prevent the individual from developing the disorder or disease at all. Preventing also includes administration of the compounds of the invention to those individuals thought to be predisposed to the disorder or disease due to age, familial history, genetic or chromosomal abnormalities, and/or due to the presence of one or more biological markers for the disorder or disease.

The term "treating," as used herein generally means that the compounds of the invention can be used in humans or animals with at least a tentative diagnosis of the disorder or disease. The compounds of the invention will delay or slow the progression of the disorder or disease thereby giving the individual a more useful life span. The term "treatment" embraces at least an amelioration of the symptoms associated with the disorder or disease in the patient is achieved, where amelioration is used in a broad sense to refer to at least a reduction in the magnitude of a parameter, e.g. symptom, associated with the condition being treated. As such, "treatment" also includes situations where the diseased condition or disorder, or at least symptoms associated therewith, are completely inhibited, e.g. prevented from happening, or stopped, e.g. terminated, such that the patient no longer suffers from the condition or disorder, or at least the symptoms that characterize the condition or disorder.

A "therapeutically effective amount" is an amount of a compound of the present invention or a combination of two or more such compounds, which inhibits, totally or partially, the progression of the condition or alleviates, at least partially, one or more symptoms of the condition. A therapeutically effective amount can also be an amount that is prophylactically effective. The amount that is therapeutically effective will depend upon the patient's size and gender, the condition to be treated, the severity of the condition and the result sought. For a given patient and condition, a therapeutically effective amount can be determined by methods known to those of skill in the art.

KU-32 is a first-generation novologue (a novobiocin-based, C-terminal, heat shock protein 90 (Hsp90) inhibitor) that decreases glucose-induced death of primary sensory neurons and reverses numerous clinical indices of diabetic peripheral neuropathy in mice. The structures of KU-32 and Novobiocin are shown in FIG. 1. The disclosure provides a new series of C-terminal Hsp90 inhibitors designed to optimize hydrogen bonding and hydrophobic interactions in an attempt to enhance neuroprotective activity. A series of substituted phenylboronic acids was used in a synthetic route to replace the coumarin lactone of KU-32 with an aryl moiety, such as a biphenyl moiety. Electronegative atoms placed at the meta-position of the B-ring were identified that exhibit improved cytoprotective activity, which while not wishing to be bound by theory, is believed to result from favorable interactions with Lys539 in the Hsp90 C-terminal binding pocket. Consistent with these results, a meta-3-fluorophenyl substituted novologue (11b) surprisingly exhibited a 14-fold lower $ED_{50}$ compared to KU-32 for protection against glucose-induced toxicity of primary sensory neurons.

Figure 2:
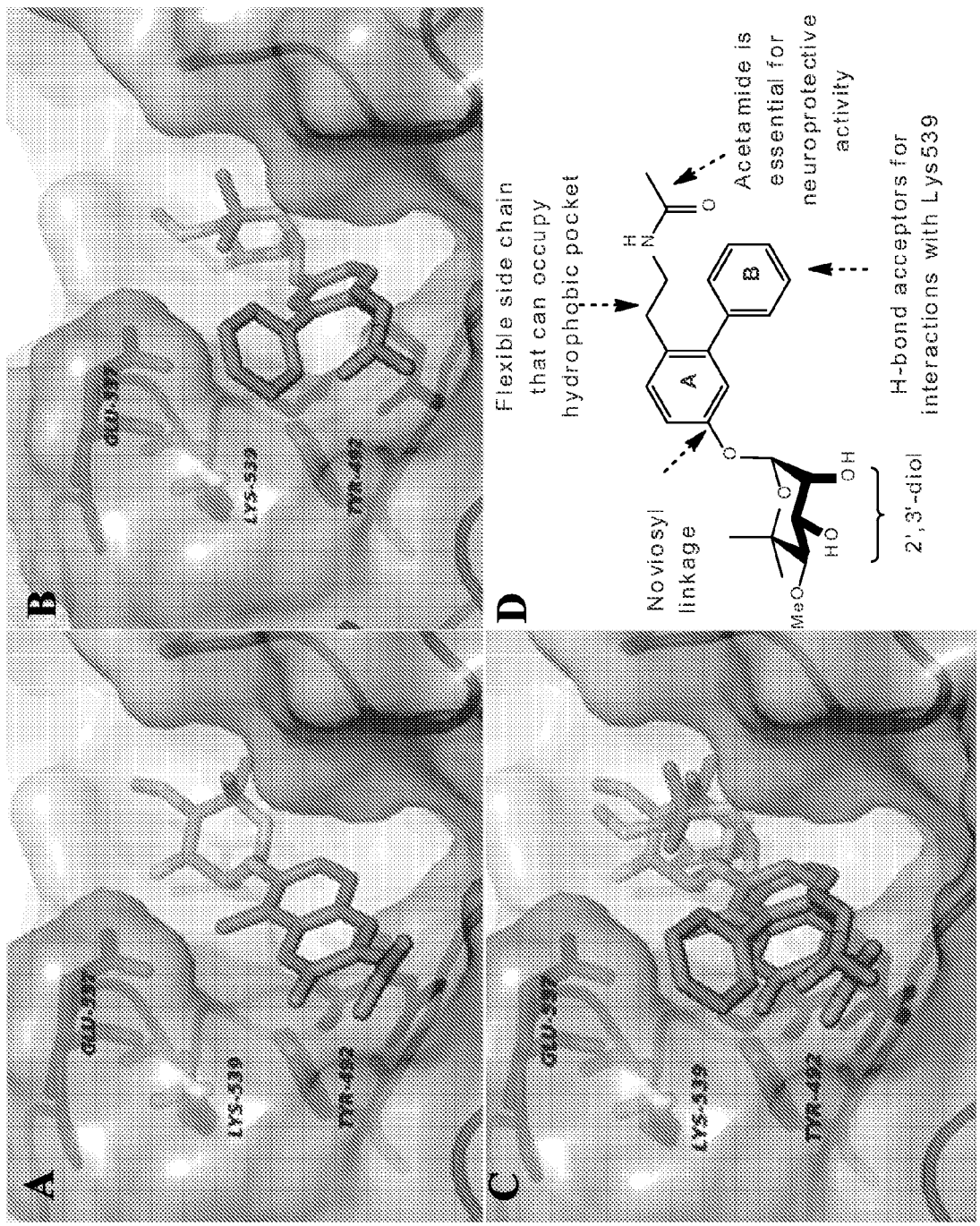
FIG. 2A shows a molecular model of KU-32 docked to Hsp90 C-terminal binding site.
FIG. 2B shows a molecular model of a novologue (structure shown in FIG. 2D) docked to Hsp90 C-terminal binding site.
FIG. 2C shows an overlay of KU-32 and a novologue (structure shown in FIG. 2D) docked to Hsp90 C-terminal binding site.
FIG. 2D shows the chemical structure of a novologue and its attributes.
Figure 3:
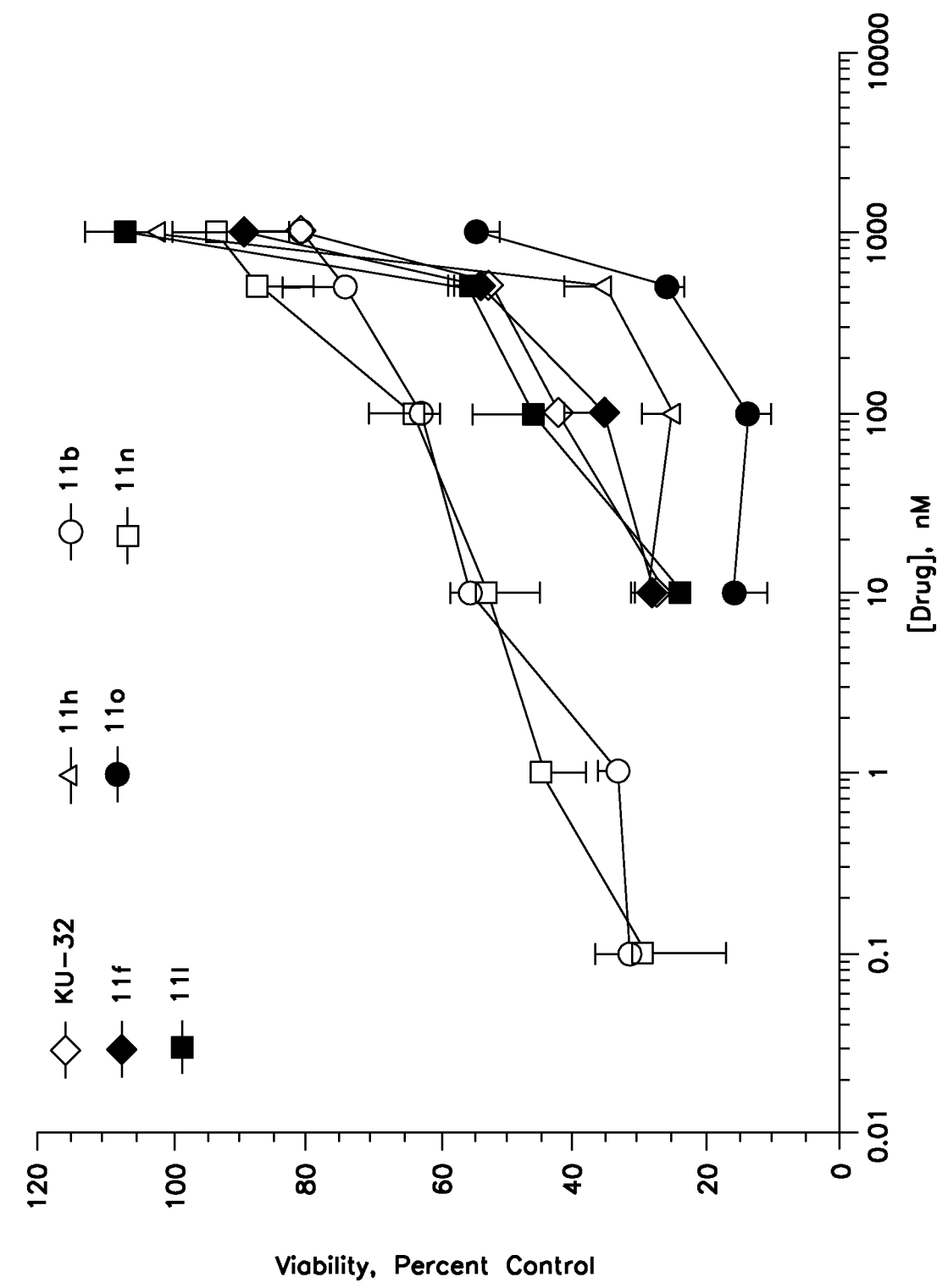
FIG. 3 shows the determination of $EC_{50}$ of select novologues KU-32, 11f, 11l, 11b, 11n, 11h, and 11o. DRG sensory neurons were incubated in the absence or presence of 0.1-1000 nM of the indicated novologue overnight and then subjected to 4 hrs of hyperglycemia. Cell viability was measured as described in Example 2 and the data expressed as percent of normoglycemic controls. Under hyperglycemic conditions and in the absence of any novologues, cell viability was 20%±7.

Recently, molecular modeling studies were performed by this lab and azide-containing novobiocin derivatives as photoaffinity probes were used to elucidate, for the first time, the Hsp90 C-terminal binding site. Matts, R. L.; Dixit, A.; Peterson, L. B.; Sun, L.; Voruganti, S.; Kalyanaraman, P.; Hartson, S. D.; Verkhivker, G. M.; Blagg, B. S., Elucidation of the Hsp90 C-Terminal Inhibitor Binding Site. *ACS Chem Biol* 2011. As shown in FIG. 2 (A-C), KU-32 docks to this region and appears to exhibit binding interactions with both the protein backbone and the amino acid side chains similar to those manifested by novobiocin. Interestingly, the coumarin lactone of KU-32 appears too distant from Lys539 to provide complementary interactions with this residue. In addition, the 3-amido side chain appears to project into a large hydrophobic pocket that could accommodate more flexible linkers. As a consequence of these observations, the novologue scaffold (FIG. 2D) was designed to project the B-ring into the pocket where Lys539 resides and to serve as a lead compound for further diversification. Without being bound to theory, it is possible that the flexible ethyl amide projecting from the A-ring could accommodate a number of orientations that could better occupy the large hydrophobic pocket that remains vacant in the presence of KU-32.

Based on the novologue design, construction of a parallel library was designed to validate this scaffold for use as a neuroprotective agent. The library was designed so that the 3'-carbamate on noviose was omitted; based upon prior studies that showed this group to be detrimental to Hsp90 inhibitory activity. Burlison, J. A.; Neckers, L.; Smith, A. B.; Maxwell, A.; Blagg, B. S. J., Novobiocin: Redesigning a DNA Gyrase Inhibitor for Selective Inhibition of Hsp90. *Journal of the American Chemical Society* 2006, 128 (48), 15529-15536.

In contrast, additional hydrophobic and hydrogen bonding interactions are provided by the incorporation of functionalities onto the 3-aryl substituent (B-ring), which was designed to provide complementary interactions with Lys539. The 4-ethyl acetamide is included to occupy the binding pocket about the coumarin ring system. In one aspect, consistent with data obtained from prior studies, the 7-noviosyl linkage is maintained as well the requisite 2',3'-diol. The disclosure provides the parallel synthesis of rationally designed novologues as Hsp90 C-terminal inhibitors and assessment of their neuroprotective activities.

Retrosynthetically, a library of novologues was designed for construction via four components (Scheme 1); a resorcinolic benzaldehyde (1), a variety of commercially available boronic acids (2a-p), noviose (3), and the acetamide side chain (Scheme 1). Prior work from this laboratory demonstrated that the trichloroacetimidate of noviose carbonate undergoes rapid coupling with phenols to give the desired α-anomer in high yield.

Scheme 1. Retrosynthetic analysis for the construction of novologue.

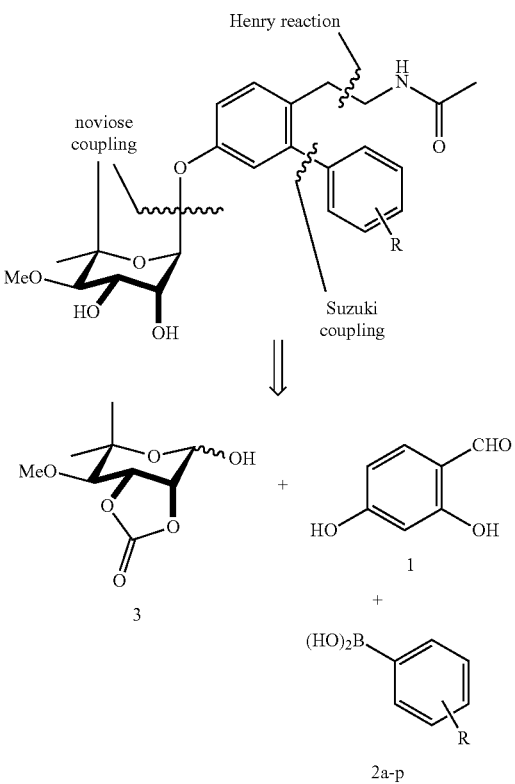

The boronic acids chosen for this study contain both electronic and steric moieties that could aid in elucidation of structure-activity relationships and provide crucial interactions with Lys539 and the surrounding pocket. Towards this goal, phenylboronic acids (Scheme 2) containing electronegative atoms at the meta- and para-positions were explored. In addition, hydrogen bond acceptors were included at these locations to provide potential hydrogen bonding interactions with the protonated form of Lys539. To serve as controls, hydrophobic groups (2j, 2k) and a tertiary amine (2l) were included in this series.

Scheme 2. Boronic acids selected for incorporation into novologue X scaffold.

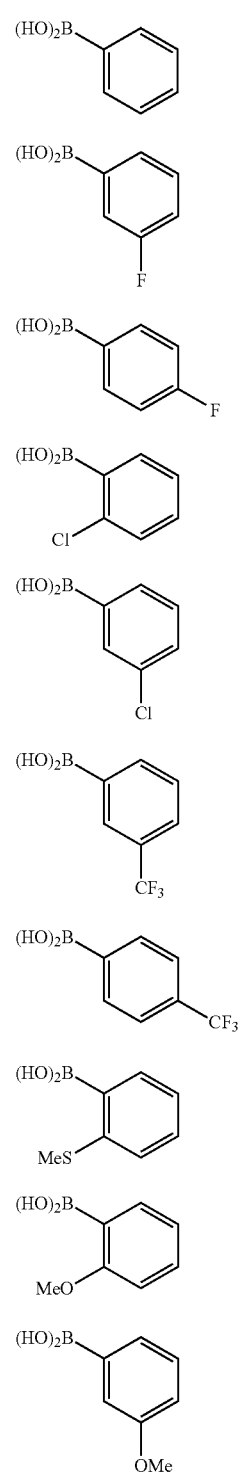

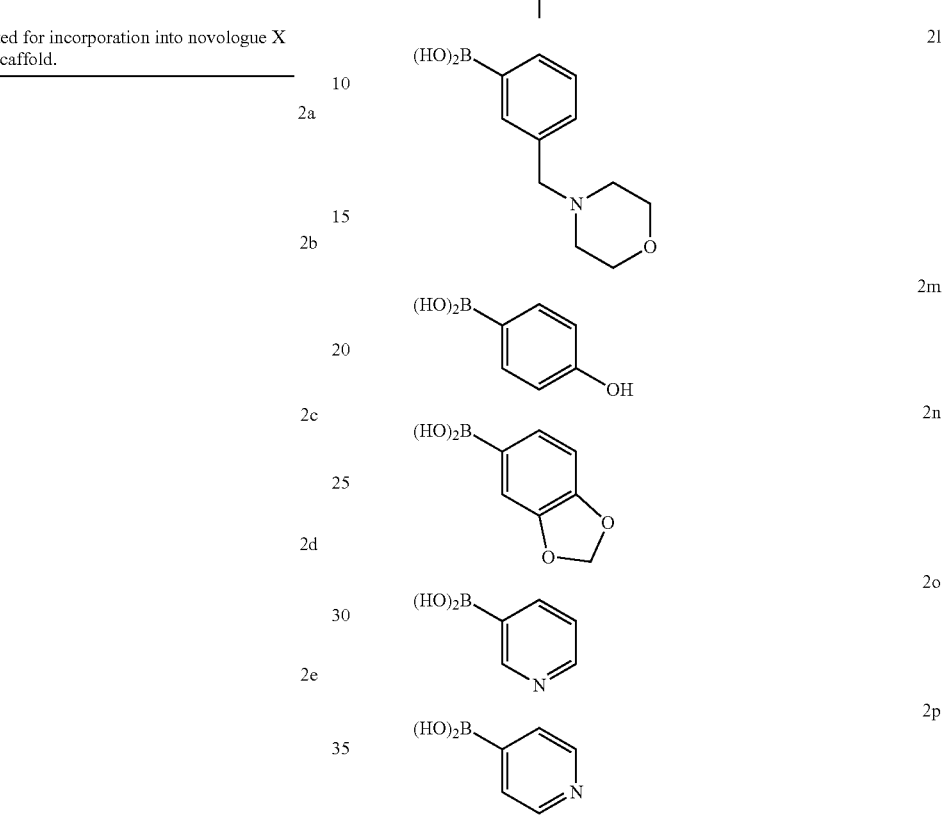

The synthesis of ethyl acetamide side chain containing novologues 11a-p, began with commercially available 2,4-dihydroxybenzaldehyde, 1. The 4-phenol of resorcinolic benzaldehyde 1 was protected as the corresponding benzyl ether 4, (Lee, M.; Gubernator, N. G.; Sulzer, D.; Sames, D., Development of pH-Responsive Fluorescent False Neurotransmitters. *Journal of the American Chemical Society* 2010, 132 (26), 8828-8830) and the 2-phenol converted to triflate 5 using trifluoromethanesulfonic anhydride and triethylamine (Scheme 3). Compound 5 was subsequently coupled with commercially available aryl boronic acids (2a-p) under standard Suzuki conditions to give biaryl ring systems 6a-p in good yields. Grasa, G. A.; Viciu, M. S.; Huang, J.; Zhang, C.; Trudell, M. L.; Nolan, S. P., Suzuki-Miyaura Cross-Coupling Reactions Mediated by Palladium/Imidazolium Salt Systems. *Organometallics* 2002, 21 (14), 2866-2873; Olson, J. P.; Gichinga, M. G.; Butala, E.; Navarro, H. A.; Gilmour, B. P.; Carroll, F. I., Synthesis and evaluation of 1,2,4-methyltriazines as mGluR5 antagonists. *Organic & Biomolecular Chemistry* 2011, 9 (11), 4276-4286.

Benzaldehydes 6a-p were converted to the corresponding nitrostyrenes (7a-p), following a Henry reaction with nitromethane and ammonium acetate. Fuganti, C.; Sacchetti, A., Biocatalytic enantioselective approach to 3-aryl-2-nitropropanols: Synthesis of enantioenriched (R)-5-methoxy-3-aminochroman, a key precursor to the antidepressant drug Robalzotan. *Journal of Molecular Catalysis B: Enzymatic* 2010, 66 (3-4), 276-284; Wood, K.; Black, D. S.; Kumar, N., Ring closing metathesis strategies towards functionalised 1,7-annulated 4,6-dimethoxyindoles. *Tetrahedron* 2011, 67 (22), 4093-4102.

Reduction of the nitro and olefin functionalities with lithium aluminum hydride was followed by acylation of the resulting amines to afford acetamides 8a-p in good yields. The benzyl ether of compounds 8a-p was cleaved under hydrogenolysis conditions to afford phenols 9a-p, which were coupled with the trichloroacetimidate of noviose carbonate 10[14] in the presence of a catalytic amount of boron trifluoride etherate. Burlison, J. A.; Neckers, L.; Smith, A. B.; Maxwell, A.; Blagg, B. S. J., Novobiocin: Redesigning a DNA Gyrase Inhibitor for Selective Inhibition of Hsp90. *Journal of the American Chemical Society* 2006, 128 (48), 15529-15536; Kusuma, B. R.; Peterson, L. B.; Zhao, H.; Vielhauer, G.; Holzbeierlein, J.; Blagg, B. S. J., Targeting the Heat Shock Protein 90 Dimer with Dimeric Inhibitors. *Journal of Medicinal Chemistry* 2011, 54 (18), 6234-6253.

The resulting noviosylated biaryl systems were exposed to methanolic ammonia to solvolyze the cyclic carbonate and give the desired novologues (11a-p) in good to moderate yields.

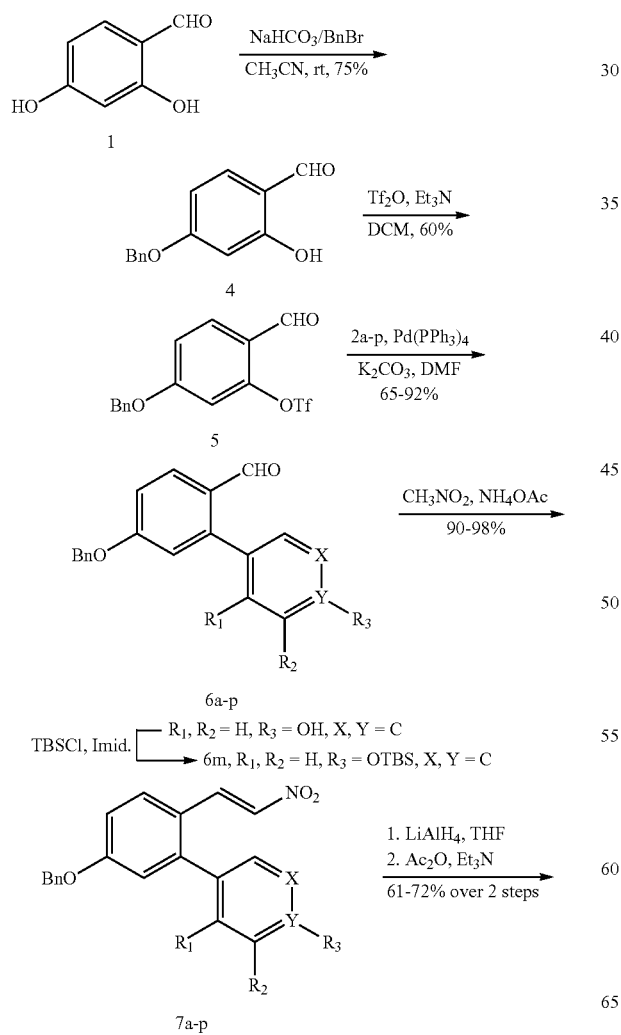

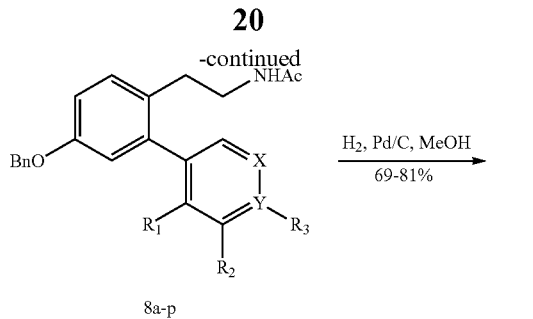

8a-p

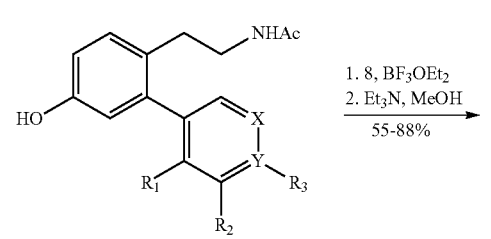

9a-p

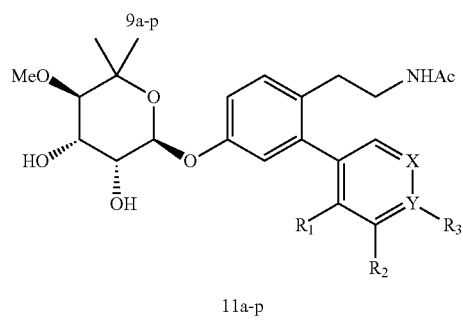

11a-p

TBAF ⎡ $R_1, R_2 = H, R_3 = OTBS, , X, Y = C$
      ⎣ 11m, $R_1, R_2 = H, R_3 = OH\ X, Y = C$

11a, $R_1, R_2, R_3 = H, X, Y = C$;
11b, $R_1, R_3 = H, R_2 = F, X, Y = C$
11c, $R_1, R_2 = H, R_3 = F, X, Y = C$;
11d, $R_2, R_3 = H, R_1 = Cl, X, Y = C$
11e, $R_1, R_3 = H, R_2 = Cl, X, Y = C$;
11f, $R_1, R_3 = H, R_2 = CF_3, X, Y = C$
11g $R_1, R_2 = H, R_3 = CF_3, X, Y = C$;
11h, $R_2, R_3 = H, R_1 = SMe, X, Y = C$
11i, $R_2, R_3 = H, R_1 = OMe, X, Y = C$;
11j, $R_1, R_3 = H, R_2 = OMe, X, Y = C$
11k, $R_1, R_3 = H, R_2 = Me, X, Y = C$;
11l, $R_1, R_3 = H, R_2 = CH_2$-morpholine, $X, Y = C$
11m, $R_1, R_2 = H, R_3 = OH\ X, Y = C$;
11n, $R_1 = H, , R_2, R_3 = OCH_2C$——, $X, Y = C$
11o, $R_1, R_2, R_3 = H, X = N, Y = C$;
11p, $R_1, R_2, R_3 = H, X = C, Y = N$

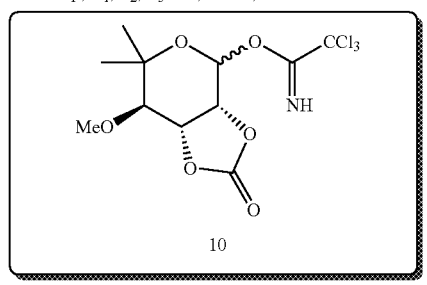

10

Compounds 41-43 are prepared in an analogous fashion by the protocol shown in Scheme 3.

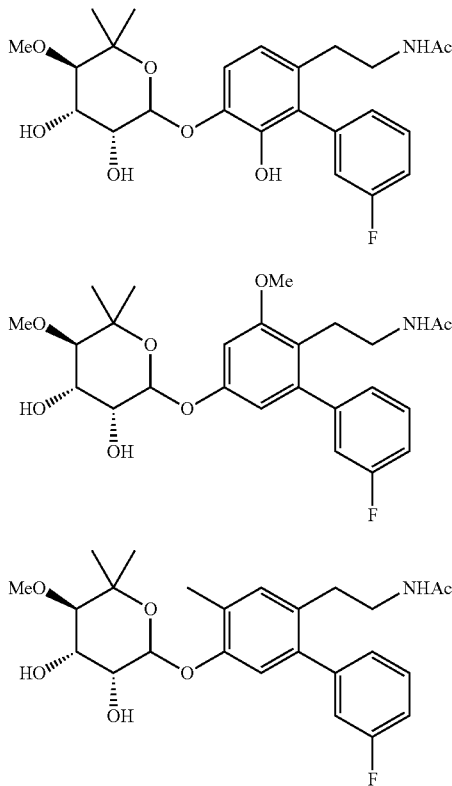

In some embodiments, the disclosure provides a compound of Formula (I) wherein $X_2$ together with $X_1$ form a carbocyclic ring having 3 to 7 ring members. For example, two cyclohexene analogues 20a-b were prepared to test the hypothesis regarding the region surrounding the flexible side chain (Scheme 4). Although these molecules contain the same linker length, these analogues contain a bulky cyclohexane tether between the biaryl ring system and the acetamide.

Synthesis of cyclohexene analogues 20a-b began with the previously described phenol 4, which was protected as the methoxymethyl (MOM) ether 13 (Toda, N. T., K.; Marumoto, S.; Takami, K.; Ori, M.; Yamada, N.; Koyama, K.; Naruto, S.; Abe, K. i; Yamazaki, R.; Hara, T.; Aoyagi, A.; Abe, Y.; Kaneko, T.; Kogen, H, Monoenomycin: a simplified trienomycin A analog that manifests anticancer activity. *Bioorganic & Medicinal Chemistry Letters*, ACS ASAP) before the aldehyde of which was converted to nitrostyrene 14 under Henry conditions. Olson et al., 2011 Id. The electron deficient nitrostyrene (14) was subjected to a Diels-Alder cycloaddition with excess butadiene to give an enantiomeric mixture of cyclohexene derivative 15 in excellent yield. Bryce, M. R.; Gardiner, J. M., Functionalised (+/−)-cephalotaxine analogues. *Journal of the Chemical Society, Chemical Communications* 1989, (16), 1162-1164.

The nitro group of 15 was selectively reduced to the amine via zinc dust and acidic isopropanol, (Brandt, G. E. L.; Blagg, B. S. J., Monoenomycin: a simplified trienomycin A analog that manifests anticancer activity. *ACS Medicinal Chemistry Letters*, ACS ASAP; Pei, Z.; Li, X.; von Geldern, T. W.; Madar, D. J.; Longenecker, K.; Yong, H.; Lubben, T. H.; Stewart, K. D.; Zinker, B. A.; Backes, B. J.; Judd, A. S.; Mulhern, M.; Ballaron, S. J.; Stashko, M. A.; Mika, A. K.; Beno, D. W. A.; Reinhart, G. A.; Fryer, R. M.; Preusser, L. C.; Kempf-Grote, A. J.; Sham, H. L.; Trevillyan, J. M., Discovery of ((4R,5S)-5-Amino-4-(2,4,5-trifluorophenyl)cyclohex-1-enyl)-(3-(trifluoromethyl)-5,6-dihydro-[1,2,4]triazolo[4,3-a]pyrazin-7(8H)-yl)methanone (ABT-341), a Highly Potent, Selective, Orally Efficacious, and Safe Dipeptidyl Peptidase IV Inhibitor for the Treatment of Type 2 Diabetes. *Journal of Medicinal Chemistry* 2006, 49 (22), 6439-6442) followed by acetylation to afford acetamide 16 in 71% yield over two steps. In order to construct the biaryl ring system, the MOM-ether was cleaved to give the phenol, which was then converted to the corresponding triflate, 17. A Suzuki reaction between 17 and 3-fluorophenylboronic acid or 3-(trifluoromethyl) phenylboronic acid, yielded biaryl compounds 18a or 18b, respectively. Finally, boron trifluoride etherate promoted removal of the benzyl ether (Andrieux, C. P.; Farriol, M.; Gallardo, I.; Marquet, J., Thermodynamics and kinetics of homolytic cleavage of carbon-oxygen bonds in radical anions obtained by electrochemical reduction of alkyl aryl ethers. *Journal of the Chemical Society, Perkin Transactions 2* 2002, (5), 985-990) on compounds 18a-b and gave phenols 19a-b. Lewis acid-catalyzed noviosylation of 19a-b, with activated noviose carbonate (10), followed by methanolysis, afforded an inseparable mixture of diastereomeric products, 20a-b.

Scheme 4. Synthesis of cyclohexene containing novologues.

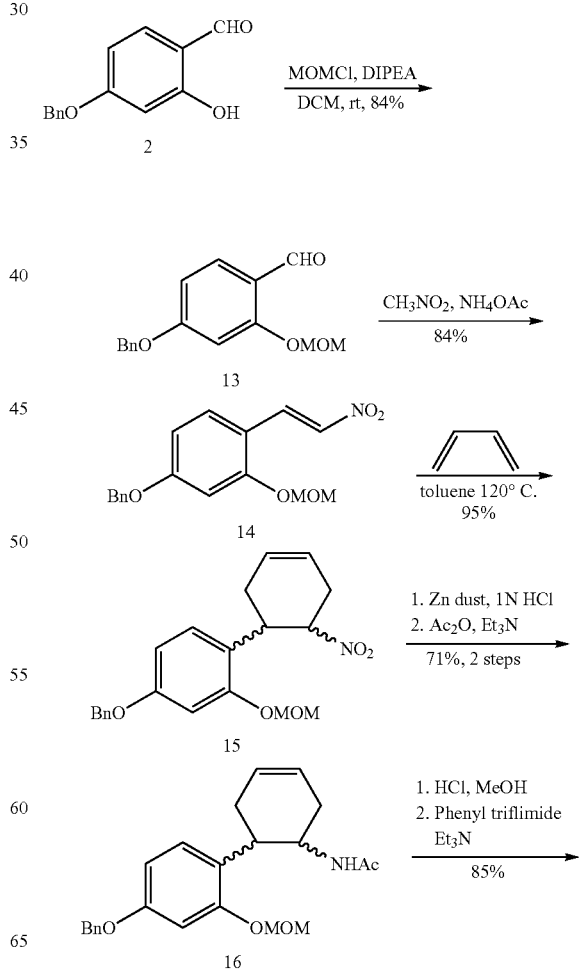

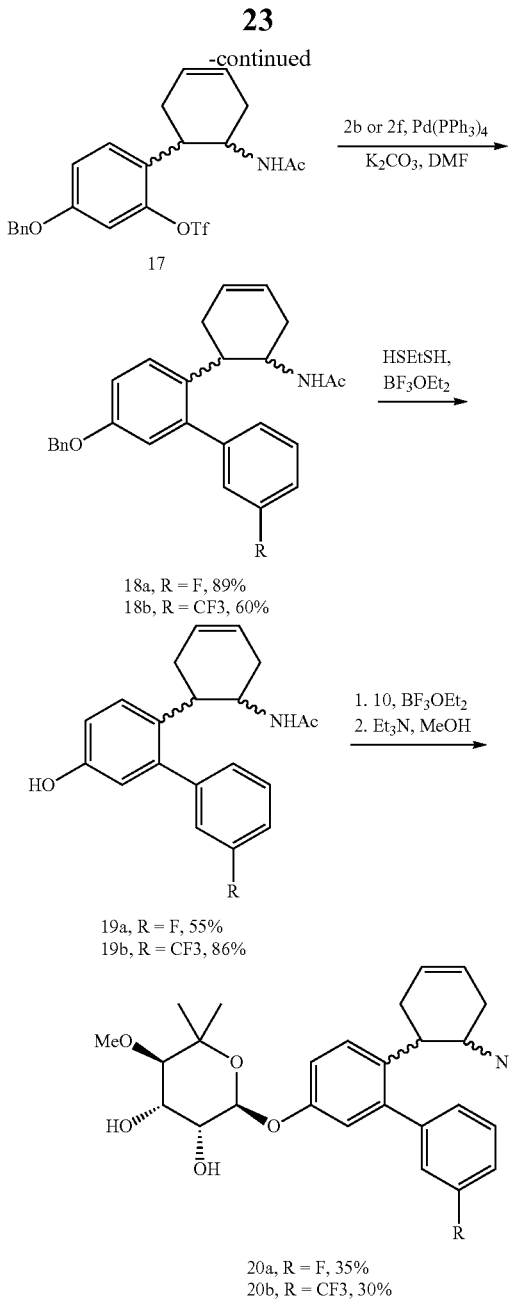

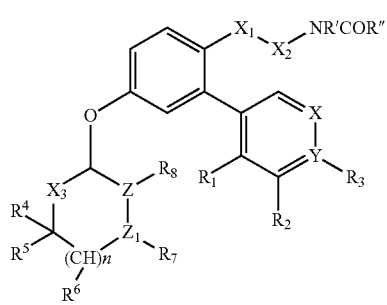

In some embodiments, the disclosure provides compounds of Formula (I) wherein $X_3$ is $CH_2$; in other words, wherein the noviose sugar substituent is replaced with a carbocyclic sugar analogue substituent.

In some embodiments, the disclosure provides compounds of Formula (IV)

wherein R', R'', $R_1$, $R_2$, $R_3$, $R_4$, $R_5$, $R_6$, $R_7$, $R_8$, X, $X_1$, $X_2$, $X_3$, Y, Z and $Z_1$ are as defined for a compound of Formula (I) above. In some embodiments, the disclosure provides a compound of Formula (IV) wherein $X_3$ is $CH_2$.

For example, certain compounds are prepared by the synthetic route shown in Scheme 5.

Scheme 5. Synthesis of carbocyclic sugar analogue compound 24.

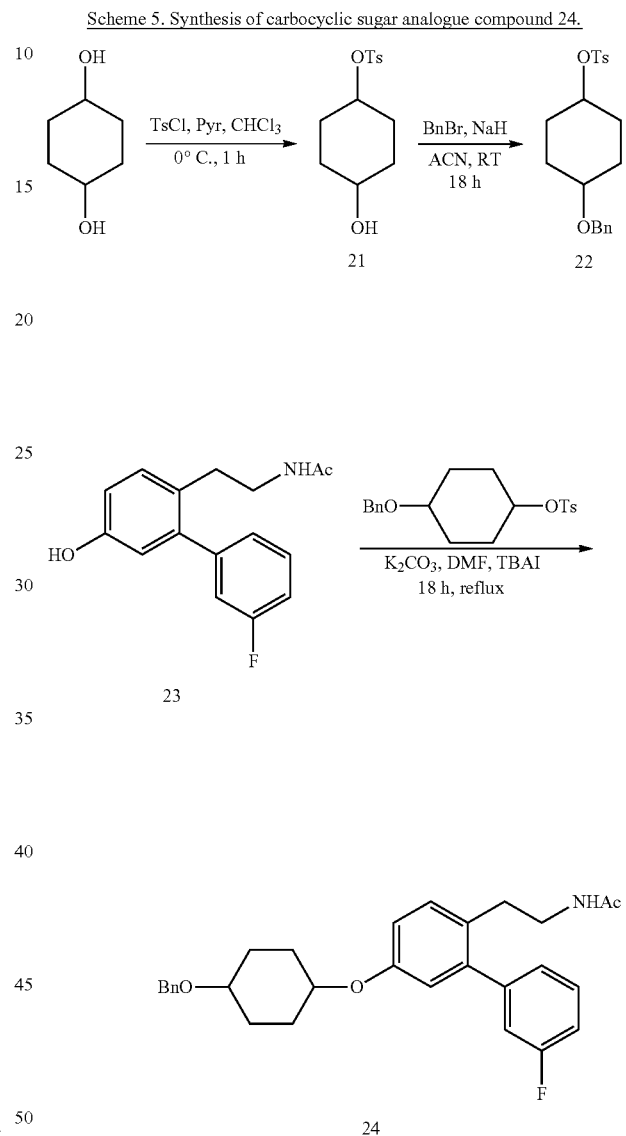

The phenol core intermediate 23 in Scheme 5 can be prepared by the synthetic route shown in Scheme 6.

Scheme 6. Synthesis of phenol core intermediate 23.

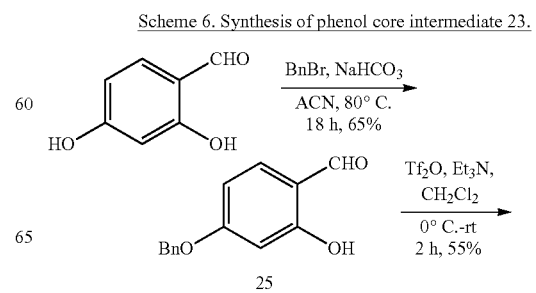

-continued

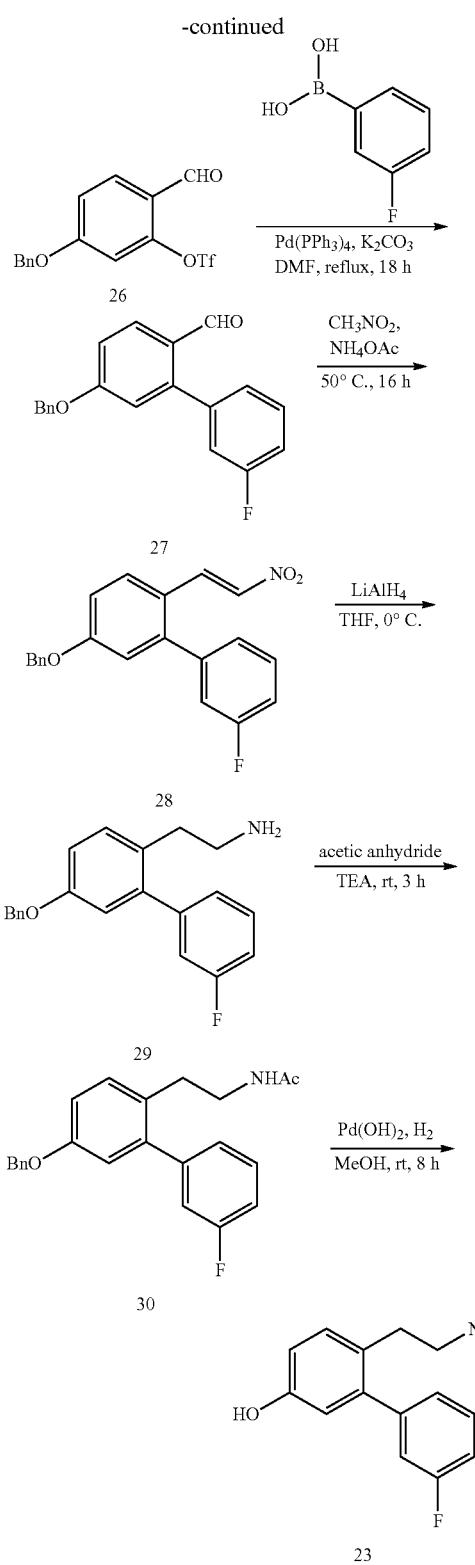

such as compound 36. For example, Scheme 7 shows a representative synthesis of compounds of Formula (I) or Formula (IV), where $X_3$ is $CH_2$ and Z is CH, such as compound 37.

Scheme 7. Synthesis of carbocyclic sugar analogues 36 and 37.

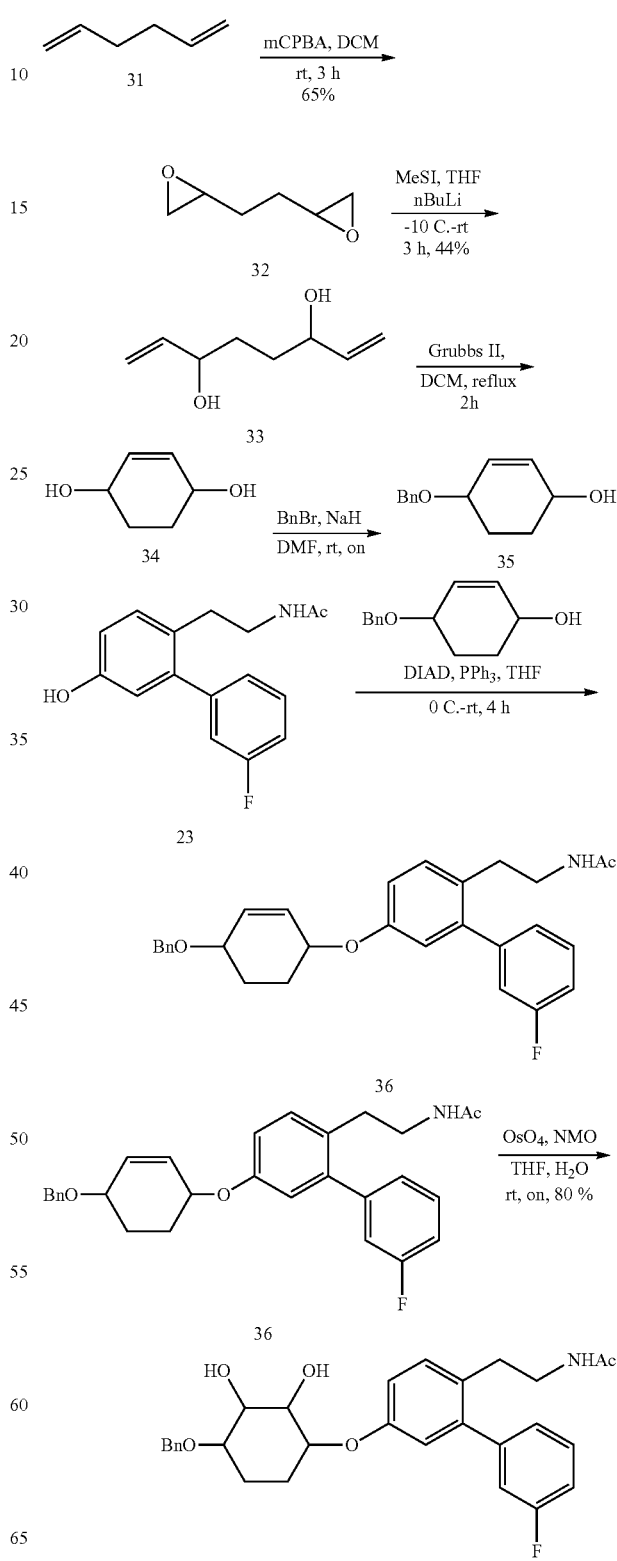

In some embodiments, the disclosure provides compounds of Formula (I) or Formula (IV) wherein $X_3$ is $CH_2$, Z is CH, and $Z_1$ is CH. In some embodiments, the disclosure provides compounds of Formula (I) or Formula (IV) wherein $X_3$ is $CH_2$, and Z—$Z_1$ is —C=C—. For example, Scheme 7 shows a representative synthesis of a compound of Formula (I) or Formula (IV), where $X_3$ is $CH_2$ and or Z-$Z_1$ is —C=C—, In some embodiments, the disclosure provides a compound of Formula (I) or Formula (IV) wherein $X_3$ is $CH_2$ and $R_6$ is alkyl. A representative synthetic route is shown in Scheme 8.

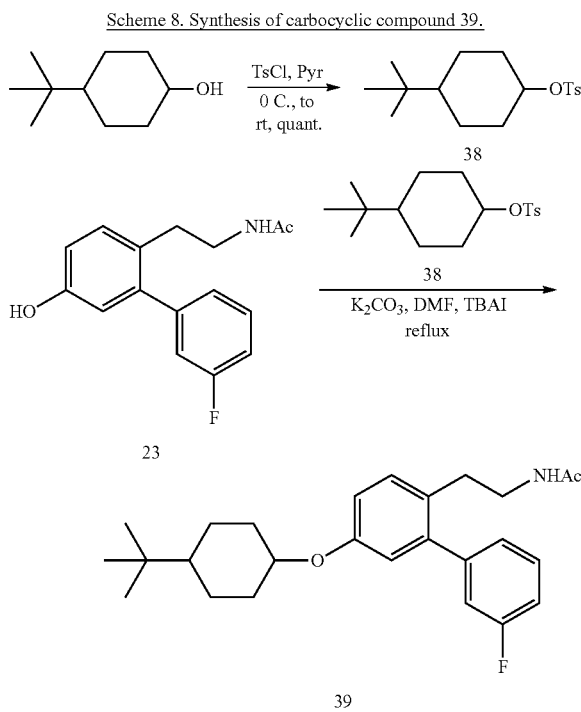

Scheme 8. Synthesis of carbocyclic compound 39.

Evaluation of Neuroprotective Efficacy

Upon synthesis of ethyl acetamide side chain novologues 11a-p that contain various substitutions on the B-ring (hydrogen bond acceptors, hydrogen bond donors, hydrophobic groups, and a tertiary amine), their neuroprotective efficacy against glucose-induced toxicity of embryonic dorsal root ganglion (DRG) sensory neuron cultures was evaluated. As shown in Table 1, meta-substituted acetamide novologues (11b, 11e and 11f) showed significant protection against glucotoxicity and were comparable to that observed with KU-32. Although the corresponding ortho- and para-substituted (11c, 11d and 11g) derivatives showed significant protection against glucose-induced cell death, they were modestly less effective than novologues 11b, 11e and 11f. However in the case of analogues 11i (ortho-OMe) and 11j (meta-OMe) the opposite trend was observed. Electronegative atoms at the meta-position (F, Cl, $CF_3$) exhibited greater cytoprotective activity, which is believed to result from favorable interactions with Lys539 in the Hsp90 C-terminal binding pocket. Consistent with this hypothesis, increasing the size of the electronegative atom at the meta-position (F to Cl to $CF_3$) resulted in a decrease in neuroprotective activity. Similarly, steric bulk was disfavored as well. Analogue 11b (meta-F) was the most cytoprotective (95%±14) compound evaluated.

Electronegative atoms at the ortho- or para-position on ring B (11c, 11d and 11g) manifested activities comparable to the unsubstituted analogue (11a) and were less active than the corresponding meta-substituted analogues (11b, 11e and 11f). Although novologues 11d and 11g manifested protection against neuronal glucotoxicity, they were less effective than KU-32 and 11b. Compound (11m) (para-OH), with hydrogen-bond donor characteristics at the para position of the B-ring, was also somewhat, but not significantly less protective than the unsubstituted analogue (11a).

TABLE 1

Cell viability data of ethyl acetamide side chain novologues.

| Entry | $R_1$ | $R_2$ | $R_3$ | X | Y | % of cell viability [a] |
|---|---|---|---|---|---|---|
| 11a | H | H | H | C | C | 76% ± 11[#] |
| 11b | H | F | H | C | C | 95% ± 14[#] |
| 11c | H | H | F | C | C | 75% ± 27[#] |
| 11d | Cl | H | H | C | C | 71% ± 21[#,*] |
| 11e | H | Cl | H | C | C | 90% ± 23[#] |
| 11f | H | CF3 | H | C | C | 83% ± 16[#] |
| 11g | H | H | CF3 | C | C | 74% ± 19[#,*] |
| 11h | SMe | H | H | C | C | 83% ± 40[#] |
| 11i | OMe | H | H | C | C | 92% ± 10[#] |
| 11j | H | OMe | H | C | C | 78% ± 34[#] |
| 11k | H | Me | H | C | C | 82% ± 30[#] |
| 11l | H | CH2—N-morpholine | H | C | C | 83% ± 26[#] |
| 11m | H | H | OH | C | C | 67% ± 10* |
| 11n | H | —OCH2O— | | C | C | 83% ± 18[#] |
| 11o | H | H | H | N | C | 61% ± 7* |
| 11p | H | H | H | C | N | 81% ± 12[#] |

[a] In the presence of 1 μM of each novologue +20 mM excess glucose. Viability in the presence of 20 mM excess glucose + DMSO was 54% ± 2 and 86% ± 2 in the presence of glucose + 1 μM KU-32.
[#] p < 0.05 versus glucose + DMSO;
*p < 0.05 versus glucose + KU-32 (n = 6-24) per novologue.

On the other hand, hydrogen bond acceptors at the para-position (11c and 11g) protected against glucose-induced neuronal death but did not display significantly increased protection compared to the novologue containing a para-position hydrogen bond donor (11m).

Pyridine-containing analogues (11o-p) were also synthesized and evaluated for neuroprotective activity. The 3-pyridine analogue (11o) was unable to protect against glucose-induce toxicity and was also significantly less protective than the corresponding 4-pyridine analogue, 11p, KU-32, and the unsubstituted phenyl analogue, 11a. Although the 4-pyridine-containing analogue (11p) demonstrated a modestly improved neuroprotective activity when compared to the simple phenyl analogue 11a, this difference in efficacy was not significant.

Neuroprotective activity was also determined for the cyclohexene-containing novologues (20a-b) that contain the fluoro or trifluoromethane substituent at the meta-position of ring B. In general, cyclohexene-containing analogues 20a-b were less efficacious than the corresponding derivatives that contain a flexible side chain (11b versus 20a, and 11f versus 20b). Although not statistically different, novologue 20a (meta-F) exhibited slightly better cytoprotective activity than analogue 20b (meta-CF3), which follows the same trend observed for flexible acetamide-containing compounds (11b versus 11f). Although these data are inconsistent with our hypothesis that accommodation of the hydrophobic pocket would improve efficacy, the cyclohexene ring may exceed the space allowed in this binding cleft.

TABLE 2

Cell viability data of cyclohexene analogues.

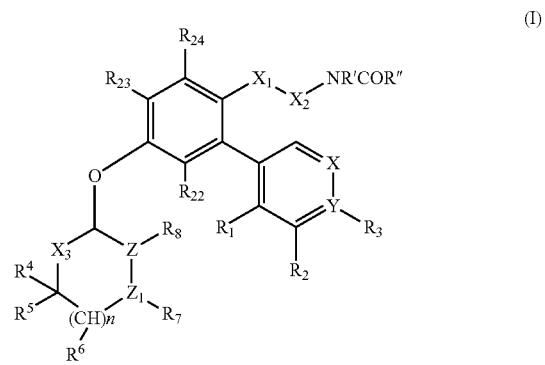

| Entry | $R_2$ | % of cell viability [a] |
|---|---|---|
| 20a | F | 78% ± 18%[#] |
| 20b | CF3 | 69% ± 15%[#,*] |

[a] In the presence of 1 μM novologue + 20 mM excess glucose. Viability in the presence of 20 mM excess glucose + DMSO was 54% ± 2 and 86% ± 2 in the presence of glucose +1 μM KU-32.
[#] $p < 0.05$ versus glucose + DMSO;
[*] $p < 0.05$ versus glucose + KU-32 (n = 8) per novologue.

Figure 4:
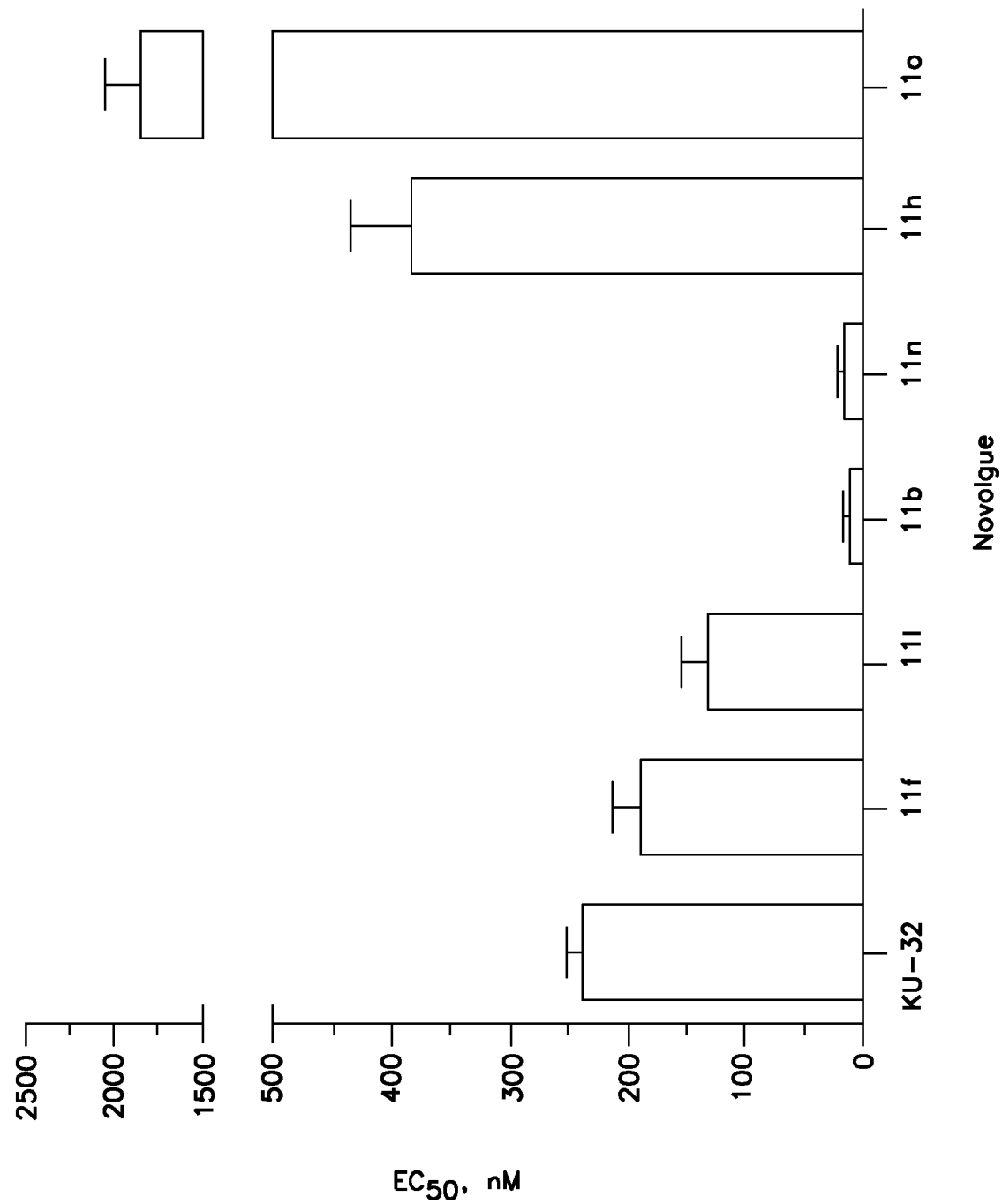
FIG. 4 shows determination of $EC_{50}$ of select novologues KU-32, 11f, 11l, 11b, 11n, 11h, and 11o from FIG. 3. The $EC_{50}$ was determined using the $EC_{anything}$ function of GraphPad Prism 5.0 and the mean±SEM (n=3-8) is shown. #, p<0.05 versus KU-32.

The data in Table 1 clearly support that the majority of novologues synthesized decrease neuronal toxicity induced by hyperglycemic stress. Although some of these compounds appear more effective than KU-32 at 1 μM, the differences were relatively minor. Therefore, to further scrutinize their efficacy, compounds exhibiting high neuroprotective activity were further evaluated for determination of $EC_{50}$ values. Since the difference in efficacy for novologues with meta-F and meta-CF3 substitutions on 11b and 11f were not significantly different from KU-32 or each other at 1 μM, the $EC_{50}$ values for these compounds were determined alongside 11h, 11l, 11n, and 11o. As shown in FIG. 4, $EC_{50}$ values were significantly improved upon closer inspection and clear distinctions were obtained. Novologue 11b exhibited an $EC_{50}$ value (13.0±3.6 nM) that was approximately 14-fold lower than KU-32 (240.2±42.5 nM) or 11f (187.7±43.5 nM). Similar results were also observed for novologue 11n, which exhibited an $EC_{50}$ value of 18.4±3.2 nM. In contrast, novologue 11h which manifested similar efficacy to KU-32 at 1 μM, exhibited an $EC_{50}$ of 384±108 nM, approximately 1.6-fold greater than KU-32.

Figure 5:
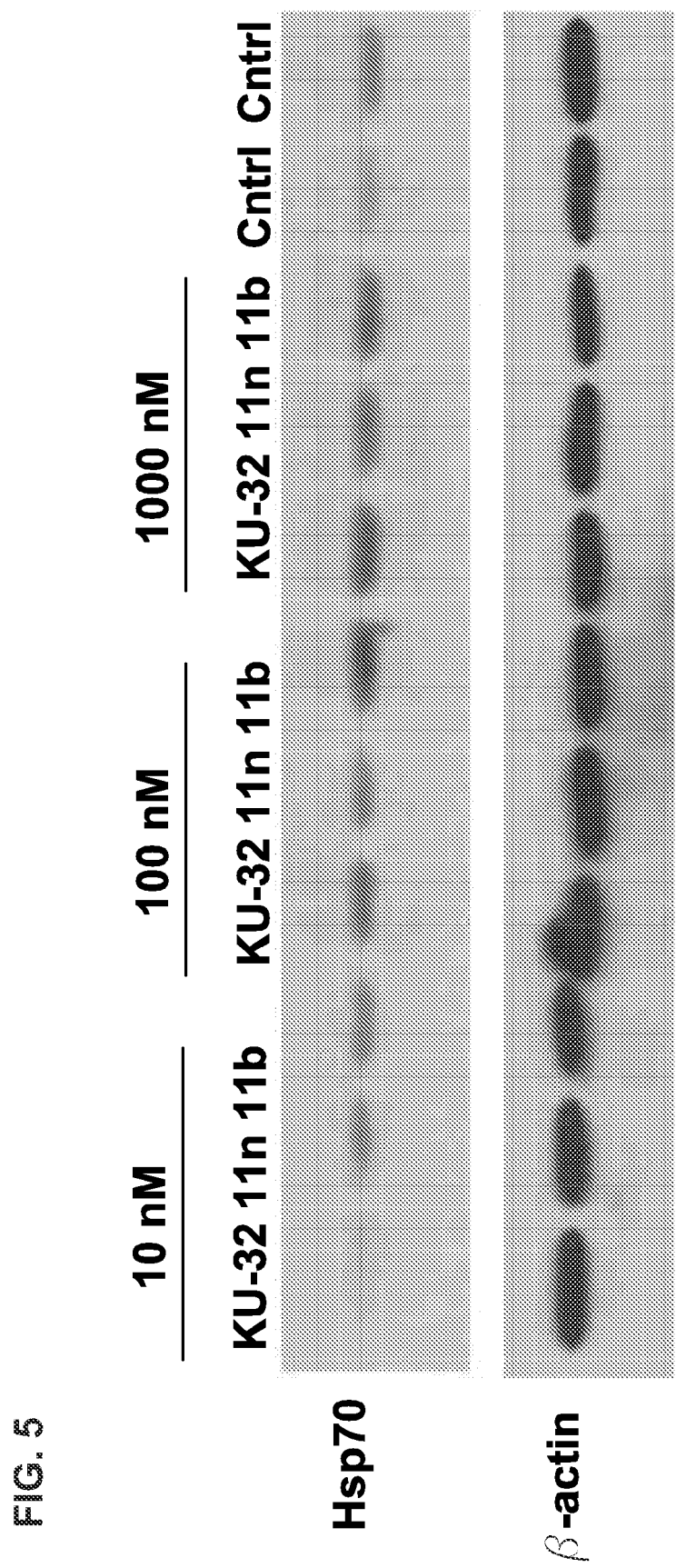
FIG. 5 shows immunoblot analysis of induction of Hsp70 by select novologues KU-32, 11n and 11b. DRG sensory neurons were incubated in the presence of DMSO (Cntrl) or 10-1000 nM of the indicated novologue overnight and then subjected to 4 hrs of hyperglycemia. The neurons were harvested and Hsp70 and β-actin levels were determined by immunoblot analysis. Band intensity was quantified using Image J, Hsp70 expression was normalized to the level of β-actin.

The data in FIG. 4 demonstrate that novologues 11b and 11n are surprisingly more cytoprotective than the initial lead compound, KU-32. Since it was previously shown that the cytoprotective activity manifested by KU-32 requires Hsp70, the ability of 11b and 11n to induce Hsp70 was determined relative to KU-32. Increasing concentrations of KU-32, 11n, and 11b were incubated with DRG sensory neurons for 24 hours before the cells were subjected to 4 hours of glucotoxic stress. Hsp70 levels were examined by performing immunoblot analysis with the cellular lysates (FIG. 5). 11n and 11b induced Hsp70 levels at similar concentrations (10 nM) as those needed for neuroprotection. Although correlative, these data provide a clear link between neuroprotection and the ability of 11b and 11n to induce the heat shock response as exemplified by Hsp70 levels.

Through systematic replacement of substituents on the novologue B-ring (see Table 2), compound 11b was identified as a neuroprotective agent that surprisingly exhibited ~14-fold greater efficacy against glucose-induced toxicity than the lead compound, KU-32. The concentration of 11b needed to manifest neuroprotective activity correlated well with its ability to induce Hsp70 levels, and therefore linking cytoprotection to Hsp70 induction. When combined, these data demonstrate the rationally-designed novologue scaffold provides a promising platform on which diversification of the B-ring can lead to compounds that exhibit better neuroprotective activities.

In one embodiment, the disclosure provides a compound or pharmaceutically acceptable salt according to Formula (I):

$$(I)$$

wherein $R_1$ is hydrogen, hydroxy, halo, trifluoroalkyl, alkyl, alkenyl, alkynyl, carbocyclic, heterocyclic, aryl, aralkyl, carboxyl, amido, amino, alkoxy, halo, trifluoromethyl, sulfanyl, sulfenyl, sulfonyl, or ether;

$R_2$ is hydrogen, halo, hydroxy, trifluoromethyl, alkoxy, alkyl, alkenyl, alkynyl, carbocyclic, alkylcarbocyclic, alkylheterocyclic, heterocyclic, or —$R^9$—$OR^{10}$, wherein $R^9$ is a covalent bond or alkyl, and $R^{10}$ is hydrogen, alkyl, C-amido or acyl; or $R_2$ together with $R_3$ and the atoms to which they are attached form a carbocyclic ring with 5 to 7 ring members or a heterocyclic ring having 4 to 8 ring members with at least one heteroatom selected from oxygen or nitrogen;

$R_3$ is hydrogen, hydroxy, halo, trifluoroalkyl, alkyl, alkoxy, sulfanyl, or —$R^{11}$—O—$R^{12}$, wherein $R^{11}$ is a covalent bond or alkyl, and $R^{12}$ is alkyl, C-amido or acyl; or $R_3$ together with $R_2$ and the atoms to which they are attached form a carbocyclic ring with 5 to 7 ring members or a heterocyclic ring having 4 to 8 ring members with at least one heteroatom selected from oxygen or nitrogen;

$R_4$ is hydrogen, hydroxy, alkyl, arylalkoxy, carboxyl, —$R^{13}$—O—$R^{14}$, or —$R^{13}$—$R^{15}$; and wherein $R^{13}$ is a covalent bond or alkyl, and $R^{14}$ is hydrogen, C-amido or acyl, and $R^{15}$ is N-amido, —$POR^{16}R^{17}$—$SO_2R^{18}$, or sulfonamido, and wherein $R^{16}$, $R^{17}$, $R^{18}$ are independently alkoxy;

$R_5$ is hydrogen, hydroxy, alkyl, arylalkoxy, alkenyl, alkynyl, aryl, or aralkyl;

$R_6$ is hydrogen, hydroxy, sulfanyl, alkyl, alkenyl, alkynyl, aryl, arylalkyl, alkoxy, aryloxy, arylalkoxy or a heterocyclic ring having 4 to 8 ring members with at least one heteroatom selected from oxygen or nitrogen;

$R_7$ is hydrogen, hydroxyl, arylalkoxy, alkyl, acyl, carboxyl or absent;

$R_8$ is hydrogen, hydroxyl, or arylalkoxy;

$R_{22}$ is hydrogen, hydroxy, amino, amido, cyano, alkoxy, halogen, trifluoroalkyl, alkyl, alkenyl, alkynyl, ester, nitro, carboxyl, aralkyl, aryl, carbocyclic, heterocyclic, trifluoromethyl, sulfonyl, sulfanyl, sulfenyl, ether, $R^{25}$—$OR^{26}$, or $R^{25}$—$NR^{26}$; where $R^{25}$ is a covalent bond or alkyl and $R^{26}$ is a hydrogen, alkyl, C-amido, or acyl;

$R_{23}$ is hydrogen, hydroxy, amino, amido, cyano, alkoxy, halogen, trifluoroalkyl, alkyl, alkenyl, alkynyl, ester, nitro, carboxyl, aralkyl, aryl, carbocyclic, heterocyclic, trifluoromethyl, sulfonyl, sulfanyl, sulfenyl, ether, $R^{27}$—$OR^{28}$, or $R^{27}$—$NR^{28}$; where $R^{27}$ is a covalent bond or alkyl and $R^{28}$ is a hydrogen, alkyl, C-amido, or acyl; or $R_{23}$ together with $R_{24}$ and the atoms to which they are attached form a carbocyclic ring with 5 to 7 ring members or a heterocyclic ring having 4 to 8 members with at least one heteroatom selected from oxygen or nitrogen;

$R_{24}$ is hydrogen, hydroxy, amino, amido, cyano, alkoxy, halogen, trifluoroalkyl, alkyl, alkenyl, alkynyl, ester, nitro, carboxyl, aralkyl, aryl, carbocyclic, heterocyclic, trifluoromethyl, sulfonyl, sulfanyl, sulfenyl, ether, $R^{29}$—$OR^{30}$, or $R^{29}$—$NR^{30}$, where $R^{29}$ is a covalent bond or alkyl and $R^{30}$ is a hydrogen, alkyl, C-amido, or acyl; or $R_{24}$ together with $R_{23}$ and the atoms to which they are attached form a carbocyclic ring with 5 to 7 ring members or a heterocyclic ring having 4 to 8 members with at least one heteroatom selected from oxygen or nitrogen;

$X_1$ is —$CHR^{19}$—, or —$CR^{19}$═, and wherein $R^{19}$ is selected from hydrogen, halo, alkyl, alkenyl, or alkynyl; or $X_2$ together with $X_1$ form a carbocyclic ring having 3 to 7 ring members; or wherein $X_1$-$X_2$ is —C≡C—;

$X_2$ is —$CHR^{20}$—, or ═$CR^{20}$—, and wherein $R^{20}$ is selected from hydrogen, halo, alkyl, alkenyl, or alkynyl; or $X_2$ together with $X_1$ form a carbocyclic ring having 3 to 7 ring members; or wherein $X_1$-$X_2$ is —C≡C—;

$X_3$ is O, or $CH_2$;

X is ═$CR^{21}$—, or ═N—, wherein $R^{21}$ is hydrogen, halo, trifluoromethyl, alkyl, alkenyl, alkynyl, alkoxy, or hydroxy;

R' is H, or alkyl;

R" is alkyl, alkoxy, haloalkyl, alkylcycloalkyl or alkylamidoalkyl;

Y is ═$CR_3$— or ═N—;

Z is CH, or Z-$Z_1$ is —C═C—;

$Z_1$ is CH, O, S, N, or Z-$Z_1$ is —C═C—; and n is 0, 1, 2, or 3.

In some embodiments, the disclosure provides compounds of Formula (II):

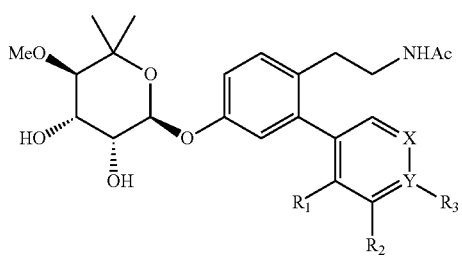

(II)

wherein $R_1$, $R_2$, $R_3$, X and Y are defined as above.

In another embodiment, the disclosure provides a compound or salt of formula (II) wherein $R_1$ is hydrogen, halo, hydroxy, trifluoroalkyl, alkoxy, or sulfanyl;

$R_2$ is hydrogen, halo, hydroxy, trifluoroalkyl, alkoxy, sulfanyl, or alkyl; or $R_2$ together with $R_3$ and the atoms to which they are attached form a carbocyclic ring with 5 to 7 ring members or a heterocyclic ring having 4 to 8 ring members with at least one heteroatom selected from oxygen or nitrogen;

$R_3$ is hydrogen, halo, hydroxy, trifluoroalkyl, alkoxy, sulfanyl, alkyl; or $R_3$ together with $R_2$ and the atoms to which they are attached form a carbocyclic ring with 5 to 7 ring members or a heterocyclic ring having 4 to 8 ring members with at least one heteroatom selected from oxygen or nitrogen;

X is ═$CR^{21}$—, or ═N—, wherein $R^{21}$ is hydrogen, halo, or trifluoromethyl; and Y is ═$CR_3$— or ═N—.

In some embodiments, the disclosure provides compounds of Formula (III), wherein $R_1$, $R_2$, $R_3$, $R_{22}$, $R_{23}$, $R_{24}$, X and Y are defined as above.

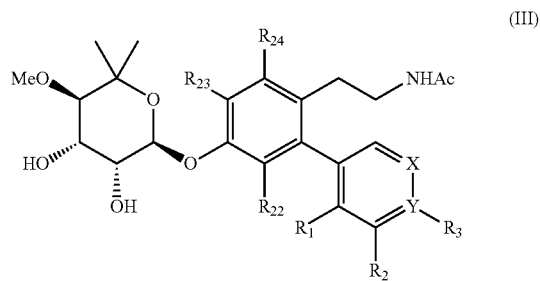

(III)

In some embodiments, the disclosure provides a compound of Formula (III) wherein one of $R_{22}$, $R_{23}$, and $R_{24}$ is not H.

In a specific embodiments, the neuroprotective compound is selected from:

N-(2-(5-(((3R,4S,5R)-3,4-dihydroxy-5-methoxy-6,6-dimethyltetrahydro-2H-pyran-2-yl)oxy)-[1,1'-biphenyl]-2-yl)ethyl)acetamide (11a);

N-(2-(5-(((3R,4S,5R)-3,4-dihydroxy-5-methoxy-6,6-dimethyltetrahydro-2H-pyran-2-yl)oxy)-3'-fluoro-[1,1'-biphenyl]-2-yl)ethyl)acetamide (11b);

N-(2-(5-(((3R,4S,5R)-3,4-dihydroxy-5-methoxy-6,6-dimethyltetrahydro-2H-pyran-2-yl)oxy)-4'-fluoro-[1,1'-biphenyl]-2-yl)ethyl)acetamide (11c);

N-(2-(2'-chloro-5-(((3R,4S,5R)-3,4-dihydroxy-5-methoxy-6,6-dimethyltetrahydro-2H-pyran-2-yl)oxy)-[1,1'-biphenyl]-2-yl)ethyl)acetamide (11d);

N-(2-(3'-chloro-5-(((3R,4S,5R)-3,4-dihydroxy-5-methoxy-6,6-dimethyltetrahydro-2H-pyran-2-yl)oxy)-[1,1'-biphenyl]-2-yl)ethyl)acetamide (11e);

N-(2-(5-(((3R,4S,5R)-3,4-dihydroxy-5-methoxy-6,6-dimethyltetrahydro-2H-pyran-2-yl)oxy)-3'-(trifluoromethyl)-[1,1'-biphenyl]-2-yl)ethyl)acetamide (11f);

N-(2-(5-(((3R,4S,5R)-3,4-dihydroxy-5-methoxy-6,6-dimethyltetrahydro-2H-pyran-2-yl)oxy)-4'-(trifluoromethyl)-[1,1'-biphenyl]-2-yl)ethyl)acetamide (11g);

N-(2-(5-(((3R,4S,5R)-3,4-dihydroxy-5-methoxy-6,6-dimethyltetrahydro-2H-pyran-2-yl)oxy)-2'-(methylthio)-[1,1'-biphenyl]-2-yl)ethyl)acetamide (11h);

N-(2-(5-(((3R,4S,5R)-3,4-dihydroxy-5-methoxy-6,6-dimethyltetrahydro-2H-pyran-2-yl)oxy)-2'-methoxy-[1,1'-biphenyl]-2-yl)ethyl)acetamide (11i);

N-(2-(5-(((3R,4S,5R)-3,4-dihydroxy-5-methoxy-6,6-dimethyltetrahydro-2H-pyran-2-yl)oxy)-3'-methoxy-[1,1'-biphenyl]-2-yl)ethyl)acetamide (11j);

N-(2-(5-(((3R,4S,5R)-3,4-dihydroxy-5-methoxy-6,6-dimethyltetrahydro-2H-pyran-2-yl)oxy)-3'-methyl-[1,1'-biphenyl]-2-yl)ethyl)acetamide (11k);

N-(2-(5-(((3R,4S,5R)-3,4-dihydroxy-5-methoxy-6,6-dimethyltetrahydro-2H-pyran-2-yl)oxy)-3'-(morpholinomethyl)-[1,1'-biphenyl]-2-yl)ethyl)acetamide (11l);

N-(2-(5-(((3R,4S,5R)-3,4-dihydroxy-5-methoxy-6,6-dimethyltetrahydro-2H-pyran-2-yl)oxy)-4'-hydroxy-[1,1'-biphenyl]-2-yl)ethyl)acetamide (11m);

N-(2-(5-(((3R,4S,5R)-3,4-dihydroxy-5-methoxy-6,6-dimethyltetrahydro-2H-pyran-2-yl)oxy)-4'-hydroxy-[1,1'-biphenyl]-2-yl)ethyl)acetamide (11m):

N-(2-(benzo[d][1,3]dioxol-5-yl)-4-(((3R,4S,5R)-3,4-dihydroxy-5-methoxy-6,6-dimethyltetrahydro-2H-pyran-2-yl)oxy)phenethyl)acetamide (11n):

N-(4-(((3R,4S,5R)-3,4-dihydroxy-5-methoxy-6,6-dimethyltetrahydro-2H-pyran-2-yl)oxy)-2-(pyridin-3-yl)phenethyl)acetamide (11o);

N-(4-(((3R,4S,5R)-3,4-dihydroxy-5-methoxy-6,6-dimethyltetrahydro-2H-pyran-2-yl)oxy)-2-(pyridin-4-yl)phenethyl)acetamide (11p);

N-(4'-(((3R,4S,5R)-3,4-dihydroxy-5-methoxy-6,6-dimethyltetrahydro-2H-pyran-2-yl)oxy)-3''-fluoro-1,2,3,6-tetrahydro-[1,1':2',1''-terphenyl]-2-yl)acetamide (20a);

N-(4'-(((3R,4S,5R)-3,4-dihydroxy-5-methoxy-6,6-dimethyltetrahydro-2H-pyran-2-yl)oxy)-3''-(trifluoromethyl)-1,2,3,6-tetrahydro-[1,1':2',1''-terphenyl]-2-yl)acetamide (20b);

N-(2-(5-((4-(benzyloxy)cyclohexyl)oxy)-3'-fluoro-[1,1'-biphenyl]-2-yl)ethyl)acetamide (24);

N-(2-(5-((4-(benzyloxy)cyclohex-2-en-1-yl)oxy)-3'-fluoro-[1,1'-biphenyl]-2-yl)ethyl)acetamide (36);

N-(2-(5-((4-(benzyloxy)-2,3-dihydroxycyclohexyl)oxy)-3'-fluoro-[1,1'-biphenyl]-2-yl)ethyl)acetamide (37);

N-(2-(5-((4-(tert-butyl)cyclohexyl)oxy)-3'-fluoro-[1,1'-biphenyl]-2-yl)ethyl)acetamide (39);

N-(2-(3'-fluoro-5-((4-(piperidin-4-yl)cyclohexyl)oxy)-[1,1'-biphenyl]-2-yl)ethyl)acetamide (40);

N-(2-(5-(((3R,4S,5R)-3,4-dihydroxy-5-methoxy-6,6-dimethyltetrahydro-2H-pyran-2-yl)oxy)-3'-fluoro-6-hydroxy-[1,1'-biphenyl]-2-yl)ethyl)acetamide (41);

N-(2-(5-(((3R,4S,5R)-3,4-dihydroxy-5-methoxy-6,6-dimethyltetrahydro-2H-pyran-2-yl)oxy)-3'-fluoro-3-methoxy-[1,1'-biphenyl]-2-yl)ethyl)acetamide (42); and N-(2-(5-(((3R,4S,5R)-3,4-dihydroxy-5-methoxy-6,6-dimethyltetrahydro-2H-pyran-2-yl)oxy)-3'-fluoro-4-methyl-[1,1'-biphenyl]-2-yl)ethyl)acetamide (43).

Several of the compounds of the present invention have been shown to inhibit Hsp90 in vitro. As such, it is contemplated that therapeutically effective amounts of the compounds of the present invention will be useful as neuroprotective agents that result in at least a 10% enhancement of cell viability compared to control over a given time period and under certain conditions, for example, such as glucose-induced toxicity in vitro or under a diabetic condition in vivo.

In the context of neuroprotection, it is contemplated that some of the compounds of the present invention may be used with other Hsp90 inhibitors and/or neuroprotective agents.

The following examples are provided to illustrate the present invention and are not intended to limit the scope thereof. Those skilled in the art will readily understand that known variations of the conditions and processes of the following preparative procedures can be used to prepare these compounds.

The present invention is directed to the use of therapeutically effective amount of one or more of the compounds disclosed herein to treat and/or prevent a neurodegenerative disorder such as diabetic peripheral neuropathy and/or to provide neuroprotection.

Compositions of the Present Invention

According to another aspect, the present invention provides a pharmaceutical composition, which comprises a therapeutically-effective amount of one or more compounds of the present invention or a pharmaceutically-acceptable salt, ester or prodrug thereof, together with a pharmaceutically-acceptable diluent or carrier. The pharmaceutical compositions provide neuroprotection and used to treat and/or prevent neurodegenerative disorders.

The compositions may be formulated for any route of administration, in particular for oral, rectal, transdermal, subcutaneous, intravenous, intramuscular, or intranasal administration. The compositions may be formulated in any conventional form, for example, as tablets, capsules, caplets, solutions, suspensions, dispersions, syrups, sprays, gels, suppositories, patches, and emulsions.

Accordingly, the compounds of the present invention are useful in the treatment or alleviation of neurodegenerative disorders, such as Alzheimer's disease, Parkinson's disease, Lou Gehrig's disease, or multiple sclerosis, to name a few, not to mention central or peripheral nervous system damage, dysfunction, or complications involving same stemming from edema, injury, or trauma. Such damage, dysfunction, or complications may be characterized by an apparent neurological, neurodegenerative, physiological, psychological, or behavioral aberrations, the symptoms of which can be reduced by the administration of a therapeutically effective amount of the compounds of the present invention.

The following examples are provided for further illustration of the present invention, and do not limit the invention.

EXAMPLES

Example 1

Preparation of Embryonic Dorsal Root Ganglion (DRG) Neuron Cultures

DRG from embryonic day 15-18 Sprague Dawley rat pups were harvested into Leibovitz's L15 medium (L15) and dissociated with 0.25% trypsin for 30 min at 37° C. The ganglia were sedimented at 1,000×g for 5 min, resuspended in growth media [phenol red free Neurobasal medium (Gibco, Grand Island, N.Y.) containing 25 mM glucose, 1×B-27 additive, 50 ng/ml NGF (Harlan Bioscience, Indianapolis, Ind.), 4 mM glutamine, 100 U/mL penicillin and 100 µg/mL streptomycin] and triturated with a fire-polished glass pipette. The cells were cultured on collagen-coated (0.1 mg/mL collagen followed by overnight air drying in a laminar flow hood) black-walled 96-well plates (Corning Incorporated Corning, N.Y.) at a seeding density of $2-3 \times 10^4$ cells per well. DRG neurons were re-fed the next day with fresh growth media containing 40 µM fluorodeoxyuridine and 10 µM cytosine β-D-arabinoside (both from Sigma Aldrich, St. Louis, Mo.) for 2 days to remove proliferating cells. Experiments were performed on DRG neurons on the third day in culture after placing the cells in fresh growth medium.

Example 2

Glucotoxicity Assay

Immature DRG are susceptible to hyperglycemia-induced death. Vincent, A. M.; Kato, K.; McLean, L. L.; Soules, M. E.; Feldman, E. L., Sensory Neurons and Schwann Cells Respond to Oxidative Stress by Increasing Antioxidant Defense Mechanisms. *Antioxid Redox Signal* 2009, 11, 425-438. Therefore, an additional 20 mM glucose was added to the growth medium of Example 1 (yielding a total of 45 mM glucose) for 4 hours. Preliminary experiments found that 20 mM excess glucose for 4 hrs was sufficient to induce a reproducible 40-50% loss in neuronal viability. As a result, the toxicity induced by the acute change in glucose concentration makes it a useful model for drug screening. Urban, M. J.; Li, C.; Yu, C.; Lu, Y.; Krise, J. M.; McIntosh, M. P.; Rajewski, R. A.; Blagg, B. S. J.; Dobrowsky, R. T., Inhibiting Heat Shock Protein 90 Reverses Sensory Hypoalgesia in Diabetic Mice. *ASN Neuro* 2010, 2, e00040 DOI:189-199; Vincent, A. M.; Stevens, M. J.; Backus, C.; McLean, L. L.; Feldman, E. L., Cell culture modeling to test therapies against hyperglycemia-mediated oxidative stress and injury. *Antioxid Redox Signal* 2005, 7 (11-12), 1494-506.

Given the short time frame that the neurons are grown in vitro, they are not pure neuronal cultures but instead, highly enriched. Importantly, the contaminating SCs that remain in the culture are resistant to glucose-induced death as we and others have reported previously. Vincent, A. M.; Kato, K.; McLean, L. L.; Soules, M. E.; Feldman, E. L., Sensory Neurons and Schwann Cells Respond to Oxidative Stress by Increasing Antioxidant Defense Mechanisms. *Antioxid Redox Signal* 2009, 11, 425-438; Zhang, L.; Yu, C.; Vasquez, F. E.; Galeva, N.; Onyango, I.; Swerdlow, R. H.; Dobrowsky, R. T., Hyperglycemia alters the schwann cell mitochondrial proteome and decreases coupled respiration in the absence of superoxide production. *J Proteome Res* 2010, 9 (1), 458-71.

Unfortunately, the use of highly purified cultures is problematic since the cells extend neurites and establish connections with each other, thus becoming resistant to hyperglycemia-induced death. Yu, C.; Rouen, S.; Dobrowsky, R. T., Hyperglycemia and downregulation of caveolin-1 enhance neuregulin-induced demyelination. *Glia* 2008, 56, 877-887.

DRG neurons were incubated overnight with the test compounds in the presence of Neurobasal medium, 50 ng/ml NGF and antibiotics only. In order to monitor the efficiency of the compounds in protecting DRG neurons against glucotoxicity, Calcein AM (Invitrogen, Carlsbad, Calif.) was utilized to measure cell viability. Hydrolysis of calcein AM to a fluorescent product can only occur in live cells. Excess glucose was added to the cultures for 4 hrs and cell viability was measured by incubating the cells with 2 calcein AM for 30 min in the dark at 37° C. Fluorescence was then measured using a plate reader with excitation and emission wavelengths set to 485 nm and 520 nm, respectively. The arbitrary fluorescence readings were normalized to the total amount of protein from each respective well of the neuronal cultures. The protein concentrations in each well were determined using the DC protein assay (Bio-Rad). Significant differences in the efficacy of the novologues for increasing cell viability were determined using a Kruskal-Wallis non-parametric ANOVA and Dunn's post-test.

Example 3

Chemistry General—NMR $^1$H NMR were recorded at 400 or 500 MHz (Bruker DRX-400 Bruker with a H/C/P/F QNP gradient probe) spectrometer and $^{13}$C NMR spectra were recorded at 125 MHz (Bruker DRX 500 with broadband, inverse triple resonance, and high resolution magic angle spinning HR-MA probe spectrometer); chemical shifts are reported in δ (ppm) relative to the internal reference chloroform-d (CDCl$_3$, 7.27 ppm).

Example 4

Chemistry General—Mass Spectroscopy and HPLC

FAB (HRMS) spectra were recorded with a LCT Premier (Waters Corp., Milford, Mass.).

The purity of all compounds was determined to be >95% as determined by $^1$H NMR and $^{13}$C NMR spectra, unless otherwise noted. The most active 5 compounds were verified for >95% purity by HPLC analyses. TLC was performed on glass backed silica gel plates (Uniplate) with spots visualized by UV light. All solvents were reagent grade and, when necessary, were purified and dried by standard methods. Concentration of solutions after reactions and extractions involved the use of a rotary evaporator operating at reduced pressure.

Example 5

Synthesis of 5-(benzyloxy)-2-formylphenyl trifluoromethanesulfonate (3)

A solution of phenol 2 (11.2 g, mmol) in anhydrous DCM (245 mL) was stirred at 0° C. and triethylamine (10.2 mL, 73.5 mmol) was added followed by triflic anhydride (13.8 mL, 63.5 mmol) over 5 minutes. Upon completion the reaction was quenched by addition of water (50 mL), washed with saturated aqueous NaCl solution, dried (Na$_2$SO$_4$), filtered and concentrated. The residue was purified by column chromatography (SiO$_2$, 4:1, Hex:EtOAc) to afford triflate 3 as a yellow oil (8.4g, 23.6 mmol, 48%). Immediately used in Suzuki coupling reactions.

Example 6

General Procedure for Suzuki Coupling Reaction of Triflate 3 and Boronic Acids 2a-p 5-(benzyloxy)-[1,1'-biphenyl]-2-carbaldehyde (6a)

Triflate 5 (0.246 g, 0.68 mmol), phenylboronic acid 2a (92 mg, 0.75 mmol), tetrakis(triphenylphosphine)palladium(0) (70.4 mg, 0.068 mmol) and K$_2$CO$_3$ (0.169 g, 1.2 mmol) was dissolved in DMF (6.8 mL) under argon atmosphere in a sealed tube. The resulting reaction mixture was sealed and heated to reflux for 16 h. The reaction was cooled to RT, quenched with saturated sodium bicarbonate, extracted with EtOAc (3×5 mL), washed with saturated aqueous sodium chloride, dried over anhydrous Na$_2$SO$_4$, filtered and concentrated. The crude product was purified by column chromatography (SiO$_2$, 3:1, Hex:EtOAc) to afford 6a (0.16 g, 0.56 mmol, 82%) as an amorphous solid. $^1$H NMR (400 MHz, CDCl$_3$) δ 9.90 (s, 1H), 8.08 (d, J=8.7 Hz, 1H), 7.55-7.34 (m, 10H), 7.11 (d, J=8.7 Hz, 1H), 7.03 (d, J=2.4 Hz, 1H), 5.19 (s, 2H); $^{13}$C NMR (100 MHz, CDCl$_3$) δ 191.2, 162.8, 148.6, 137.8, 136.0, 130.0, 128.8, 128.4, 127.6, 116.3, 114.7, 70.4; HRMS (FAB) m/z: [M+Na$^+$] for C$_{20}$H$_{16}$O$_2$Na, calcd, 311.1042. found, 311.1046.

5-(benzyloxy)-3'-fluoro-[1,1'-biphenyl]-2-carbaldehyde (6b)

Using 3-flourophenylboronic acid. $^1$H NMR (500 MHz, CDCl$_3$) δ 9.85 (d, J=0.7 Hz, 1H), 8.03 (d, J=8.7 Hz, 1H), 7.49-7.33 (m, 6H), 7.20-7.13 (m, 2H), 7.13-7.08 (m, 2H), 7.03 (d, J=2.5 Hz, 1H), 5.15 (s, 2H); $^{13}$C NMR (125 MHz, CDCl$_3$) δ 190.7, 162.9, 161.7, 147.2, 140.1, 136.0, 130.5, 129.0, 128.6, 127.8, 126.0, 117.1, 116.9, 116.4, 115.5, 115.1, 70.6; HRMS m/z: [M+Na$^+$] for C$_{20}$H$_{15}$FO$_2$Na, calcd, 329.0948. found, 329.0952.

5-(benzyloxy)-4'-fluoro-[1,1'-biphenyl]-2-carbaldehyde (6c)

Using 4-Flourophenylboronic acid. $^1$H NMR (400 MHz, CDCl$_3$) δ 9.84 (s, 1H), 8.06 (dd, J=8.7, 1.0 Hz, 1H), 7.49-7.40

(m, 4H), 7.40-7.32 (m, 3H), 7.21-7.13 (m, 2H), 7.12-7.06 (dd, J=8.0, 2.5 Hz, 1H), 7.03 (d, J=2.2 Hz, 1H), 5.17 (s, 2H); $^{13}$C NMR (100 MHz, CDCl$_3$) δ 190.9, 162.8, 147.4, 136.0, 131.7, 131.6, 130.5, 128.8, 128.5, 127.7, 127.6, 116.5, 115.6, 115.4, 114.7, 70.4; HRMS m/z: [M+Na$^+$] for C$_{20}$H$_{15}$FO$_2$Na, calcd, 329.0948. found, 329.0944.

5-(benzyloxy)-2'-chloro-[1,1'-biphenyl]-2-carbaldehyde (6d)

Using 2-Chlorophenylboronic acid. $^1$H NMR (500 MHz, CDCl$_3$) δ 9.70 (s, 1H), 8.08 (d, J=8.7 Hz, 1H), 7.55-7.49 (m, 1H), 7.49-7.32 (m, 8H), 7.17-7.12 (dd, J=8.6, 2.5 Hz, 1H), 6.99 (d, J=2.6 Hz, 1H), 5.16 (s, 2H); $^{13}$C NMR (125 MHz, CDCl$_3$) δ 190.3, 162.9, 145.1, 136.8, 135.9, 133.5, 131.6, 130.0, 129.8, 129.6, 128.8, 128.4, 127.6, 127.6, 126.9, 116.7, 115.1, 70.4; HRMS m/z: [M+Na$^+$] or C$_{20}$H$_{15}$ClO$_2$Na, calcd, 345.0658. found, 345.0653.

5-(benzyloxy)-3'-chloro-[1,1'-biphenyl]-2-carbaldehyde (6e)

Using 3-Chlorophenylboronic acid. $^1$H NMR (400 MHz, CDCl$_3$) δ 9.85 (s, 1H), 8.04 (d, J=8.7 Hz, 1H), 7.49-7.33 (m, 8H), 7.26 (m, 1H), 7.13-7.07 (dd, J=8.3, 2.8 Hz, 1H), 6.96 (d, J=2.5 Hz, 1H), 5.17 (s, 2H); $^{13}$C NMR (100 MHz, CDCl$_3$) δ 190.4, 162.8, 146.8, 139.7, 135.9, 134.5, 130.5, 129.8, 129.7, 128.8, 128.5, 128.4, 128.3, 127.6, 127.5, 116.3, 115.0, 70.4; HRMS m/z: [M+Cl$^-$] for C$_{20}$H$_{15}$Cl$_2$O$_2$, calcd, 341.0505. found, 341.0508.

5-(benzyloxy)-3'-(trifluoromethyl)-[1,1'-biphenyl]-2-carbaldehyde (6f)

Using 3-(Trifluoromethyl)phenylboronic acid. $^1$H NMR (400 MHz, CDCl$_3$) δ 9.82 (s, 1H), 8.05 (m, 1H), 7.72 (m, 1H), 7.67-7.64 (td, J=1.6, 0.8 Hz, 1H), 7.64-7.53 (m, 2H), 7.50-7.35 (m, 5H), 7.15-7.11 (dd, J=8.7, 2.2 Hz, 1H), 6.96 (d, J=2.5 Hz, 1H), 5.19 (s, 2H); $^{13}$C NMR (100 MHz, CDCl$_3$) δ 190.4, 163.0, 146.8, 138.8, 135.9, 133.4, 131.0, 130.9, 129.0, 129.0, 128.6, 127.8, 127.6, 126.6, 126.5, 125.2, 116.7, 115.2, 70.6; HRMS m/z: [M+Na$^+$] for C$_{21}$H$_{15}$F$_3$O$_2$Na, calcd, 379.0922. found, 379.0926.

5-(benzyloxy)-4'-(trifluoromethyl)-[1,1'-biphenyl]-2-carbaldehyde (6g)

Using 4-(Trifluoromethyl)phenylboronic acid. $^1$H NMR (400 MHz, CDCl$_3$) δ 9.84 (s, 1H), 8.06 (d, J=8.7 Hz, 1H), 7.75 (d, J=8.0 Hz, 2H), 7.55-7.49 (m, 2H), 7.49-7.34 (m, 6H), 7.17-7.12 (dd, J=9.1, 2.2 Hz, 1H), 6.98 (d, J=2.5 Hz, 1H), 5.19 (s, 2H); $^{13}$C NMR (100 MHz, CDCl$_3$) δ 190.2, 162.9, 146.7, 141.7, 135.9, 130.8, 130.3, 128.9, 128.6, 127.7, 127.5, 125.5, 125.4, 122.8, 116.6, 115.1, 70.5; HRMS m/z: [M+H$^+$] for C$_{21}$H$_{16}$F$_3$O$_2$, calcd, 357.1097. found, 357.1096.

5-(benzyloxy)-2'-(methylthio)-[1,1'-biphenyl]-2-carbaldehyde (6h)

Using 2-(Methylthio)phenylboronic acid. $^1$H NMR (400 MHz, CDCl$_3$) δ 9.62 (s, 1H), 8.05 (d, J=8.7 Hz, 1H), 7.47-7.32 (m, 6H), 7.30-7.23 (m, 2H), 7.24-7.20 (m, 1H), 7.13-7.09 (m, 1H), 6.93-6.90 (m, 1H), 5.17 (s, 2H), 2.36 (d, J=1.1 Hz, 3H); $^{13}$C NMR (100 MHz, CDCl$_3$) δ 190.8, 163., 146.3, 138.4, 136.2, 136.1, 130.4, 129.5, 129.1, 128.8, 128.4, 127.8, 127.7, 124.7, 124.6, 116.4, 115.3, 70.4, 15.6; HRMS m/z: [M+H$^+$] for C$_{21}$H$_{18}$O$_2$SNa, calcd, 357.0920. found, 357.0923.

5-(benzyloxy)-2'-methoxy-[1,1'-biphenyl]-2-carbaldehyde (6i)

Using 2-Methoxyphenylboronic acid. $^1$H NMR (500 MHz, CDCl$_3$) δ 9.73 (s, 1H), 8.07 (d, J=8.7 Hz, 1H), 7.48-7.39 (m, 5H), 7.37 (d, J=6.5 Hz, 1H), 7.32-7.27 (m, 1H), 7.13-7.07 (m, 2H), 7.02 (d, J=8.3 Hz, 1H), 6.98-6.95 (dd, J=2.4, 1.1 Hz, 1H), 5.15 (s, 2H), 3.75 (s, 3H); $^{13}$C NMR (125 MHz, CDCl$_3$) δ 191.5, 163.1, 156.6, 144.5, 136.2, 131.4, 130.1, 129.2, 128.8, 128.4, 127.9, 127.7, 126.8, 121.0, 116.9, 114.5, 110.8, 70.3, 55.5; HRMS m/z: [M+H$^+$] for C$_{21}$H$_{19}$O$_3$, calcd, 319.1329. found, 319.1333.

5-(benzyloxy)-3'-methoxy-[1,1'-biphenyl]-2-carbaldehyde (6j)

Using 3-Methoxyphenylboronic acid. $^1$H NMR (400 MHz, CDCl$_3$) δ 9.93 (s, 1H), 8.06 (d, J=9.0 Hz, 1H), 7.52-7.35 (m, 6H), 7.10 (d, J=8.6 Hz, 1H), 7.05-6.93 (m, 4H), 5.20 (s, 2H), 3.89 (s, 3H); HRMS m/z: [M+Na$^+$] for C$_{21}$H$_{18}$O$_3$Na, calcd, 341.1154. found, 341.1150.

5-(benzyloxy)-3'-methyl-[1,1'-biphenyl]-2-carbaldehyde (6k)

Using 3-Methylphenylboronic acid. $^1$H NMR (500 MHz, CDCl$_3$) δ 9.85 (d, J=0.9 Hz, 1H), 8.03 (d, J=8.6 Hz, 1H), 7.49-7.39 (m, 3H), 7.39-7.32 (m, 2H), 7.27 (d, J=8.1 Hz, 1H), 7.22-7.16 (m, 2H), 7.09-7.05 (ddd, J=8.8, 2.6, 0.9 Hz, 1H), 6.98 (d, J=2.5 Hz, 1H), 5.15 (s, 2H), 2.43 (s, 3H); $^{13}$C NMR (125 MHz, CDCl$_3$) δ 191.4, 162.8, 148.9, 138.3, 137.9, 136.2, 130.9, 130.1, 129.2, 128.9, 128.5, 128.5, 127.8, 127.3, 116.3, 114.8, 70.5, 21.7; HRMS m/z: [M+H$^+$] for C$_{21}$H$_{18}$O$_2$Na, calcd, 325.1205. found, 325.1217.

5-(benzyloxy)-3'-(morpholinomethyl)-[1,1'-biphenyl]-2-carbaldehyde (6l)

Using 3-(4-Morpholinomethyl)phenylboronic acid pinacol ester. $^1$H NMR (400 MHz, CDCl$_3$) δ 9.87 (s, 1H), 8.83 (d, J=8.7 Hz, 1H), 7.47-7.31 (m, 7H), 7.32-7.24 (m, 1H), 7.12-7.04 (dd, J=8.7, 2.5 Hz, 1H), 7.05 (d, J=2.5 Hz, 1H), 5.17 (s, 2H), 3.79-3.68 (t, J=4.6 Hz, 4H), 3.56 (s, 3H), 2.49 (d, J=6.5 Hz, 4H); $^{13}$C NMR (100 MHz, CDCl$_3$) δ 191.0, 162.7, 148.5, 138.3, 137.8, 136.0, 130.7, 130.2, 129.1, 128.8, 128.4, 127.6, 127.6, 116.4, 114.5, 70.4, 67.1, 63.2, 53.7; HRMS m/z: [M+Na$^+$] for C$_{25}$H$_{25}$NO$_3$Na, calcd, 410.1726. found, 410.1730.

5-(benzyloxy)-4'-hydroxy-[1,1'-biphenyl]-2-carbaldehyde (6m)

Used 4-Hydroxyphenylboronic acid.
Partially purified biaryl phenol was treated with TBSCl (1.2 eq.) and imidazole (3 eq.) in DCM and stirred for 2 h at RT. After reaction was completed by TLC, the resulting reaction mixture was concentrated. The crude product was purified by column chromatography (SiO$_2$, 4:1, Hex:EtOAc) to afford 6m (94%) as an amorphous solid. $^1$H NMR (500 MHz, CDCl$_3$) δ 9.89 (s, 1H), 8.03 (d, J=8.7 Hz, 1H), 7.52-7.33 (m, 5H), 7.26 (dd, J=6.6, 1.8 Hz, 2H), 7.05 (dd, J=8.7, 2.3 Hz, 1H), 7.02-6.93 (m, 3H), 5.17 (s, 2H), 1.05 (s, 9H), 0.29 (s, 6H); $^{13}$C NMR (125 MHz, CDCl$_3$) δ 191.2, 162.7, 156.0, 148.4, 136.1, 131.2, 130.6, 130.0, 128.7, 128.3, 127.6, 127.5, 120.0, 116.1, 114.3, 70.3, 25.7, 18.3, 4.3; ESI-HRMS m/z: [M+Na]$^+$ for $C_{26}H_{30}NaO_3Si$, calcd, 441.5899. found 441.5896.

2-(benzo[d][1,3]dioxol-5-yl)-4-(benzyloxy)benzaldehyde (6n)

Using 3,4-(Methylenedioxy)phenylboronic acid. $^1$H NMR (500 MHz, CDCl$_3$) δ 9.90 (s, 1H), 8.08 (d, J=8.7 Hz, 1H), 7.48-7.39 (m, 4H), 7.39-7.35 (m, 1H), 7.06 (d, J=8.6 Hz, 1H), 6.97 (d, J=2.5 Hz, 1H), 6.91-6.86 (m, 2H), 6.83-6.79 (m, 1H), 6.03 (s, 2H), 5.15 (s, 2H); $^{13}$C NMR (125 MHz, CDCl$_3$) δ 191.2, 162.8, 148.2, 147.9, 147.9, 136.1, 131.6, 130.2, 128.8, 128.4, 127.7, 127.6, 124.0, 116.2, 114.5, 110.3, 108.3, 101.5, 70.4; HRMS (FAB) m/z: [M+Na]$^+$ for $C_{21}H_{16}O_4Na$, calcd, 355.0941. found, 355.0935.

4-(benzyloxy)-2-(pyridin-3-yl)benzaldehyde (6o)

$^1$H NMR (400 MHz, CDCl3) δ 9.79 (s, 1H), 8.65 (dd, 2H, J=5.1, 8.3 Hz), 8.01 (d, 1H, J=8.8 Hz), 7.67 (m, 1H), 7.48-7.26 (m, 6H), 7.09 (dd, 1H, J=2.4, 8.7 Hz), 6.93 (d, 1H, J=2.4 Hz), 5.14 (s, 2H); $^{13}$C NMR (125 MHz, CDCl$_3$) δ 187.8, 165.3, 160.5, 135.8, 131.2, 129.0, 128.7, 127.8, 120.0, 109.5, 102.1, 91.0, 70.8; HRMS (FAB) m/z: [M+H]$^+$ for $C_{19}H_{16}NO_2$, calcd, 290.1181. found, 290.1177.

4-(benzyloxy)-2-(pyridin-4-yl)benzaldehyde (6p)

$^1$H NMR (500 MHz, CDCl$_3$) δ 9.82 (s, 1H), 8.67 (d, J=5.9 Hz, 2H), 8.02 (d, J=8.7 Hz, 1H), 7.49-7.33 (m, 6H), 7.30 (d, J=6.0 Hz, 1H), 7.15-7.10 (dd, J=8.6, 2.6 Hz, 1H), 6.95 (d, J=2.6 Hz, 1H), 5.15 (s, 2H); $^{13}$C NMR (125 MHz, CDCl$_3$) δ 189.7, 162.9, 149.8, 145.8, 145.2, 135.7, 131.0, 128.8, 128.5, 127.6, 127.1, 124.6, 116.3, 115.4, 70.5; HRMS (FAB) m/z: [M+H]$^+$ for $C_{19}H_{16}NO_2$, calcd, 290.1181. found, 290.1183.

Example 7

General Procedure for Henry Reaction of Compounds 6a-p

(E)-5-(benzyloxy)-2-(2-nitrovinyl)-1,1'-biphenyl (7a)

Nitromethane (1.4 mL) was added to a mixture of aldehyde 6a (0.16g, 0.56 mmol) and ammonium acetate (77 mg, 1.0 mmol) and heated to 50° C. Upon completion (~15-30 min), the reaction mixture was cooled to RT and purified without work-up by column chromatography (SiO$_2$, 3:1, Hex:EtOAc) to afford nitrostyrene 7a as a yellow oil (182 mg, 0.55 mmol, 98%). $^1$H NMR (400 MHz, CDCl$_3$) δ 8.02 (d, J=13.6 Hz, 1H), 7.64 (d, J=9.5 Hz, 1H), 7.50-7.35 (m, 10H), 7.31 (d, J=2.1 Hz, 2H), 7.04 (d, J=2.5 Hz, 1H), 5.15 (s, 2H); $^{13}$C NMR (100 MHz, CDCl$_3$) δ 161.8, 146.1, 138.1, 136.4, 136.3, 135.5, 131.8 131.7, 129.9, 129.2, 128.8, 128.0, 121.3, 117.3, 116.3, 116.0, 115.6, 70.7; HRMS (FAB) m/z: [M+Na]$^+$ for $C_{21}H_{18}NO_3$, calcd, 332.1281. found, 332.1290.

(E)-5-(benzyloxy)-3'-fluoro-2-(2-nitrovinyl)-1,1'-biphenyl (7b)

$^1$H NMR (400 MHz, CDCl$_3$) δ 8.07 (d, J=13.5 Hz, 1H), 7.65 (d, J=8.7 Hz, 1H), 7.49-7.35 (m, 7H), 7.20-7.13 (ddd, J=9.3, 7.9, 2.6 Hz, 1H), 7.09-7.03 (m, 2H), 7.02 (d, J=2.8 Hz, 2H), 5.16 (s, 2H); $^{13}$C NMR (100 MHz, CDCl$_3$) δ 164.0, 161.5, 145.4, 141.4, 137.6, 136.1, 136.0, 130.5, 130.4, 129.6, 128.6, 127.7, 125.7, 121.0, 116.9, 116.6, 115.6, 115.4, 70.5; HRMS m/z: [M+H]$^+$ for $C_{21}H_{17}FNO_3$, calcd, 350.1187. found, 350.1185.

(E)-5-(benzyloxy)-4'-fluoro-2-(2-nitrovinyl)-1,1'-biphenyl (7c)

$^1$H NMR (400 MHz, CDCl$_3$) δ 8.08 (d, J=13.6 Hz, 1H), 7.64 (d, J=8.7 Hz, 1H), 7.50-7.34 (m, 6H), 7.32-7.24 (m, 2H), 7.23-7.14 (t, J=8.3 Hz, 2H), 7.10-7.00 (m, 2H), 5.17 (s, 2H); $^{13}$C NMR (100 MHz, CDCl$_3$) δ 161.5, 145.7, 137.8, 136.1, 136.0, 131.5, 131.4, 129.6, 128.9, 128.5, 127.7, 121.0, 117.0, 115.9, 115.7, 115.3, 70.4; HRMS m/z: [M+Na$^+$] for $C_{21}H_{16}FNO_3Na$, calcd, 372.1006. found, 372.1011.

(E)-5-(benzyloxy)-2'-chloro-2-(2-nitrovinyl)-1,1'-biphenyl (7d)

$^1$H NMR (500 MHz, CDCl$_3$) δ 7.85-7.75 (m, 1H), 7.74-7.66 (m, 1H), 7.55 (m, 1H), 7.53-7.34 (m, 8H), 7.31 (d, J=5.3 Hz, 1H), 7.17 (d, J=8.3 Hz, 1H), 7.01 (t, J=2.0 Hz, 1H), 5.20-5.11 (m, 2H); $^{13}$C NMR (125 MHz, CDCl$_3$) δ 161.4, 143.8, 137.7, 137.0, 135.9, 133.2, 131.4, 130.0, 130.0, 129.3, 128.7, 128.3, 127.6, 127.1, 123.4, 121.5, 117.1, 115.6, 70.3; HRMS m/z: [M+H$^+$] for $C_{21}H_{17}ClNO_3$, calcd, 366.0892. found, 366.0895.

5-(benzyloxy)-3'-chloro-2-(2-nitrovinyl)-1,1'-biphenyl (7e)

$^1$H NMR (400 MHz, CDCl$_3$) δ 7.95 (d, J=13.5 Hz, 1H), 7.64 (d, J=8.8 Hz, 1H), 7.50-7.36 (m, 8H), 7.33 (s, 1H), 7.18 (d, J=7.0 Hz, 1H), 7.09-7.04 (m, 1H), 7.00 (d, J=2.6 Hz, 1H), 5.17 (s, 2H); $^{13}$C NMR (125 MHz, CDCl$_3$) δ 145.1, 141.1, 140.9, 137.4, 136.1, 134.7, 129.9, 129.6, 129.6, 129.5, 129.0, 128.8, 128.5, 128.4, 128.0, 127.6, 120.9, 116.9, 115.5, 109.9, 70.4; HRMS m/z: [M+Cl$^-$] for $C_{21}H_{16}Cl_2NO_3$, calcd, 400.0513. found, 400.0505.

(E)-5-(benzyloxy)-2-(2-nitrovinyl)-3'-(trifluoromethyl)-1,1'-biphenyl (7f)

$^1$H NMR (400 MHz, CDCl$_3$) δ 7.90 (d, J=13.5 Hz, 1H), 7.78-7.70 (m, 1H), 7.69-7.55 (m, 3H), 7.51-7.34 (m, 7H), 7.13-7.05 (dd, J=8.8, 2.6 Hz, 1H), 7.02 (d, J=2.6 Hz, 1H), 5.17 (s, 2H); $^{13}$C NMR (100 MHz, CDCl$_3$) δ 161.6, 155.7, 152.1, 145.1, 140.6, 140.0, 137.2, 136.4, 136.0, 133.2, 129.7, 129.3, 129.0, 128.6, 127.7, 121.0, 117.1, 115.8, 70.6; HRMS m/z: [M+H$^+$] for $C_{22}H_{17}F_3NO_3$, calcd, 400.1161. found, 400.1157.

(E)-5-(benzyloxy)-2-(2-nitrovinyl)-4'-(trifluoromethyl)-1,1'-biphenyl (7g)

Pushed through plug of SiO$_2$. TS1-189: $^1$H NMR (400 MHz, CDCl$_3$) δ 7.98-7.90 (m, 1H), 7.80 (d, J=8.0 Hz, 2H), 7.68 (d, J=8.8 Hz, 1H), 7.52-7.37 (m, 8H), 7.11 (d, J=8.8 Hz, 1H), 7.04 (s, 1H), 5.19 (s, 2H); $^{13}$C NMR (100 MHz, CDCl$_3$) δ 161.4, 147.8, 144.9, 144.3, 139.8, 138.6, 137.1, 136.4, 135.8, 133.5, 131.2, 129.5, 129.1, 128.8, 128.5, 127.6, 124.2, 120.8, 120.4, 117.0, 115.6, 70.4; HRMS m/z: [M+H$^+$] for $C_{22}H_{17}F_3NO_3$, calcd, 400.1155. found, 400.1151.

(E)-(5'-(benzyloxy)-2'-(2-nitrovinyl)-[1,1'-biphenyl]-2-yl)(methyl)sulfane (7h)

$^1$H NMR (400 MHz, CDCl$_3$) δ 7.71 (d, J=13.6 Hz, 1H), 7.62 (d, J=8.6 Hz, 1H), 7.45-7.31 (m, 7H), 7.31-7.29 (m, 1H), 7.25-7.19 (t, J=7.2 Hz, 1H), 7.13-6.99 (m, 2H), 6.95 (d, J=2.8 Hz, 1H), 5.09 (s, 2H), 2.35 (s, 3H); $^{13}$C NMR (100 MHz, CDCl$_3$) δ 161.5, 144.9, 138.0, 137.5, 137.2, 136.1, 135.7, 130.0, 129.4, 129.3, 128.8, 128.4, 127.7, 125.0, 124.9, 121.6, 117.0, 115.8, 70.3, 15.6; HRMS m/z: [M+H$^+$] for C$_{22}$H$_{19}$NO$_3$SK, calcd, 416.0718. found, 416.0756.

(E)-5-(benzyloxy)-2'-methoxy-2-(2-nitrovinyl)-1,1'-biphenyl (7i)

$^1$H NMR (500 MHz, CDCl$_3$) δ 7.86 (d, J=13.8 Hz, 1H), 7.65 (d, J=8.7 Hz, 1H), 7.57-7.34 (m, 7H), 7.24-7.17 (m, 1H), 7.16-6.99 (m, 4H), 5.15 (s, 2H), 3.74 (s, 3H); $^{13}$C NMR (125 MHz, CDCl$_3$) δ 161.6, 156.4, 143.7, 138.8, 136.3, 135.3, 131.4, 130.4, 128.9, 128.4, 127.7, 122.0, 121.1, 117.5, 115.1, 111.4, 70.4, 55.6; HRMS m/z: [M+H$^+$] for C$_{22}$H$_{19}$NO$_4$, calcd, 362.1387. found, 362.1389.

(E)-5-(benzyloxy)-3'-methoxy-2-(2-nitrovinyl)-1,1'-biphenyl (7j)

$^1$H NMR (500 MHz, CDCl$_3$) δ 8.04 (d, J=13.6 Hz, 1H), 7.62 (d, J=9.5 Hz, 1H), 7.46-7.37 (m, 6H), 7.07-7.02 (m, 3H), 7.02-6.97 (ddd, J=8.2, 2.6, 0.9 Hz, 1H), 6.88-6.84 (m, 1H), 6.84-6.80 (dd, J=2.6, 1.6 Hz, 1H), 5.15 (s, 2H), 3.85 (s, 3H); $^{13}$C NMR (125 MHz, CDCl$_3$) δ 161.5, 159.8, 146.8, 140.6, 138.2, 136.2, 135.9, 129.9, 129.5, 129.0, 128.6, 127.7, 122.3, 121.1, 116.8, 115.4, 115.4, 114.1, 70.5, 55.6; HRMS m/z: [M+Na$^+$] for C$_{22}$H$_{19}$NO$_4$Na, 384.1212. found, 384.1218.

(E)-5-(benzyloxy)-3'-methyl-2-(2-nitrovinyl)-1,1'-biphenyl (7k)

$^1$H NMR (500 MHz, CDCl$_3$) δ 8.01 (d, J=13.6 Hz, 1H), 7.62 (m, 1H), 7.48-7.39 (m, 7H), 7.39-7.33 (t, J=7.7 Hz, 1H), 7.14-7.07 (m, 2H), 7.05-6.99 (m, 2H), 5.15 (s, 2H), 2.43 (s, 3H); $^{13}$C NMR (125 MHz, CDCl$_3$) δ 138.4, 135.8, 130.4, 129.5, 129.3, 128.9, 128.7, 128.5, 127.8, 127.8, 126.9, 121.1, 116.8, 115.3, 77.5, 77.4, 77.2, 77.0, 70.5 21.7; HRMS m/z: [M+Na$^+$] for C$_{22}$H$_{19}$NO$_3$Nalcd, 368.1263. found, 368.1257.

(E)-4-(5'-(benzyloxy)-2'-(2-nitrovinyl)-[1,1'-biphenyl]-3-yl)methyl)morpholine (7l)

$^1$H NMR (400 MHz, CDCl$_3$) δ 7.98 (d, J=13.6 Hz, 1H), 7.63 (d, J=9.5 Hz, 1H), 7.48-7.33 (m, 8H), 7.33 (d, J=1.7 Hz, 1H), 7.23-7.20 (dd, J=6.7, 1.8 Hz, 1H), 7.08-6.99 (m, 2H), 5.15 (d, J=1.6 Hz, 2H), 3.79-3.67 (t, J=4.1 Hz, 4H), 3.56 (s, 2H), 2.55-2.40 (dd, J=5.7, 3.4 Hz, 4H); $^{13}$C NMR (100 MHz, CDCl$_3$) δ 161.5, 146.9, 139.2, 138.5, 138.1, 136.1, 135.8, 130.6, 129.5, 129.3, 128.9, 128.8, 128.5, 128.4, 127.7, 121.0, 116.9, 115.1, 70.4, 67.1, 63.3, 53.8; HRMS m/z: [M+H$^+$] for C$_{26}$H$_{27}$N$_2$O$_4$, calcd, 431.1971. found, 431.1974.

(E)-((5'-(benzyloxy)-2'-(2-nitrovinyl)-[1,1'-biphenyl]-4-yl)oxy)(tert-butyl)dimethylsilane (7m)

$^1$H NMR (400 MHz, CDCl$_3$) δ 8.03 (d, J=13.7 Hz, 1H), 7.61 (d, J=8.3 Hz, 1H), 7.49-7.33 (m, 6H), 7.17 (d, J=8.4 Hz, 2H), 7.02 (s, 2H), 6.95 (d, J=8.5 Hz, 2H), 5.15 (s, 2H), 1.04 (s, 9H), 0.30 (s, 6H); $^{13}$C NMR (100 MHz, CDCl$_3$) δ 161.5, 156.2, 146.8, 138.5, 136.2, 135.8, 132.2, 131.0, 129.6, 128.9, 128.5, 127.7, 121.0, 120.4, 116.8, 115.0, 70.4, 25.9, 18.4, −4.1; HRMS (FAB) m/z: [M+Na$^+$] for C$_{27}$HuNO$_4$SiNa, calcd, 484.1914. found, 484.1936.

(E)-5-(5-(benzyloxy)-2-(2-nitrovinyl)phenyl)benzo[d][1,3]dioxole (7n)

$^1$H NMR (400 MHz, CDCl$_3$) δ 8.03 (d, J=13.6 Hz, 1H), 7.59 (d, J=8.0 Hz, 1H), 7.50-7.33 (m, 6H), 7.05-6.98 (m, 2H), 6.92-6.85 (m, 1H), 6.79 (s, 1H), 6.71 (d, J=7.9 Hz, 1H), 6.03 (s, 2H), 5.17 (s, 2H); $^{13}$C NMR (100 MHz, CDCl$_3$) δ 161.4, 148.0, 147.9, 146.5, 138.1, 136.1, 135.7, 132.9, 129.5, 128.8, 128.4, 127.6, 123.6, 121.0, 116.7, 115.0, 109.9, 108.5, 101.5, 70.3; HRMS (FAB) m/z: [M+H$^+$] for C$_{22}$H$_{18}$NO$_5$, calcd, 376.1185. found, 376.1160.

(E)-3-(5-(benzyloxy)-2-(2-nitrovinyl)phenyl)pyridine (7o)

$^1$H NMR (400 MHz, CDCl$_3$) δ 8.70 (dd, J=4.8, 1.6 Hz, 1H), 8.59 (d, J=1.6 Hz, 1H), 7.89 (d, J=13.5 Hz, 1H), 7.68-7.60 (m, 2H), 7.47-7.32 (m, 8H), 7.12-7.06 (dd, J=8.7, 2.5 Hz, 1H), 7.00 (d, J=2.6 Hz, 1H), 5.15 (s, 2H); $^{13}$C NMR (100 MHz, CDCl$_3$) δ 161.5, 149.9, 149.6, 142.8, 136.9, 136.8, 136.3, 135.8, 134.8, 129.7, 128.8, 128.5, 127.6, 123.4, 121.1, 117.1, 115.8, 70.4; HRMS (FAB) m/z: [M+Na$^+$] for C$_{20}$H$_{17}$N$_2$O$_3$, 333.1239. found, 333.1234.

(E)-4-(5-(benzyloxy)-2-(2-nitrovinyl)phenyl)pyridine (7p)

$^1$H NMR (500 MHz, CDCl$_3$) δ 8.74 (dd, 2H, J=1.6, 4.4 Hz), 7.91 (d, 1H, J=13.6 Hz), 7.67 (d, 1H, J=8.8 Hz), 7.48 (d, 1H, J=13.4 Hz), 7.41 (m, 5H), 7.25 (dd, 2H, J=1.6, 4.4 Hz), 7.11 (dd, 1H, J=2.6, 8.7 Hz), 7.01 (d, 1H, J=2.5 Hz), 5.17 (s, 2H); $^{13}$C NMR (125 MHz, CDCl$_3$) δ 161.2, 150.2, 147.0, 143.7, 136.7, 136.6, 135.8, 128.9, 127.6, 124.5, 120.7, 116.8, 116.1, 70.6; ESI-HRMS m/z calculated for C$_{20}$H$_{17}$N$_2$O$_3$ [M+H]$^+$ 333.1239. found 333.1249.

Example 8

General Procedure for Preparation of 8a-p from 7a-p

N-(2-(5-(benzyloxy)-[1,1'-biphenyl]-2-yl)ethyl)acetamide (8a)

Nitrostyrene 7a (182 mg, 0.55 mmol) in THF (0.7 mL) was added dropwise to a solution of Lithiumaluminium hydride (42 mg, 1.12 mmol) in THF (2 mL) under organ atmosphere at RT. Upon completion (nearly immediately) the reaction was quenched by the addition of water (42 μL), 3M NaOH (42 μL), and water (84 μL). The resulted mixture was filtered through a plug of celite, washed with DCM, and dried over K$_2$CO$_3$. Upon filtration the mixture was concentrated to oil and used without further purification. Acetic anhydride (58 μL, 0.62 mmol) and triethylamine (93 μL, 0.67 mmol) were added to a solution of the crude amine in DCM (5.6 mL) under an organ atmosphere at RT. After 3 h the reaction was quenched with saturated aqueous ammonium chloride and extracted with DCM (3×10 mL); combined organic fractions were washed with saturated aqueous sodiumchloride, dried over Na$_2$SO$_4$, filtered and concentrated. The residue was purified by column chromatography (SiO$_2$; 3:1, Hex:EtOAc) to afford acetamide 8a (0.12 g, 0.35 mmol, 64%). $^1$H NMR (400 MHz, CDCl$_3$) δ 7.50-7.38 (m, 8H), 7.38-7.30 (m, 2H), 7.23 (d, J=8.4 Hz, 1H), 7.01-6.95 (dd, J=8.4, 2.7 Hz, 1H), 6.93 (d, J=2.7 Hz, 1H), 5.71 (br s, NH), 5.08 (s, 2H), 3.42-3.16 (q, J=7.0 Hz, 2H), 2.89-2.64 (t, J=7.2 Hz, 2H), 1.85 (s, 3H); $^{13}$C NMR (100 MHz, CDCl$_3$) δ 170.2, 157.2, 143.4, 141.4, 137.0, 130.8, 129.1, 128.7, 128.6, 128.4, 128.0, 127.6, 127.2, 116.6, 114.2, 70.1, 40.7, 31.9, 23.2; HRMS m/z: [M+K$^+$] for C$_{23}$H$_{23}$NO$_2$K calcd, 384.1361. found, 384.1359.

N-(2-(5-(benzyloxy)-3'-fluoro-[1,1'-biphenyl]-2-yl)ethyl)acetamide (8b)

$^1$H NMR (400 MHz, CDCl$_3$) δ 7.48-7.30 (m, 6H), 7.24-7.18 (d, J=8.4 Hz, 1H), 7.12-7.04 (m, 2H), 7.04-6.92 (ddd, J=18.6, 8.2, 2.5 Hz, 2H), 6.85 (d, J=2.7 Hz, 1H), 5.34 (br s, NH), 5.05 (s, 2H), 3.32-3.21 (q, J=6.4, 5.9 Hz, 2H), 2.79-2.68 (t, J=7.1 Hz, 2H), 1.86 (s, 3H); $^{13}$C NMR (100 MHz, CDCl$_3$) δ 170.3, 157.3, 143.7, 142.2, 136.9, 131.0, 130.1, 123.0, 128.8, 128.6, 128.2, 127.7, 125.0, 116.5, 116.4, 114.6, 114.4, 70.2, 40.8, 32.0, 23.3; HRMS m/z: [M+H$^+$] for C$_{23}$H$_{23}$FNO$_2$, calcd, 364.1713. found, 364.1705.

N-(2-(5-(benzyloxy)-4'-fluoro-[1,1'-biphenyl]-2-yl)ethyl)acetamide (8c)

$^1$H NMR (400 MHz, CDCl$_3$) δ 7.44-7.31 (m, 6H), 7.27-7.22 (dd, J=8.4, 5.5 Hz, 1H), 7.21-7.17 (d, J=8.4 Hz, 1H), 7.12-7.05 (m, 3H), 6.96-6.91 (dd, J=8.3, 3.0 Hz, 1H), 5.83 (br s, NH), 5.05 (s, 2H), 3.33-3.15 (q, J=6.7 Hz, 2H), 2.78-2.66 (t, J=7.2 Hz, 2H), 1.87 (s, 3H); $^{13}$C NMR (100 MHz, CDCl$_3$) δ 170.5, 157.3, 142.4, 137.0, 130.9, 130.8, 130.7, 128.7, 128.7, 128.2, 127.7, 116.8, 115.5, 115.3, 114.3, 70.2, 40.8, 32.0, 23.1; HRMS m/z: [M+Na$^+$] for C$_{23}$H$_{22}$FNO$_2$Na, calcd, 386.1527. found, 386.1529.

N-(2-(5-(benzyloxy)-2'-chloro-[1,1'-biphenyl]-2-yl)ethyl)acetamide (8d)

$^1$H NMR (500 MHz, CDCl$_3$) δ 7.52-7.45 (m, 1H), 7.45-7.40 (m, 2H), 7.40-7.35 (m, 3H), 7.35-7.29 (m, 3H), 7.25-7.21 (m, 1H), 7.05-6.95 (dd, J=8.5, 2.8 Hz, 1H), 6.82 (d, J=2.7 Hz, 1H), 5.93 (d, J=5.4 Hz, 1H), 5.05 (s, 2H), 3.36-3.19 (ddq, J=19.3, 13.0, 6.1 Hz, 2H), 2.67-2.49 (m, 2H), 1.93 (s, 3H); $^{13}$C NMR (125 MHz, CDCl$_3$) δ 175.7, 171.0, 157.1, 140.4, 139.8, 136.9, 133.1, 131.3, 130.4, 129.6, 129.0, 128.6, 128.0, 127.6, 126.8, 116.4, 114.9, 70.1, 40.3, 31.8, 22.9; HRMS m/z: [M+H$^+$] for C$_{23}$H$_{23}$ClNO$_2$, calcd, 380.1417. found, 380.1415.

N-(2-(5-(benzyloxy)-3'-chloro-[1,1'-biphenyl]-2-yl)ethyl)acetamide (8e)

$^1$H NMR (500 MHz, CDCl$_3$) δ 7.47-7.28 (m, 8H), 7.25-7.17 (m, 2H), 6.99-6.92 (dd, J=8.5, 2.7 Hz, 1H), 6.84 (d, J=2.8 Hz, 1H), 5.46 (br s, NH), 5.06 (s, 2H), 3.34-3.25 (m, 2H), 2.83-2.68 (t, J=7.3 Hz, 2H), 2.03 (s, 3H); $^{13}$C NMR (125 MHz, CDCl$_3$) δ 171.6, 157.5, 143.2, 142.1, 136.9, 134.3, 131.1, 129.9 129.3, 128.8, 128.3, 127.7, 127.6, 127.5, 116.7, 114.8, 70.3, 46.1, 41.3, 31.7, 22.5, 8.8; HRMS m/z: [M+H$^+$] for C$_{23}$H$_{23}$ClNO$_2$, calcd, 380.1412. found, 380.1414.

N-(2-(5-(benzyloxy)-3'-(trifluoromethyl)-[1,1'-biphenyl]-2-yl)ethyl)acetamide (8f)

$^1$H NMR (400 MHz, CDCl$_3$) δ 7.64 (d, J=7.7 Hz, 1H), 7.59-7.54 (m, 2H), 7.55-7.49 (t, J=7.3 Hz, 1H), 7.47-7.32 (m, 5H), 7.24 (d, J=8.5 Hz, 1H), 7.01-6.96 (dd, J=8.5, 2.7 Hz, 1H), 6.87 (d, J=2.7 Hz, 1H), 5.90 (br s, NH), 5.06 (s, 2H), 3.34-3.23 (q, J=6.9 Hz, 2H), 2.79-2.68 (t, J=7.3 Hz, 2H), 1.99 (s, 3H); $^{13}$C NMR (100 MHz, CDCl$_3$) δ 170.7, 157.4, 142.2, 141.9, 136.9, 132.6, 131.1, 129.0, 128.8, 128.5, 128.2, 127.7, 124.2, 116.7, 114.8, 70.3, 40.8 31.9, 23.0; HRMS m/z: [M+H$^+$] for C$_{24}$H$_{23}$F$_3$NO$_2$, calcd, 414.1676. found, 414.1681.

N-(2-(5-(benzyloxy)-4'-(trifluoromethyl)-[1,1'-biphenyl]-2-yl)ethyl)acetamide (8g)

$^1$H NMR (400 MHz, CDCl$_3$) δ 7.66 (d, J=8.1 Hz, 2H), 7.46-7.23 (m, 8H), 6.99-6.94 (dd, J=8.5, 2.7 Hz, 1H), 6.84 (d, J=2.7 Hz, 1H), 6.03 (t, J=5.5 Hz, 1H), 5.06 (s, 2H), 3.33-3.19 (dd, J=14.3, 6.4 Hz, 2H), 2.76-2.68 (dd, J=8.3, 6.6 Hz, 2H), 1.85 (s, 3H); $^{13}$C NMR (100 MHz, CDCl$_3$) δ 170.3, 157.1, 145.1, 141.8, 136.8, 130.9, 129.5, 129.1, 128.6, 128.6, 127.5, 125.6, 125.2, 125.2, 122.9, 116.4, 114.6, 70.1, 40.6, 31.9; HRMS m/z: [M+Na$^+$] for C$_{24}$H$_{22}$F$_3$NO$_2$Na, calcd, 436.1495. found, 436.1489.

N-(2-(5-(benzyloxy)-2'-(methylthio)-[1,1'-biphenyl]-2-yl)ethyl)acetamide (8h)

$^1$H NMR (400 MHz, CDCl$_3$) δ 7.48-7.30 (m, 7H), 7.28-7.18 (m, 2H), 7.14 (s, 1H), 7.03-6.98 (ddd, J=8.5, 2.8, 1.0 Hz, 1H), 6.87-6.83 (m, 1H), 5.63 (br s, NH), 5.05 (s, 2H), 3.43-3.16 (ddt, J=42.5, 13.3, 6.6 Hz, 2H), 2.66-2.52 (t, J=6.7 Hz, 2H), 2.39 (d, J=1.0 Hz, 3H), 1.84 (d, J=1.0 Hz, 3H); $^{13}$C NMR (100 MHz, CDCl$_3$) δ 170.3, 157.3, 141.1, 139.1, 137.6, 137.0, 130.6, 129.8, 129.4, 128.7, 128.4, 128.1, 127.7, 124.5, 124.0, 116.5, 115.2, 70.2, 40.1, 31.7, 23.3, 15.2; HRMS m/z: [M+Na$^+$] for C$_{24}$H$_{25}$NO$_2$SNa, calcd, 414.1504. found, 414.1509.

N-(2-(5-(benzyloxy)-2'-methoxy-[1,1'-biphenyl]-2-yl)ethyl)acetamide (8i)

$^1$H NMR (400 MHz, CDCl$_3$) δ 7.47-7.30 (m, 5H), 7.22 (d, J=8.5 Hz, 1H), 7.17-7.13 (dd, J=7.4, 1.9 Hz, 1H), 7.07-6.95 (m, 4H), 6.85 (d, J=2.7 Hz, 1H), 5.51 (br s, NH), 5.07 (s, 2H), 3.77 (s, 3H), 3.44-3.18 (m, 2H), 2.68-2.56 (td, J=6.8, 3.7 Hz, 2H), 1.86 (s, 3H); $^{13}$C NMR (125 MHz, CDCl$_3$) δ 170.0, 157.2, 156.4, 139.9, 137.1, 131.2, 130.1, 129.2, 128.7, 128.1, 127.8, 120.9, 116.8, 114.4, 111.2, 70.1, 55.8, 40.4, 31.9, 23.5; HRMS m/z: [M+H$^+$] for C$_{24}$H$_{26}$NO$_3$, calcd, 376.1913. found, 376.1902.

N-(2-(5-(benzyloxy)-3'-methoxy-[1,1'-biphenyl]-2-yl)ethyl)acetamide (8j)

$^1$H NMR (400 MHz, CDCl$_3$) δ 7.48-7.36 (m, 4H), 7.36-7.30 (m, 3H), 7.21 (d, J=8.4 Hz, 1H), 6.98-6.92 (m, 1H), 6.92-6.82 (m, 3H), 5.49 (br s, NH), 5.06 (s, 2H), 3.85 (s, 3H), 3.34-3.22 (q, J=6.6, 6.2 Hz, 2H), 2.85-2.68 (t, J=7.2 Hz, 2H), 1.85 (s, 3H); $^{13}$C NMR (100 MHz, CDCl$_3$) δ 170.1, 159.5, 157.2, 143.3, 142.9, 137.0, 130.8, 129.5, 128.7, 128.1, 128.1, 127.7, 121.6, 116.5, 114.9, 114.3, 112.7, 70.17, 55.4, 40.8, 32.0, 23.3; HRMS m/z: [M+H$^+$] for C$_{24}$H$_{25}$NO$_3$Na, calcd, 398.1732. found, 398.1725.

N-(2-(5-(benzyloxy)-3'-methyl-[1,1'-biphenyl]-2-yl)ethyl)acetamide (8k)

$^1$H NMR (400 MHz, CDCl$_3$) δ 7.45 (m, 3H), 7.40 (m, 3H), 7.37-7.30 (q, J=7.7, 7.1 Hz, 1H), 7.21 (d, J=1.4 Hz, 1H), 7.15-7.10 (m, 2H), 6.96 (d, J=8.1 Hz, 1H), 6.90 (s, 1H), 5.51 (br s, NH), 5.08 (s, 2H), 3.34-3.24 (q, J=6.5 Hz, 2H), 2.83-2.71 (t, J=7.0 Hz, 2H), 2.41 (s, 3H), 1.84 (s, 3H); $^{13}$C NMR (100 MHz, CDCl$_3$) δ 170.0, 157.2, 143.5, 141.4, 138.0, 137.0, 130.7, 129.9, 128.7, 128.7, 128.3, 128.1, 128.0, 127.6, 126.2, 116.5, 114.2, 70.1, 40.8, 31.9, 23.3, 21.6; ESI-HRMS m/z calculated for $C_{24}H_{25}NO_2Na$ [M+Na]$^+$382.1777. found 382.1770.

N-(2-(5-(benzyloxy)-3'-(morpholinomethyl)-[1,1'-biphenyl]-2-yl)ethyl)acetamide (8l)

$^1$H NMR (400 MHz, CDCl$_3$) δ 7.47-7.30 (m, 7H), 7.28 (s, 1H), 7.24-7.18 (m, 2H), 6.98-6.93 (dd, J=8.4, 2.8 Hz, 1H), 6.89 (d, J=2.7 Hz, 1H), 5.40 (s, 1H), 5.05 (s, 2H), 3.75-3.69 (t, J=4.7 Hz, 4H), 3.55 (s, 2H), 3.36-3.22 (q, J=6.9 Hz, 2H), 2.80-2.68 (t, J=7.1 Hz, 2H), 2.47 (m, 4H), 1.85 (s, 3H); $^{13}$C NMR (100 MHz, CDCl$_3$) δ 170.0, 157.3, 143.4, 141.5, 138.0, 137.1, 130.9, 123.0, 128.7, 128.7, 128.4, 128.2, 128.2, 128.0, 127.7, 116.8, 114.1, 70.2, 67.1, 63.5, 53.8, 40.6, 32.1, 23.4; HRMS m/z: [M+H]$^+$ for $C_{28}H_{33}N_2O_3$, calcd, 445.2491. found, 445.2494.

N-(2-(5-(benzyloxy)-4'-((tert-butyldimethylsilyl)oxy)-[1,1'-biphenyl]-2-yl)ethyl)acetamide (8m)

$^1$H NMR (500 MHz, CDCl$_3$) δ 7.44 (d, J=7.5 Hz, 3H), 7.42-7.36 (dt, J=10.5, 5.7 Hz, 3H), 7.36-7.31 (m, 1H), 7.21-7.14 (m, 3H), 6.94-6.86 (m, 2H), 5.08 (s, 2H), 3.34-3.23 (q, J=6.7 Hz, 2H), 2.75 (t, J=7.1 Hz, 2H), 1.74 (s, 3H), 1.97 (s, 9H), 0.25 (s, 6H); $^{13}$C NMR (125 MHz, CDCl$_3$) δ 169.9, 157.3, 155.0, 143.3, 137.2, 134.5, 130.8, 130.2, 128.7, 128.1, 127.7, 120.0, 116.8, 114.0, 70.2, 53.6, 40.7, 32.1, 25.8, 23.4, 18.4, —4.2; HRMS (FAB) m/z: [M+Na]$^+$ for $C_{29}H_{37}NO_3SiNa$, calcd, 498.2440. found, 498.2447.

N-(2-(benzo[d][1,3]dioxol-5-yl)-4-(benzyloxy)phenethyl)acetamide (8n)

$^1$H NMR (400 MHz, CDCl$_3$) δ 7.49-7.36 (m, 5H), 7.34 (d, J=4.4 Hz, 1H), 7.20 (d, J=8.3 Hz, 1H), 6.96-6.89 (dd, J=8.4, 2.8 Hz, 1H), 6.90-6.84 (m, 2H), 6.81-6.73 (m, 1H), 6.00 (s, 2H), 5.69-5.60 (t, J=5.8 Hz, 1H), 5.06 (s, 2H), 3.42-3.16 (m, 2H), 2.93-2.68 (t, J=7.3 Hz, 2H), 1.87 (s, 3H); $^{13}$C NMR (100 MHz, CDCl$_3$) δ 170.4, 157.2, 147.5, 146.8, 143.0, 137.0, 135.2, 130.8, 129.3, 128.8, 128.1, 127.6, 123.2, 122.4, 116.7, 114.1, 109.7, 108.3, 101.2, 70.1, 40.7, 31.9, 23.2; HRMS (FAB) m/z: [M+Na]$^+$ for $C_{24}H_{23}NO_4Na$, 412.1519. found, 412.1524.

N-(4-(benzyloxy)-2-(pyridin-3-yl)phenethyl)acetamide (8o)

$^1$H NMR (400 MHz, CDCl$_3$) δ 8.69-8.52 (dd, J=18.2, 4.0 Hz, 2H), 7.71-7.63 (dt, J=7.8, 2.0 Hz, 1H), 7.49-7.31 (m, 7H), 7.06-6.97 (dd, J=8.5, 2.8 Hz, 1H), 6.84 (d, J=2.8 Hz, 1H), 5.06 (s, 2H), 3.36-3.20 (q, J=6.5 Hz, 2H), 2.78-2.67 (dd, J=8.1, 6.6 Hz, 2H), 1.90 (s, 3H); $^{13}$C NMR (125 MHz, CDCl$_3$) δ 170.1, 157.5, 149.6, 148.5, 139.5, 136.9, 131.2, 129.0, 128.8, 128.3, 127.7, 123.5, 116.9, 115.0, 70.3, 40.7, 32.2, 23.5; HRMS (FAB) m/z: [M+H]$^+$ for $C_{22}H_{23}N_2O_2$, calcd, 347.1759. found, 347.1754.

N-(4-(benzyloxy)-2-(pyridin-4-yl)phenethyl)acetamide (8p)

$^1$H NMR (400 MHz, CDCl$_3$) δ 8.66 (d, J=5.1 Hz, 2H), 7.46-7.39 (m, 5H), 7.36 (s, 1H), 7.30 (s, 2H), 7.06-7.01 (m, 1H), 6.84 (d, J=2.7 Hz, 1H), 5.94 (d, J=4.8 Hz, 1H), 5.09 (s, 2H), 3.35-3.23 (dd, J=14.5, 6.4 Hz, 2H), 2.74 (t, J=7.5 Hz, 2H), 1.90 (s, 3H); $^{13}$C NMR (100 MHz, CDCl$_3$) δ 171.4, 158.1, 156.3, 137.2, 132.3, 132.2, 130.8, 128.7, 128.5, 129.7, 127.5, 117.9, 106.2, 103.0, 69.9, 41.1, 29.7, 29.6, 23.1; HRMS (FAB) m/z: [M+Na]$^+$ for $C_{22}H_{22}N_2O_2Na$, calcd, 369.1579. found, 369.1573.

Example 9

General Hydrogenolysis Procedure for Compounds 8a-p

N-(2-(5-hydroxy-[1,1'-biphenyl]-2-yl)ethyl)acetamide (9a)

Palladium on carbon (10%, 5 mg) was added to 8a (120 mg, 0.35 mmol) in degassed MeOH (3.5 mL) and the solution was placed under an atmosphere of H$_2$. After 12 h, the solution was diluted with DCM and filtered through Celite. The eluent was concentrated to afford a yellow solid, which was purified by column chromatography (SiO$_2$, 100:5, DCM:MeOH) to afford phenol 9a (64 mg, 0.25 mmol, 79%) as a pale yellow amorphous solid. $^1$H NMR (400 MHz, CDCl$_3$) δ 7.25-7.14 (m, 5H), 7.11-7.05 (m, 1H), 6.90 (d, J=8.3 Hz, 1H), 6.64 (d, J=8.3 Hz, 1H), 6.59 (d, J=2.5 Hz, 1H), 5.61 (t, J=5.5 Hz, 1H), 3.12-3.02 (m, 2H), 2.55 (t, J=7.1 Hz, 2H), 1.66 (s, 3H); $^{13}$C NMR (100 MHz, CDCl$_3$) δ 171.2, 155.2, 143.4, 141.6, 130.8, 129.1, 128.4, 127.2, 127.2, 117.4, 115.0, 41.1, 31.8, 23.2; HRMS m/z: [M+Na]$^+$ for $C_{16}H_{17}NO_2Na$, calcd, 278.1151. found, 278.1155.

N-(2-(3'-fluoro-5-hydroxy-[1,1'-biphenyl]-2-yl)ethyl)acetamide (9b)

$^1$H NMR (500 MHz, MeOD) δ 7.88 (s, 1H), 7.39 (d, J=7.5 Hz, 1H), 7.16-6.99 (m, 4H), 6.77 (d, J=8.1 Hz, 1H), 6.62 (d, J=2.6 Hz, 1H), 3.15 (t, J=6.6 Hz, 2H), 2.66 (t, J=7.4 Hz, 2H), 1.80 (s, 3H); $^{13}$C NMR (125 MHz, MeOD) δ 173.1, 164.8, 162.9, 156.7, 145.5, 143.3, 132.0, 131.0, 128.3, 126.1, 117.6, 115.9, 114.7, 41.8, 32.8, 22.5; HRMS m/z: [M+Na]$^+$ for $C_{16}H_{16}FNO_2Na$, calcd, 296.1063. found, 296.1059.

N-(2-(4'-fluoro-5-hydroxy-[1,1'-biphenyl]-2-yl)ethyl)acetamide (9c)

$^1$H NMR (400 MHz, MeOD) δ 7.26-7.20 (m, 2H), 7.11-7.03 (m, 3H), 6.71 (dd, J=8.3, 2.5 Hz, 1H), 6.56 (d, J=2.5 Hz, 1H), 3.07 (t, J=7.6 Hz, 2H), 2.60 (t, J=7.6 Hz, 2H), 1.78 (s, 3H); $^{13}$C NMR (100 MHz, MeOD) δ 173.0, 156.7, 143.5, 139.2, 131.9, 131.9, 131.8, 128.5, 117.8, 116.0, 115.8, 115.7, 41.8, 32.9, 22.5; HRMS m/z: [M+Na]$^+$ for $C_{16}H_{16}FNO_2Na$, calcd, 296.1063. found, 296.1065.

N-(2-(2'-chloro-5-hydroxy-[1,1'-biphenyl]-2-yl)ethyl)acetamide (9d)

$^1$H NMR (400 MHz, CDCl$_3$) δ 8.37 (br s, OH), 7.45-7.39 (m, 1H), 7.32-7.24 (m, 2H), 7.21-7.15 (m, 1H), 7.09 (d, J=8.3 Hz, 1H), 6.85 (dd, J=8.3, 2.5 Hz, 1H), 6.68 (d, J=2.6 Hz, 1H), 5.62 (s, 1H), 3.40-3.14 (m, 2H), 2.63-2.44 (dd, J=7.1, 5.1 Hz, 2H), 1.86 (s, 3H); $^{13}$C NMR (125 MHz, CDCl$_3$) δ 171.1, 155.1, 140.5, 140.0, 133.2, 131.4, 130.5, 129.7, 129.0, 127.7, 126.9, 117.3, 115.7, 40.5, 31.8, 23.3; HRMS m/z: [M+H]$^+$ for $C_{16}H_{17}ClNO_2$, 290.0948. found, 290.0941.

N-(2-(3'-chloro-5-hydroxy-[1,1'-biphenyl]-2-yl)ethyl)acetamide (9e)

$^1$H NMR (500 MHz, CDCl$_3$) δ 7.40-7.09 (m, 5H), 6.83-6.76 (dq, J=8.1, 4.9, 3.8 Hz, 1H), 6.76-6.67 (dd, J=18.3, 2.7

Hz, 1H), 3.34-3.23 (p, J=6.6 Hz, 2H), 2.77-2.64 (dt, J=14.3, 7.2 Hz, 2H), 1.76 (s, 3H); $^{13}$C NMR (125 MHz, CDCl$_3$) δ 170.8, 154.9, 143.6, 141.6, 131.0, 130.9, 129.7, 129.2, 128.5, 127.5, 117.4, 115.5, 115.0, 41.0, 32.0, 23.4; HRMS m/z: [M+Na$^+$] for C$_{16}$H$_{16}$ClNO$_2$Na, calcd, 312.0762. found, 312.0788.

N-(2-(5-hydroxy-3'-(trifluoromethyl)-[1,1'-biphenyl]-2-yl)ethyl)acetamide (9f)

$^1$H NMR (400 MHz, CDCl$_3$) δ 7.64-7.39 (m, 4H), 7.07 (s, 1H), 6.82 (s, 1H), 6.73 (s, 1H), 6.00 (s, 1H), 3.34-3.18 (q, J=6.8 Hz, 2H), 2.66 (t, J=7.0 Hz, 2H), 1.87 (s, 3H); $^{13}$C NMR (100 MHz, CDCl$_3$) δ 171.3, 155.4, 142.4, 141.8, 132.6, 131.0, 130.8, 128.9, 126.9, 125.8, 125.8, 124.0, 117.3, 115.6, 60.7, 41.0, 21.2; HRMS m/z: [M+Na$^+$] for C$_{17}$H$_{16}$F$_3$NO$_2$Na, calcd, 346.1031. found, 346.1040.

N-(2-(5-hydroxy-4'-(trifluoromethyl)-[1,1'-biphenyl]-2-yl)ethyl)acetamide (9g)

$^1$H NMR (400 MHz, CDCl$_3$) δ 7.54 (d, 2H, J=8.0 Hz), 7.31 (d, 2H, J=8.0 Hz), 7.03 (d, 1H, J=8.3 Hz), 6.72 (dd, 1H, J=2.5, 8.3 Hz), 6.59 (d, 1H, J=2.5 Hz), 4.09 (br s, 2H), 3.10 (t, J=7.5 Hz, 2H), 2.56 (t, 2H, J=7.5 Hz), 1.76 (s, 3H); $^{13}$C NMR (100 MHz, CDCl$_3$) δ 170.5, 155.1, 146.3, 141.7, 130.8, 129.5, 127.1, 125.1 (q, J=4.2 Hz), 116.9, 116.5, 115.3, 45.6, 40.6, 23.0; HRMS m/z: [M+H$^+$] for C$_{17}$H$_{16}$F$_3$NO$_2$Na, calcd, 346.1031. found, 346.1025.

N-(2-(5-hydroxy-2'-(methylthio)-[1,1'-biphenyl]-2-yl)ethyl)acetamide (9h)

$^1$H NMR (500 MHz, CDCl$_3$) δ 7.40-7.34 (m, 1H), 7.25-7.14 (m, 3H), 7.12-7.07 (m, 1H), 6.86-6.82 (dd, J=8.4, 2.7 Hz, 1H), 6.68 (d, J=2.7 Hz, 1H), 5.51 (br s, NH), 3.42-3.16 (m, 2H), 2.55 (t, J=6.8 Hz, 2H), 2.37 (s, 3H), 1.85 (s, 3H); $^{13}$C NMR (125 MHz, CDCl$_3$) δ 170.5, 154.5, 141.2, 139.1, 137.6, 130.7, 123.0, 128.8, 128.5, 124.6, 124.0, 117.3, 115.6, 40.2, 31.6, 23.4, 15.2; HRMS m/z: [M+Na$^+$] for C$_{17}$H$_{19}$NO$_2$SNa, calcd, 324.1034. found, 324.1035.

N-(2-(5-hydroxy-2'-methoxy-[1,1'-biphenyl]-2-yl)ethyl)acetamide (9i)

$^1$H NMR (400 MHz, CDCl$_3$) δ 7.52 (br s, OH), 7.41-7.31 (m, 1H), 7.14-7.07 (dd, J=8.4, 6.4 Hz, 1H), 7.05-6.94 (m, 3H), 6.83-6.76 (dd, J=8.3, 2.7 Hz, 1H), 6.70 (d, J=2.7 Hz, 1H), 5.55 (s, 1H), 3.76 (s, 3H), 3.41-3.17 (ddt, J=34.4, 13.1, 6.5 Hz, 2H), 2.57 (t, J=6.9 Hz, 2H), 1.85 (s, 3H); $^{13}$C NMR (125 MHz, CDCl$_3$) δ 171.0, 156.4, 155.1, 139.9, 131.3, 130.5, 130.1, 129.1, 128.5, 121.0, 117.7, 115.2, 111.4, 55.9, 40.7, 31.7, 23.3; HRMS m/z: [M+Na$^+$] for C$_{17}$H$_{19}$NO$_3$Na, calcd, 308.1263. found, 308.1264.

N-(2-(5-hydroxy-3'-methoxy-[1,1'-biphenyl]-2-yl)ethyl)acetamide (9j)

$^1$H NMR (400 MHz, CDCl$_3$) δ 7.83 (br s, OH), 7.30-7.24 (m, 1H), 7.06 (d, J=8.2 Hz, 1H), 6.90-6.70 (m, 5H), 5.59 (t, J=5.7 Hz, 1H), 3.79 (s, 3H), 3.33-3.19 (q, J=6.9 Hz, 2H), 2.69 (t, J=7.1 Hz, 2H), 1.85 (s, 3H); $^{13}$C NMR (100 MHz, CDCl$_3$) δ 171.1, 159.4, 155.1, 143.3, 143.0, 130.9, 129.5, 127.3, 121.7, 117.2, 115.1, 115.0, 112.6, 55.4, 41.1, 31.8, 23.3; HRMS m/z: [M+H$^+$] for C$_{17}$H$_{20}$NO$_3$, calcd, 286.1443. found, 286.1436.

N-(2-(5-hydroxy-3'-methyl-[1,1'-biphenyl]-2-yl)ethyl)acetamide (9k)

$^1$H NMR (400 MHz, CDCl$_3$) δ 7.50 (br s, OH), 7.30-7.24 (m, 1H), 7.15 (d, J=7.6 Hz, 1H), 7.09-7.03 (m, 3H), 6.80 (d, J=7.6 Hz, 1H), 6.73 (s, 1H), 5.53 (br s, NH), 3.31-3.21 (q, J=6.7 Hz, 2H), 2.71 (t, J=7.0 Hz, 2H), 2.37 (s, 3H), 1.85 (s, 3H); $^{13}$C NMR (1001 MHz, CDCl$_3$) δ 170.9, 155.0, 143.6, 141.6, 138.1, 130.8, 1230.0, 128.3, 128.0, 127.4, 126.3, 117.4, 114.9, 41.1, 31.8, 23.3, 21.7; HRMS m/z: [M+Na$^+$] for C$_{17}$H$_{19}$NO$_2$Na, calcd, 292.1308. found, 292.1314.

N-(2-(5-hydroxy-3'-(morpholinomethyl)-[1,1'-biphenyl]-2-yl)ethyl)acetamide (9l)

$^1$H NMR (500 MHz, CDCl$_3$) δ 7.36-7.23 (m, 4H), 7.16 (d, J=7.2 Hz, 1H), 7.07 (d, J=8.2 Hz, 1H), 6.74-6.69 (dd, J=8.2, 2.7 Hz, 1H), 6.62 (d, J=2.6 Hz, 1H), 5.50 (br s, NH), 3.74 (m, 4H), 3.53 (s, 3H), 3.29-3.20 (q, J=6.7 Hz, 2H), 2.69 (t, J=7.0 Hz, 2H), 2.49 (t, J=4.8 Hz, 4H), 1.87 (s, 3H); $^{13}$C NMR (125 MHz, CDCl$_3$) δ 170.5, 155.0, 143.4, 141.7, 130.9, 130.2, 128.4, 128.2, 117.5, 115.0, 66.9, 63.4, 53.8, 40.8, 32.0, 23.4; HRMS m/z: [M+H$^+$] for C$_{11}$H$_{27}$N$_2$O$_3$, calcd, 355.2022. found, 355.2024.

N-(2-(4'-((tert-butyldimethylsilyl)oxy)-5-hydroxy-[1,1'-biphenyl]-2-yl)ethyl)acetamide (9m)

$^1$H NMR (500 MHz, CDCl$_3$) δ 7.16-7.10 (d, J=6.7 Hz, 2H), 7.10-7.06 (d, J=8.2 Hz, 1H), 7.00 (br s, OH), 6.91-6.84 (d, J=8.4 Hz, 2H), 6.79-6.72 (m, 2H), 5.38 (s, 1H), 3.34-3.21 (q, J=6.6 Hz, 2H), 2.78-2.64 (t, J=6.9 Hz, 2H), 1.93-1.81 (s, 3H), 1.00 (s, 9H), 0.24 (s, 6H); $^{13}$C NMR (125 MHz, CDCl$_3$) δ 170.7, 155.0, 154.9, 143.3, 134.6, 130.9, 130.3, 127.8, 120.0, 117.5, 114.7, 41.0, 32.0, 26.0, 23.4, 18.4, −4.1; HRMS (FAB) m/z: [M+Na$^+$] for C$_{22}$H$_{31}$NO$_3$SiNa, calcd, 408.1965. found, 408.1960.

N-(2-(benzo[d][1,3]dioxol-5-yl)-4-hydroxyphenethyl)acetamide (9n)

$^1$H NMR (500 MHz, CDCl$_3$) δ 8.00 (br s, OH), 7.08-6.98 (d, J=8.3 Hz, 1H), 6.81-6.73 (m, 2H), 6.73-6.68 (m, 2H), 6.68-6.64 (dd, J=7.9, 1.7 Hz, 1H), 5.97-5.92 (s, 2H), 5.70-5.63 (t, J=5.7 Hz, 1H), 3.29-3.21 (td, J=7.1, 5.6 Hz, 2H), 2.75-2.63 (t, J=7.2 Hz, 2H), 1.89-1.81 (s, 3H); $^{13}$C NMR (125 MHz, CDCl$_3$) δ 171.1, 155.1, 147.5, 146.8, 143.0, 135.4, 130.8, 127.4, 122.4, 117.5, 114.9, 109.8, 108.3, 101.2, 41.1, 31.9, 23.3; HRMS (FAB) m/z: [M+Na$^+$] for C$_{17}$H$_{17}$NO$_4$Na, calcd, 322.1050. found, 322.1022.

N-(4-hydroxy-2-(pyridin-3-yl)phenethyl)acetamide (9o)

$^1$H NMR (400 MHz, CDCl$_3$) δ 8.54 (s, 2H), 7.72 (d, J=7.9 Hz, 1H), 7.42-7.34 (dd, J=8.0, 4.8 Hz, 1H), 7.14 (d, J=8.4 Hz, 1H), 6.90-6.84 (dd, J=8.3, 2.7 Hz, 1H), 6.73 (d, J=2.7 Hz, 1H), 5.82 (t, J=5.9 Hz, 2H), 3.33-3.19 (q, J=6.8 Hz, 2H), 2.69 (t, J=7.2 Hz, 2H), 1.85 (s, 3H); $^{13}$C NMR (100 MHz, CDCl$_3$) δ 170.7, 156.1, 149.1, 147.7, 138.8, 138.0, 131.4, 127.3, 123.7, 117.5, 116.4, 100.2, 40.9, 32.0, 23.4; HRMS (FAB) m/z: [M+H$^+$] for C$_{15}$H$_{17}$N$_2$O$_2$, calcd, 257.1290. found, 257.1297.

N-(4-hydroxy-2-(pyridin-4-yl)phenethyl)acetamide (9p)

$^1$H NMR (400 MHz, CDCl$_3$) δ 8.69-8.60 (m, 2H), 7.25 (d, J=1.5 Hz, 2H), 7.17 (d, J=8.4 Hz, 1H), 6.90-6.83 (dd, J=8.4, 2.7 Hz, 1H), 6.70 (d, J=2.7 Hz, 1H), 6.02 (br s, OH), 5.47 (s, 1H), 3.33-3.24 (q, J=7.0 Hz, 2H), 2.71 (t, J=7.4 Hz, 2H), 1.90 (s, 3H); $^{13}$C NMR (125 MHz, CDCl$_3$) δ 173.0, 157.1, 152.8, 149.7, 149.6, 141.3, 132.4, 128.0, 126.2, 117.2, 117.1, 116.9, 41.8, 32.8, 22.5; HRMS (FAB) m/z: [M+Na$^+$] for C$_{15}$H$_{16}$N$_2$O$_2$Na, calcd, 279.1104. found, 279.1109.

Example 10

General Procedure for Activated Noviose Carbamate Coupling and Followed by Methanolysis of Compounds 9a-p Borontrifluoride etherate (6.2 μL, 0.05 mmol) was added to 9a-p (0.25 mmol) and activated noviose (0.2 mmol) in 2.5 mL anhydrous DCM. After stirring at RT for 2 h, triethylamine (150 μL) was added and the solvent was concentrated. The residue was partially purified via column chromatography (SiO$_2$, 100:8 DCM:acetone) to give noviose coupled product as a colorless foam, which was used directly for next step. Triethylamine (0.22 mL, 10%) was added to the cyclic carbonate (100 mg, 0.22 mmol) in MeOH (2.2 mL). After 12 h, the solvent was concentrated and the residue was purified via column chromatography (SiO$_2$, 10:1, DCM:Acetone) to afford inseparable diastereomers 11a-p (see following experimental section for diastereoselectivities) as a colorless amorphous solids.

N-(2-(5-(((3R,4S,5R)-3,4-dihydroxy-5-methoxy-6,6-dimethyltetrahydro-2H-pyran-2-yl)oxy)-[1,1'-biphenyl]-2-yl)ethyl)acetamide (11a)

Colorless amorphous solid (63% yield over 2 steps); $^1$H NMR (500 MHz, CDCl$_3$) δ 7.41-7.28 (m, 3H), 7.28-7.18 (dt, J=5.9, 3.2 Hz, 2H), 7.13 (m, 1H), 6.97 (m, 1H), 6.92-6.78 (dd, J=7.6, 2.7 Hz, 1H), 5.55-5.47 (dd, J=7.7, 2.7 Hz, 1H), 5.39 (m, 1H), 4.14 (m, 2H), 3.58-3.46 (m, 3H), 3.34-3.15 (m, 4H), 3.03 (d, J=5.5 Hz, 1H), 2.77-2.65 (m, 2H), 1.84-1.76 (m, 3H), 1.31 (d, J=4.9 Hz, 3H), 1.21-1.10 (m, 3H); $^{13}$C NMR (125 MHz, CDCl$_3$) δ 170.3, 155.4, 143.5, 141.4, 130.8, 129.5, 129.2, 128.5, 127.4, 118.2, 115.2, 98.1, 84.5, 78.4, 71.5, 68.8, 62.0, 40.8, 32.1, 29.2, 23.4, 23.1; HRMS m/z: [M+H$^+$] for C$_{24}$H$_{32}$NO$_6$, calcd, 430.2224. found, 430.2227.

N-(2-(5-(((3R,4S,5R)-3,4-dihydroxy-5-methoxy-6,6-dimethyltetrahydro-2H-pyran-2-yl)oxy)-3'-fluoro-[1,1'-biphenyl]-2-yl)ethyl)acetamide (11b)

Colorless amorphous solid (51% yield over 2 steps); $^1$H NMR (500 MHz, CDCl$_3$) δ 7.39 (dd, 1H, J=7.9, 13.9 Hz), 7.22 (d, 1H, J=8.5 Hz), 7.07 (dd, 2H, J=7.5, 10.5 Hz), 7.02 (dd, 1H, J=2.8, 8.4 Hz), 6.99 (m, 1H), 6.91 (d, 1H, J=2.7 Hz), 5.34 (d, 1H, J=1.3 Hz), 5.28 (s, 1H), 4.20 (d, 1H, J=2.2 Hz), 3.80 (m, 1H), 3.63 (s, 3H), 3.30 (d, 1H), 3.28 (m, 2H), 2.75 (t, 2H, J=7.2 Hz), 2.63 (m, 2H, J=15.9 Hz), 1.87 (s, 3H), 1.41 (s, 3H), 1.28 (s, 3H); $^{13}$C NMR (125 MHz, CDCl$_3$) δ 169.9, 163.5-161.6 (d, J=251 Hz) 155.0, 143.2 (d, J=7.8 Hz), 142.1 (d, J=1.8 Hz), 130.9, 130.1, 130.0 (d, J=8.8 Hz), 124.8 (d, J=2.8 Hz), 118.0, 116.0 (d, J=8.8 Hz), 115.4, 114.3 (d, J=21.6 Hz), 93.8, 84.2, 76.0, 71.3, 71.1, 62.0, 40.4, 32.0, 28.6, 23.3, 18.5; HRMS m/z: [M+H$^+$] for C$_{24}$H$_{31}$FNO$_6$, calcd, 448.2180. found, 448.2174. This material was determined to be 95.6% pure (retention time=6.401) by HPLC (Phenomenex Luna C-18, 5 10×250 mm column eluting with 30% CH$_3$CN, 70% H$_2$O, flow rate 5.0 mL/min).

N-(2-(5-(((3R,4S,5R)-3,4-dihydroxy-5-methoxy-6,6-dimethyltetrahydro-2H-pyran-2-yl)oxy)-4'-fluoro-[1,1'-biphenyl]-2-yl)ethyl)acetamide (11c)

Colorless amorphous solid (57% yield over 2 steps); $^1$H NMR (500 MHz, CDCl$_3$) δ 7.25 (dd, 2H, J=5.4, 8.6 Hz), 7.18 (d, 1H, J=8.5 Hz), 7.10 (t, 2H, J=8.7 Hz), 7.01 (dd, 1H, J=2.7, 8.5 Hz), 6.87 (d, 1H, J=2.7 Hz), 5.54 (d, 1H, J=2.2 Hz), 5.37 (t, 1H, J=5.2 Hz), 4.20 (dd, 1H, J=3.3, 9.1 Hz), 4.15 (m, 1H), 3.59 (s, 3H), 3.33 (d, 1H, J=9.1 Hz), 3.26 (q, 2H, J=6.9 Hz), 2.97 (s, 1H), 2.81 (s, 1H), 2.72 (t, 2H, J=7.3), 1.87 (s, 3H), 1.36 (s, 3H), 1.22 (s, 3H); $^{13}$C NMR (125 MHz, CDCl$_3$) δ 170.2, 163.2-161.3 (d, J=250 Hz), 155.3, 142.3, 137.2 (d, J=3.2 Hz), 130.8, 130.8, 130.7, 129.5, 118.1, 115.4, 115.3, 115.3, 97.9, 84.4, 78.3, 71.4, 68.7, 62.0, 40.6, 32.1, 29.1, 23.4, 23.1; HRMS m/z: [M+Na$^+$] for C$_{24}$H$_{30}$FNO$_6$, calcd, 470.1955. found, 470.1958.

N-(2-(2'-chloro-5-(((3R,4S,5R)-3,4-dihydroxy-5-methoxy-6,6-dimethyltetrahydro-2H-pyran-2-yl)oxy)-[1,1'-biphenyl]-2-yl)ethyl)acetamide (11d)

Colorless amorphous solid (62% yield over 2 steps); $^1$H NMR (500 MHz, CDCl$_3$) δ 7.46 (m, 1H), 7.31 (m, 2H), 7.21 (m, 2H), 7.03 (m, 1H), 6.86 (dd, 1H, J=2.7, 13.2 Hz), 5.55 (m, 1H), 5.42 (s, 1H), 4.20 (dt, 1H, J=3.0, 9.1 Hz), 4.14 (m, 1H), 3.59 (s, 3H), 3.33 (dd, 1H, J=2.5, 9.1 Hz), 3.26 (ddt, 2H, J=4.8, 6.8, 9.3 Hz), 3.11 (s, 1H), 2.93 (s, 1H), 2.58 (tq, 2H, J=7.1, 14.2 Hz), 1.86 (s, 3H), 1.35 (d, 3H, J=2.4 Hz), 1.20 (t, 3H, J=5.8 Hz); $^{13}$C NMR (125 MHz, CDCl$_3$) δ 170.2, 155.2, 140.6, 140.5, 139.8, 133.4, 131.4, 130.5, 129.8, 126.9, 118.1, 117.9, 116.05, 97.9, 84.5, 78.4, 71.5, 71.4, 68.7, 62.1, 62.0, 40.2, 40.2, 32.1, 32.1, 29.3, 29.2, 23.5, 23.1, 23.0; HRMS m/z: [M+Na$^+$] for C$_{24}$H$_{30}$ClNO$_6$Na, 486.1659. found, 486.1652.

N-(2-(3'-chloro-5-(((3R,4S,5R)-3,4-dihydroxy-5-methoxy-6,6-dimethyltetrahydro-2H-pyran-2-yl)oxy)-[1,1'-biphenyl]-2-yl)ethyl)acetamide (11e)

Colorless amorphous solid (55% yield over 2 steps); $^1$H NMR (500 MHz, CDCl$_3$) δ 7.35 (m, 2H), 7.28 (m, 1H), 7.18 (m, 2H), 7.03 (dd, 1H, J=2.7, 8.5 Hz), 6.87 (d, 1H, J=2.7 Hz), 5.55 (t, 1H, J=2.5 Hz), 5.34 (m, 1H), 4.21 (dd, 1H, J=3.1, 9.1 Hz), 4.16 (m, 1H), 3.60 (s, 3H), 3.34 (dd, 1H, J=1.9, 9.1 Hz), 3.28 (m, 2H), 2.75 (dt, 4H, J=7.3, 14.5 Hz), 1.88 (s, 3H), 1.37 (s, 3H), 1.22 (s, 3H); $^{13}$C NMR (125 MHz, CDCl$_3$) δ 170.1, 155.4, 143.5, 142.0, 134.3, 131.0, 130.9, 129.8, 129.4, 128.5, 127.6, 127.4, 118.2, 115.7, 97.9, 84.6, 78.4, 71.5, 68.7, 62.1, 40.8, 32.1, 29.2, 23.6, 23.1; HRMS m/z: [M+Na$^+$] for C$_{24}$H$_{30}$ClNO$_6$Na, 486.1659. found, 486.1642.

N-(2-(5-(((3R,4S,5R)-3,4-dihydroxy-5-methoxy-6,6-dimethyltetrahydro-2H-pyran-2-yl)oxy)-3'-(trifluoromethyl)-[1,1'-biphenyl]-2-yl)ethyl)acetamide (11f)

Colorless amorphous solid (52% yield over 2 steps); $^1$H NMR (500 MHz, CDCl$_3$) δ 7.64 (d, 1H, J=7.7 Hz), 7.55 (t, 2H, J=7.6 Hz), 7.49 (m, 1H), 7.23 (d, 1H, J=8.5 Hz), 7.06 (dd, 1H, J=2.7, 8.4 Hz), 6.89 (d, 1H, J=2.7 Hz), 5.56 (d, 1H, J=2.2 Hz), 5.31 (s, 1H), 4.19 (m, 2H), 3.60 (s, 3H), 3.34 (d, 1H, J=9.1 Hz), 3.29 (dd, 2H, J=7.0, 13.3 Hz), 2.72 (t, 2H, J=7.3 Hz), 2.69 (s, 1H), 2.64 (s, 1H), 1.87 (s, 3H), 1.37 (s, 3H), 1.22 (s, 3H); $^{13}$C NMR (125 MHz, CDCl$_3$) δ 170.1, 155.4, 142.1, 141.9, 132.6, 131.0, 130.7 (q, J=31.5 Hz), 129.4, 129.0, 125.9 (q, J=3.6, 7.2 Hz), 125.3, 124.2 (q, J=3.6, 7.2 Hz), 123.1, 118.0, 115.8, 97.9, 84.4, 77.4, 71.4, 68.7, 62.0, 40.6, 32.1, 29.8, 29.2, 23.4, 23.0; HRMS m/z: [M+Na$^+$] for C$_{25}$H$_{30}$F$_3$NO$_6$Na, 520.1923. found, 520.1932. This material was determined to be 97.2% pure (retention time=7.631) by HPLC (Phenomenex Luna C-18, 5 μg, 10×250 mm column eluting with 30% CH$_3$CN, 70% H$_2$O, flow rate 5.0 mL/min).

N-(2-(5-(((3R,4S,5R)-3,4-dihydroxy-5-methoxy-6,6-dimethyltetrahydro-2H-pyran-2-yl)oxy)-4'-(trifluoromethyl)-[1,1'-biphenyl]-2-yl)ethyl)acetamide (11g)

Colorless amorphous solid (49% yield over 2 steps); $^1$H NMR (400 MHz, CDCl$_3$) δ 7.70 (d, J=7.6 Hz, 2H), 7.43 (d, J=7.9 Hz, 2H), 7.24 (d, J=8.4 Hz, 1H), 7.09-7.03 (dd, J=8.6, 2.7 Hz, 1H), 6.90 (d, J=2.7 Hz, 1H), 5.55 (d, J=2.3 Hz, 1H), 5.33 (m, 1H), 4.26-4.11 (m, 2H), 3.60 (s, 3H), 3.36-3.25 (m, 3H), 2.74 (t, J=7.4 Hz, 2H), 2.56 (br s, 20H), 1.88 (s, 3H), 1.37 (s, 3H), 1.22 (s, 3H); $^{13}$C NMR (125 MHz, MeOD) δ 173.1, 156.8, 146.9, 143.2, 132.1, 130.9, 130.7, 130.5, 130.2, 126.3, 126.2, 124.7, 118.5, 116.8, 100.1, 85.3, 79.5, 72.8, 69.5, 62.1, 41.7, 32.9, 29.2, 23.6, 22.5; HRMS m/z: [M+Na$^+$] for C$_{25}$H$_{30}$F$_3$NO$_6$Na, 520.1923. found, 520.1934.

N-(2-(5-(((3R,4S,5R)-3,4-dihydroxy-5-methoxy-6,6-dimethyltetrahydro-2H-pyran-2-yl)oxy)-2'-(methylthio)-[1,1'-biphenyl]-2-yl)ethyl)acetamide (11h)

Colorless amorphous solid (63% yield over 2 steps); $^1$H NMR (400 MHz, CDCl$_3$) δ 7.36 (t, 1H, J=7.0 Hz), 7.27 (m, 3H), 7.09 (m, 1H), 7.01 (m, 1H), 6.87 (s, 1H), 5.64 (s, 1H), 5.54 (m, 1H), 4.16 (m, 2H), 3.32 (d, 2H, J=8.8 Hz), 3.27 (m, 2H), 3.06 (s, 1H), 2.56 (t, 2H, J=6.2 Hz), 2.36 (d, 3H, J=7.6 Hz), 1.83 (s, 3H), 1.33 (s, 3H), 1.20 (s, 3H); $^{13}$C NMR (100 MHz, CDCl$_3$) δ 170.3, 155.1, 155.0, 141.0, 138.9, 130.5, 130.1, 129.8, 128.4, 124.6, 124.2, 118.3, 116.2, 115.9, 97.9, 84.5, 78.3, 71.5, 68.7, 62.0, 53.6, 40.1, 31.7, 29.3, 23.3, 15.3, 15.2; HRMS m/z: [M+Na$^+$] for C$_{25}$H$_{33}$NO$_6$SNa, calcd, 498.1926. found, 498.1925. This material was determined to be 95% pure (retention time=7.465) by HPLC (Phenomenex Luna C-18, 5 μm, 10×250 mm column eluting with 30% CH$_3$CN, 70% H$_2$O, flow rate 5.0 mL/min).

N-(2-(5-(((3R,4S,5R)-3,4-dihydroxy-5-methoxy-6,6-dimethyltetrahydro-2H-pyran-2-yl)oxy)-2'-methoxy-[1,1'-biphenyl]-2-yl)ethyl)acetamide (11i)

Colorless amorphous solid (41% yield over 2 steps); $^1$H NMR (500 MHz, CDCl$_3$) δ 7.36 (ddd, 1H, J=1.8, 7.6, 8.2 Hz), 7.18 (d, 1H, J=8.3 Hz), 7.12 (t, 1H, J=5.8 Hz), 7.02 (m, 3H), 6.87 (dd, 1H, J=2.3, 11.3 Hz), 5.54 (s, 1H), 5.39 (s, 1H), 4.21 (dt, 1H, J=3.3, 9.0 Hz), 4.15 (m, 1H), 3.77 (d, 3H, J=6.9 Hz), 3.60 (s, 3H), 3.33 (d, 1H, J=8.7 Hz), 3.29 (m, 2H), 2.73 (s, 1H), 2.66 (s, 1H), 2.60 (dd, 2H, J=6.5, 12.8 Hz), 1.84 (s, 3H), 1.37 (s, 3H), 1.24 (s, 3H); $^{13}$C NMR (125 MHz, CDCl$_3$) δ 170.0, 156.4, 155.2, 139.9, 131.2, 130.8, 130.2, 130.0, 129.2, 120.9, 118.6, 118.3, 115.7, 115.2, 111.4, 111.2, 98.0, 97.9, 84.5, 78.2, 71.4, 68.7, 62.0, 55.9, 55.9, 40.3, 31.9, 30.2, 29.3, 29.2, 23.4, 23.1; HRMS m/z: [M+$^+$] for C$_{25}$H$_{34}$NO$_7$, calcd, 460.2335. found, 460.2336. This material was determined to be 96.1% pure (retention time=5.057) by HPLC (Phenomenex Luna C-18, 5 μm, 10×250 mm column eluting with 30% CH$_3$CN, 70% H$_2$O, flow rate 5.0 mL/min).

N-(2-(5-(((3R,4S,5R)-3,4-dihydroxy-5-methoxy-6,6-dimethyltetrahydro-2H-pyran-2-yl)oxy)-3'-methoxy-[1,1'-biphenyl]-2-yl)ethyl)acetamide (11j)

Colorless amorphous solid (53% yield over 2 steps); $^1$H NMR (400 MHz, CDCl$_3$) δ 7.31 (t, 1H, J=7.9 Hz), 7.17 (d, J=8.5 Hz, 1H), 7.02-6.96 (dd, J=8.5, 2.7 Hz, 1H), 6.92-6.83 (m, 4H), 6.81 (d, J=1.5 Hz, 2H), 5.54 (d, J=2.2 Hz, 1H), 5.45 (s, 1H), 4.25-4.16 (dd, J=9.1, 3.2 Hz, 1H), 4.17-4.10 (dd, J=3.3, 2.2 Hz, 1H), 3.82 (s, 3H), 3.58 (s, 3H), 3.39-3.20 (m, 3H), 3.24 (br s, OH), 2.97 (br s, OH), 2.75 (t, J=7.1 Hz, 2H), 1.85 (s, 3H), 1.35 (s, 3H), 1.20 (s, 3H); $^{13}$C NMR (125 MHz, CDCl$_3$) δ 170.4, 159.5, 155.3, 143.3, 142.8, 130.8, 129.5, 129.5, 121.7, 118.0, 115.3, 115.1, 112.7, 98.1, 84.5, 78.4, 71.5, 68.7, 62.0, 55.4, 40.9, 32.0, 29.1, 23.4, 23.1; HRMS m/z: [M+H$^+$] for C$_{25}$H$_{34}$NO$_7$, calcd, 460.2335. found, 460.2322.

N-(2-(5-(((3R,4S,5R)-3,4-dihydroxy-5-methoxy-6,6-dimethyltetrahydro-2H-pyran-2-yl)oxy)-3'-methyl-[1,1'-biphenyl]-2-yl)ethyl)acetamide (11k)

Colorless amorphous solid (44% yield over 2 steps); $^1$H NMR (400 MHz, CDCl$_3$) δ 7.32-7.27 (m, 1H), 7.16 (d, J=6.6 Hz, 2H), 7.10-7.04 (m, 2H), 6.99 (d, J=8.5 Hz, 1H), 6.88 (s, 1H), 5.55 (s, 1H), 5.41 (s, 1H), 4.25-4.08 (m, 2H), 3.57 (s, 3H), 3.37-3.20 (m, 5H), 2.75 (t, J=7.0 Hz, 2H), 2.39 (s, 3H), 1.83 (s, 3H), 1.35 (s, 3H), 1.20 (s, 3H); $^{13}$C NMR (100 MHz, CDCl$_3$) δ 170.4, 155.3, 143.6, 141.3, 138.1, 130.8, 130.0, 129.5, 128.3, 128.1, 126.3, 118.1, 115.1, 98.1, 84.5, 78.4, 71.5, 68.7, 62.0, 40.9, 32.0, 29.2, 23.4, 23.1, 21.7; HRMS m/z: [M+H$^+$] for C$_{25}$H$_{33}$NO$_6$Na, calcd, 466.2206. found, 466.2203.

N-(2-(5-(((3R,4S,5R)-3,4-dihydroxy-5-methoxy-6,6-dimethyltetrahydro-2H-pyran-2-yl)oxy)-3'-(morpholinomethyl)-[1,1'-biphenyl]-2-yl)ethyl)acetamide (11l)

Colorless amorphous solid (47% yield over 2 steps); $^1$H NMR (500 MHz, CDCl$_3$) δ 7.41-7.29 (m, 2H), 7.27 (m, 1H), 7.19 (d, J=8.1 Hz, 2H), 7.04-6.99 (dd, J=8.5, 2.7 Hz, 1H), 6.91 (d, J=2.7 Hz, 1H), 5.55 (d, J=2.4 Hz, 1H), 5.35 (s, 1H), 4.26-4.18 (dd, J=9.0, 3.3 Hz, 1H), 4.15 (t, J=2.8 Hz, 1H), 3.72 (t, J=4.7 Hz, 4H), 3.59 (s, 3H), 3.56 (s, 2H), 3.34 (d, J=9.0 Hz, 1H), 3.30-3.21 (q, J=6.7 Hz, 2H), 2.75 (t, J=7.1 Hz, 2H), 2.58-2.41 (m, 6H), 1.85 (s, 3H), 1.36 (s, 3H), 1.23 (s, 3H); $^{13}$C NMR (125 MHz, CDCl$_3$) δ 155.4, 143.4, 141.5, 137.8, 130.9, 130.1, 129.6, 128.5, 128.3, 128.2, 118.2, 115.3, 98.1, 84.6, 78.4, 71.5, 68.8, 67.1, 63.5, 62.0, 53.8, 40.7, 32.2, 29.2, 23.5, 23.2; HRMS (FAB) m/z: [M+Na$^+$] for C$_{29}$H$_{40}$N$_2$O$_7$Na, calcd, 551.2728. found, 551.2734.

N-(2-(5-(((3R,4S,5R)-3,4-dihydroxy-5-methoxy-6,6-dimethyltetrahydro-2H-pyran-2-yl)oxy)-4'-hydroxy-[1,1'-biphenyl]-2-yl)ethyl)acetamide (11m)

After cyclic carbonate hydrolysis following the same procedure as compound 11a-p, the crude TBS protected compound was dissolved in THF (2 mL) and tertrabutylammonium fluoride (1.5 eq.) was added dropwise at 0° C. under argon atmosphere. After 1 h the reaction was quenched with water and extracted with EtOAc (3×10 mL); combined organic fractions were washed with saturated aqueous sodium chloride, dried over anhydrous Na$_2$SO$_4$, filtered and concentrated. The residue was purified by column chromatography (SiO$_2$; 10:1, DCM:acetone) to afford acetamide 11m as a amorphous solid (40% yield over 3 steps). $^1$H NMR (500 MHz, MeOD) δ 7.20 (d, J=8.4 Hz, 1H), 7.15-7.08 (d, J=8.4 Hz, 2H), 6.96 (dd, J=8.4, 2.6 Hz, 1H), 6.85-6.79 (m, 3H), 5.45 (d, J=2.4 Hz, 1H), 4.12 (m, J=9.3, 3.3 Hz, 1H), 3.96 (t, J=2.8 Hz, 1H), 3.59 (s, 3H), 3.21 (d, J=9.3 Hz, 1H), 3.16 (dd, J=8.5, 6.5 Hz, 2H), 2.70 (dd, J=8.5, 6.5 Hz, 2H), 1.84 (s, 3H), 1.32 (s, 3H), 1.18 (s, 3H); $^{13}$C NMR (125 MHz, MeOD) δ 173.1, 157.7, 156.6, 144.7, 134.0, 131.7, 131.2, 131.1, 118.9, 116.0, 115.7, 100.1, 85.4, 79.4, 72.8, 69.5, 62.1, 41.8, 33.0, 29.2, 23.6, 22.5; HRMS (FAB) m/z: [M+Na$^+$] for C$_{24}$H$_{31}$NO$_7$Na, calcd, 468.1998. found, 468.1999.

N-(2-(benzo[d][1,3]dioxol-5-yl)-4-(((3R,4S,5R)-3,4-dihydroxy-5-methoxy-6,6-dimethyltetrahydro-2H-pyran-2-yl)oxy)phenethyl)acetamide (11n)

Colorless amorphous solid (51% yield over 2 steps); $^1$H NMR (500 MHz, CDCl$_3$) δ 7.15 (d, J=8.5 Hz, 1H), 7.00-6.96 (dd, J=8.5, 2.7 Hz, 1H), 6.88 (d, J=2.6 Hz, 1H), 6.84 (d, J=7.9 Hz, 1H), 6.76 (d, J=1.6 Hz, 1H), 6.74-6.69 (m, 1H), 6.01 (s, 2H), 5.54 (d, J=2.4 Hz, 1H), 5.40 (s, 1H), 4.21 (dd, J=9.1, 3.3 Hz, 1H), 4.14 (t, J=2.7 Hz, 2H), 3.58 (s, 3H), 3.33 (d, J=9.1 Hz, 1H), 3.30-3.23 (q, J=6.9 Hz, 2H), 3.11 (br s, OH), 2.92 (br s, OH), 2.74 (t, J=7.2 Hz, 2H), 1.86 (s, 3H), 1.34 (s, 3H), 1.20 (s, 3H); $^{13}$C NMR (125 MHz, CDCl$_3$) δ 170.2, 155.4, 147.7, 147.0, 143.1, 135.3, 130.8, 129.7, 122.6, 118.3, 115.2, 109.9, 108.4, 101.3, 98.1, 84.6, 78.4, 71.5, 68.8, 62.0, 40.8, 32.1, 29.2, 23.4, 23.2; HRMS (FAB) m/z: [M+Na$^+$] for C$_{25}$H$_{31}$NO$_8$Na, calcd, 496.1947. found, 496.1940. This material was determined to be 98.4% pure (retention time=4.384) by HPLC (Phenomenex Luna C-18, 5 μm, 10×250 mm column eluting with 40% CH$_3$CN, 60% H$_2$O, flow rate 5.0 mL/min).

N-(4-(((3R,4S,5R)-3,4-dihydroxy-5-methoxy-6,6-dimethyltetrahydro-2H-pyran-2-yl)oxy)-2-(pyridin-3-yl)phenethyl)acetamide (11o)

Colorless amorphous solid (37% yield over 2 steps); $^1$H NMR (500 MHz, CDCl$_3$) δ 8.55 (d, J=3.9 Hz, 1H), 8.49 (s, 1H), 7.60 (m, 1H), 7.35 (dd, J=7.8, 4.5 Hz, 1H), 7.20 (d, J=8.5 Hz, 1H), 7.05-6.99 (dd, J=8.4, 2.7 Hz, 1H), 6.85 (d, J=2.6 Hz, 1H), 5.52 (d, J=2.4 Hz, 1H), 5.36 (s, 1H), 4.14 (dd, J=3.4, 9.1 Hz, 1H), 4.10 (t, J=2.7 Hz, 1H), 3.59 (s, 3H), 3.31 (d, J=9.0 Hz, 1H), 3.27-3.20 (m, 2H), 2.68 (t, J=7.3 Hz, 2H), 1.86 (s, 3H), 1.33 (s, 3H), 1.17 (s, 3H); $^{13}$C NMR (125 MHz, CDCl$_3$) δ 170.2, 155.5, 149.8, 148.7, 139.5, 136.8, 131.1, 131.0, 130.6, 129.8, 123.4, 118.3, 118.2, 116.1, 98.0, 84.5, 78.5, 71.4, 68.7, 62.1, 40.7, 32.2, 29.2, 23.5, 23.1; HRMS (FAB) m/z: [M+Na$^+$] for C$_{23}$H$_{31}$N$_2$O$_6$, calcd, 431.2182. found, 431.2194.

N-(4-(((3R,4S,5R)-3,4-dihydroxy-5-methoxy-6,6-dimethyltetrahydro-2H-pyran-2-yl)oxy)-2-(pyridin-4-yl)phenethyl)acetamide (11p)

Colorless amorphous solid (42% yield over 2 steps); $^1$H NMR (400 MHz, CDCl$_3$) δ 8.73-8.63 (dd, J=5.7, 3.9 Hz, 2H), 7.27-7.23 (m, 3H), 7.11-7.03 (m, 1H), 6.86 (t, J=2.8 Hz, 1H), 5.55 (d, J=2.3 Hz, 1H), 5.41-5.31 (m, 2H), 4.26-4.13 (m, 2H), 4.05 (d, J=6.9 Hz, 1H), 3.61 (s, 3H), 3.36-3.25 (m, 2H), 2.78-2.71 (dd, J=8.3, 6.8 Hz, 2H), 1.90 (s, 3H), 1.39 (s, 3H), 1.24 (s, 3H); $^{13}$C NMR (125 MHz, CDCl$_3$) δ 170.1, 155.5, 149.8, 140.5, 131.4, 129.1, 124.4, 117.9, 116.3, 98.0, 94.1, 84.5, 71.5, 71.4, 68.7, 62.1, 40.7, 32.2, 29.2, 28.8, 23.5, 23.1, 18.7; HRMS (FAB) m/z: [M+Na$^+$] for C$_{23}$H$_{30}$N$_2$O$_6$Na, calcd, 453.2001. found, 453.1972.

Example 11

(Z)-4-(benzyloxy)-2-(methoxymethoxy)-1-(2-nitrovinyl)benzene (14)

Nitromethane (11.5 mL) was added to a mixture of aldehyde 13 (1.24g, 4.6 mmol) and ammonium acetate (0.63 g, 8.2 mmol) and heated to 50° C. Upon completion (20 min), the reaction mixture was cooled to RT and purified without work-up by column chromatography (SiO$_2$, 4:1, Hex:EtOAc) to afford nitrostyrene 14 as a clear, colorless oil (1.22 g, 3.87 mmol, 84%). $^1$H NMR (400 MHz, CDCl$_3$) δ 8.17 (d, J=13.4 Hz, 1H), 7.80 (d, J=13.6 Hz, 1H), 7.50-7.32 (m, 6H), 6.88 (d, J=2.5 Hz, 1H), 6.67 (m, 1H), 5.30 (s, 2H), 5.12 (s, 2H), 3.52 (s, 3H); $^{13}$C NMR (100 MHz, CDCl$_3$) δ 163.4, 159.0, 136.1, 136.0, 135.6, 133.5, 128.8, 128.5, 127.7, 127.7, 113.0, 108.6, 102.2, 94.7, 70.5, 56.6; HRMS (FAB) m/z: [M+Na$^+$] for C$_{17}$H$_{17}$NO$_5$Na, calcd, 338.1004. found, 338.1007.

Example 12

4'-(benzyloxy)-2'-(methoxymethoxy)-2-nitro-1,2,3,6-tetrahydro-1,1'-biphenyl (15)

Nitrostyrene 14 (0.65 g, 2.06 mmol) was dissolved in toluene (0.6 mL) in a 2 mL sealed tube and cooled to −78° C. Butadiene was bubbled into the solution to double the volume and then the tube was sealed and heated to reflux for 48 h. To prevent bumping of the butadiene gas, the tube was cooled again to −78° C. and used directly in purification by column chromatography (SiO$_2$; 3:1, Hex:EtOAc) to afford cyclohexene 15 (0.72 g, 1.96 mmol, 95%). $^1$H NMR (500 MHz, CDCl$_3$) δ 7.40 (m, 4H), 7.36-7.28 (m, 2H), 7.06 (d, J=8.4 Hz, 1H), 6.80 (d, J=2.4 Hz, 1H), 6.56 (dd, J=8.4, 2.5 Hz, 1H), 5.86-5.77 (m, 1H), 5.71 (ddd, J=9.8, 5.1, 2.3 Hz, 1H), 5.27-5.20 (m, 1H), 5.20 (s, 2H), 5.00 (s, 2H), 3.70 (dt, J=17.0, 8.7 Hz, 1H), 3.49 (s, J=12.7 Hz, 3H), 2.84-2.74 (m, 1H), 2.71 (ddd, J=13.2, 8.4, 1.5 Hz, 1H), 2.45 (m, 2H); $^{13}$C NMR (125 MHz, CDCl$_3$) δ 159.2, 156.1, 136.9, 129.3, 128.6, 127.0, 122.5, 120.9, 107.8, 120.6, 94.6, 85.6, 70.1, 31.5, 31.3, 29.7.

Example 13

N-(4'-(benzyloxy)-2'-(methoxymethoxy)-1,2,3,6-tetrahydro-[1,1'-biphenyl]-2-yl)acetamide (16)

Nitro compound 13 (0.23 g, 0.62 mmol) was dissolved in isopropanol (12.4 mL) and aqueous 1M HCl (6.2 mL). Zinc dust (811 mg, 12.4 mmol) was added and the mixture was stirred vigorously for 1.5 h at 50° C. After cooling to room temperature, saturated NaHCO3 (8 mL) was added and the resulting mixture was stirred for an additional 20 min. The solids were removed by filtration and the remaining solution was extracted with DCM (3×20 mL). The organic layers were combined and washed with saturated aqueous sodium chloride solution, dried (Na$_2$SO$_4$) and concentrated to afford amine as clear, colorless oil (0.20 g, 0.59 mmol, 95%).

Acetic anhydride (62 μL, 0.65 mmol) and triethylamine (95 μL, 0.68 mmol) were added to a solution of the amine (0.62 mmol) in DCM (6.2 mL) under an atmosphere at RT. After 3 h the reaction was quenched with saturated aqueous ammonium chloride and extracted with DCM (3×10 mL); combined organic fractions were washed with Brine, dried (Na$_2$SO$_4$), filtered and concentrated. The residue was purified by column chromatography (SiO$_2$; 3:1, Hex:EtOAc) to afford acetamide 16 (0.17 g, 0.46 mmol, 74%). $^1$H NMR (500 MHz, CDCl$_3$) δ 7.42 (d, J=7.8 Hz, 2H), 7.39-7.33 (t, J=7.2 Hz, 2H), 7.33-7.28 (m, 1H), 7.12 (d, J=8.5 Hz, 1H), 6.77 (s, 1H), 6.63 (d, J=8.5 Hz, 1H), 5.90 (d, J=8.4 Hz, 1H), 5.71 (d, J=36.2 Hz, 2H), 5.17 (s, 2H), 5.02 (s, 2H), 4.36-4.23 (dtd, J=13.8, 10.4, 9.9, 7.2 Hz, 1H), 3.50 (s, 3H), 3.31-3.22 (dd, J=18.6, 7.9 Hz, 1H), 2.59 (d, J=17.3 Hz, 1H), 2.33 (s, 2H), 2.02-1.93 (m, 1H), 1.74 (s, 3H); $^{13}$C NMR (125 MHz, CDCl$_3$) δ 169.8, 158.3, 156.1, 136.9, 128.5, 128.3, 127.9, 127.6, 126.7, 125.0, 124.4, 108.0, 102.9, 95.6, 70.0, 56.2, 48.8, 37.4, 33.0, 32.6, 23.1; HRMS (FAB) m/z: [M+Na$^+$] for C$_{23}$H$_{27}$NO$_4$Na, calcd, 404.1832. found, 404.1827.

Example 14

N-(4'-(benzyloxy)-2'-hydroxy-1,2,3,6-tetrahydro-[1,1'-biphenyl]-2-yl)acetamide Catalytic amount of conc. HCl (few drops) was added to MOM protected phenol 16 (0.27 g, 0.71 mmol) in methanol (7.1 mL) and stirred vigorously at 50° C. for overnight. Upon completion the reaction mixture was concentrated and was purified by column chromatography (SiO$_2$; 5:100, MeOH:DCM) to afford phenol (0.19 g, 0.58 mmol, 81%). $^1$H NMR (400 MHz, CDCl$_3$) δ 8.86 (s, 1H), 7.41-7.25 (m, 5H), 7.01 (d, J=8.5 Hz, 1H), 6.73 (d, J=2.4 Hz, 1H), 6.48 (d, J=6.0 Hz, 1H), 5.73 (m, 1H), 5.65 (m, 1H), 4.96 (s, 2H), 4.26 (m, 1H), 3.42 (m, 1H), 2.55-2.12 (m, 4H), 1.98 (s, 3H); $^{13}$C NMR (100 MHz, CDCl$_3$) δ 173.2, 158.3, 155.4, 136.9, 128.5, 128.0, 127.9, 127.6, 127.0, 123.9, 121.1, 107.2, 103.4, 69.9, 51.9, 50.0, 36.6, 31.6, 21.0; HRMS (FAB) m/z: [M+Na$^+$] for C$_{21}$H$_{23}$NO$_3$Na, calcd, 360.1576. found, 360.1571.

Example 15

2'-acetamido-4-(benzyloxy)-1',2',3',6'-tetrahydro-[1,1'-biphenyl]-2-yl trifluoromethanesulfonate (17)

A solution of phenol (0.19 g, 0.58 mmol) in anhydrous DCM (5.8 mL) was stirred at 0° C. and triethylamine (0.12 mL, 0.87 mmol) was added followed by N-phenyl-bis(trifluoromethanesulfonimide) (0.31 g, 0.87 mmol). Upon completion the reaction was quenched by addition of water (50 mL), washed with saturated aqueous NaCl solution, dried (Na$_2$SO$_4$), filtered and concentrated. The residue was purified by column chromatography (SiO$_2$, 3:1, Hex:EtOAc) to afford triflate 17 as a clear, yellow oil (0.23 g, 0.49 mmol, 85%). $^1$H NMR (400 MHz, CDCl$_3$) δ 7.45-7.31 (m, 6H), 7.00 (d, J=11.2 Hz, 1H), 6.84 (d, J=2.4 Hz, 1H), 5.70 (m, 2H), 5.60 (d, J=9.3 Hz, 1H), 5.04 (s, 2H), 4.53-4.38 (dt, J=15.2, 10.2 Hz, 1H), 3.18-3.03 (td, J=11.2, 5.2 Hz, 1H), 2.63-2.50 (dd, J=16.2, 4.2 Hz, 1H), 2.42-2.32 (m, 1H), 2.28-2.15 (m, 1H), 2.11-1.97 (t, J=14.5 Hz, 1H), 1.71 (s, 3H); $^{13}$C NMR (100 MHz, CDCl$_3$) δ 169.7, 158.2, 147.6, 136.0, 129.9, 128.8, 128.5, 128.1, 127.7, 126.1, 125.4, 115.8, 108.2, 70.7, 48.3, 38.5, 34.8, 33.7, 23.2; HRMS (FAB) m/z: [M+Na$^+$] for C$_{22}$H$_{22}$F$_3$NO$_5$SNa, calcd, 492.106318. found, 492.1067.

Example 16

N-(4'-(benzyloxy)-3"-fluoro-1,2,3,6-tetrahydro-[1,1':2',1"-terphenyl]-2-yl)acetamide (18a)

Followed same Suzuki coupling procedure as described above for 6a-p. $^1$H NMR (400 MHz, CDCl$_3$) δ 7.47-7.30 (m, 7H), 7.13-7.05 (t, J=8.9 Hz, 1H), 7.05-7.00 (t, J=7.2 Hz, 2H), 6.97 (d, J=10.9 Hz, 1H), 6.80 (d, J=2.7 Hz, 1H), 5.72-5.53 (m, 2H), 5.06 (s, 2H), 4.91 (d, J=8.7 Hz, 1H), 4.36-4.24 (m, 1H), 2.90-2.75 (dd, J=19.2, 8.2 Hz, 1H), 2.59-2.45 (dt, J=16.3, 4.4 Hz, 1H), 2.36 (m, 2H), 1.75 (s, 3H); $^{13}$C NMR (100 MHz, CDCl$_3$) δ 169.3, 156.8, 143.9, 142.3, 137.0, 132.6, 130.2, 130.2, 128.8, 128.5, 128.2, 127.8, 126.7, 125.2, 125.0, 116.4, 116.2, 116.0, 115.2, 114.5, 114.3, 70.2, 49.4, 40.5, 35.3, 33.4, 23.5; HRMS (FAB) m/z: [M+Na$^+$] for C$_{27}$H$_{26}$FNO$_2$Na, calcd, 438.1840. found, 438.1818.

N-(4'-(benzyloxy)-3"-(trifluoromethyl)-1,2,3,6-tetrahydro-[1,1':2',1"-terphenyl]-2-yl)acetamide (18b)

Followed same Suzuki coupling procedure as described above for 6a-p. $^1$H NMR (400 MHz, CDCl$_3$) δ 7.73-7.30 (m, 10H), 7.05 (d, J=8.7 Hz, 1H), 6.85 (s, 1H), 5.66 (m, 2H), 5.16 (d, J=8.5 Hz, 1H), 5.08 (s, 2H), 4.43-4.29 (m, 1H), 2.90-2.74 (q, J=10.0, 9.0 Hz, 1H), 2.50 (d, J=17.7 Hz, 1H), 2.40-2.28 (dd, J=6.9, 3.9 Hz, 2H), 1.75 (s, 3H); $^{13}$C NMR (101 MHz, CDCl$_3$) δ 169.7, 156.9, 142.4, 141.9, 136.9, 132.6, 131.1, 130.8, 129.1, 128.7, 128.6, 128.2, 127.7, 126.6, 126.0, 125.9, 125.0, 124.3, 124.2, 116.3, 115.3, 70.2, 49.4, 40.6, 35.2, 33.1, 23.4; HRMS (FAB) m/z: [M+Na$^+$] for C$_{28}$H$_{26}$F$_3$NO$_2$Na, calcd, 488.1813. found, 488.1812.

Example 17

N-(3"-fluoro-4'-hydroxy-1,2,3,6-tetrahydro-[1,1':2',1"-terphenyl]-2-yl)acetamide (19a)

1,2-Ethanedithiol (0.22 mL, 2.66 mmol) and BF$_3$OEt$_2$ (0.176 mL, 1.4 mmol) were added to benzyl ether 18a (64 mg, 0.14 mmol) in DCM (1.8 mL). After 8 h, reaction mixture was concentrated and purified by column chromatography (SiO$_2$, 10:100, MeOH:DCM) to afford phenol 19a as an amorphous solid (45 mg, 0.12 mmol, 86%) $^1$H NMR (500 MHz, CDCl$_3$) δ 8.98 (s, 1H), 7.40-7.34 (q, J=7.1, 6.2 Hz, 1H), 7.27 (d, J=7.6 Hz, 1H), 7.10-7.01 (m, 2H), 6.96 (d, J=9.4 Hz, 1H), 6.84-6.79 (dd, J=8.5, 2.6 Hz, 1H), 6.68 (d, J=2.6 Hz, 1H), 5.73-5.52 (m, 2H), 4.51-4.38 (dt, J=9.9, 5.0 Hz, 1H), 2.88-2.77 (q, J=9.5, 7.9 Hz, 1H), 2.43 (d, J=17.3 Hz, 1H), 2.34 (m, 2H), 2.18 (s, 1H), 1.77 (s, 3H); $^{13}$C NMR (125 MHz, CDCl$_3$) δ 170.5, 163.6-161.7 (d, J=244.0 Hz), 155.2, 144.2 (d, J=7.6 Hz), 142.3, 130.8, 130.1 (d, J=8.4 Hz), 128.2, 127.0, 125.0 (d, J=2.2 Hz), 124.7, 116.5, 116.3 (d, J=20.3 Hz), 115.9, 114.2 (d, J=20.3 Hz), 49.6, 40.8, 35.5, 33.5, 23.2; HRMS (FAB) m/z: [M+Na$^+$] for C$_{21}$H$_{25}$FNO$_2$Na, 348.1376. found, 348.1379.

N-(4'-hydroxy-3"-(trifluoromethyl)-1,2,3,6-tetrahydro-[1,1':2',1"-terphenyl]-2-yl)acetamide (19b)

Followed same procedure as for 19a. $^1$H NMR (400 MHz, CDCl$_3$) δ 9.20 (s, 1H), 7.66-7.56 (m, 4H), 7.29 (d, J=8.5 Hz, 1H), 6.82-6.72 (d, J=10.5 Hz, 1H), 6.65 (s, 1H), 5.65 (m, 1H), 5.54 (m, 1H), 5.21 (d, J=9.7 Hz, 2H), 4.56-4.33 (m, 1H), 2.76-2.61 (m, 1H), 2.46-2.24 (m, 3H), 1.75 (s, 3H); $^{13}$C NMR (100 MHz, CDCl$_3$) δ 170.5, 155.3, 142.7, 142.0, 132.6, 130.8, 130 (q, J=32.5 Hz), 128.8, 128.4, 126.9, 126.0 (m), 124.7, 124.0 (m), 116.7, 116.0, 49.6, 40.9, 35.6, 33.5, 23.2; HRMS (FAB) m/z: [M+Na$^+$] for C$_{21}$H$_{20}$F$_3$NO$_2$Na, calcd, 398.1344. found, 398.1346.

Example 18

N-(4'-(((3R,4S,5R)-3,4-dihydroxy-5-methoxy-6,6-dimethyltetrahydro-2H-pyran-2-yl)oxy)-3"-fluoro-1,2,3,6-tetrahydro-[1,1':2',1"-terphenyl]-2-yl)acetamide (20a)

Followed same noviose coupling procedure as described above for 11a-p to afford 20a as a inseparable mixture of diastereomers. $^1$H NMR (500 MHz, CDCl$_3$) δ 7.32 (ddd, 1H, J=6.0, 7.9, 13.9 Hz), 7.22 (dd, 1H, J=2.8, 8.7 Hz), 7.00 (m, 2H), 6.94 (d, 1H, J=7.6 Hz), 6.87 (m, 1H), 6.77 (dd, 1H, J=2.7, 8.7 Hz), 5.59 (m, 1H), 5.52 (m, 1H), 5.49 (d, ½H, J=2.4 Hz), 5.45 (d, ½H, J=2.4 Hz), 4.81 (dd, 1H, J=2.5, 8.8 Hz), 4.21 (m, 1H), 4.12 (m, 1H), 4.07 (m, 1H), 3.52 (s, 3H), 3.25

(dd, 1H, J=0.9, 9.0 Hz), 2.89 (br s, 1H), 2.76 (m, 1H), 2.67 (s, 1H), 2.26 (m, 2H), 1.69 (m, 1H), 1.65 (s, 3/2H), 1.64 (s, 3/2H), 1.29 (s, 3/2H), 1.28 (s, 3/2H), 1.13 (s, 3/2H), 1.12 (s, 3/2H); $^{13}$C NMR (125 MHz, CDCl$_3$) δ 169.4, 169.4, 163.7-161.7 (d, J=249.0 Hz), 154.9, 154.7, 143.0 (dd, J=1.7, 8.5 Hz), 142.2 (d, J=1.7 Hz), 133.4, 133.3, 130.2 (dd, J=1.7, 8.5 Hz), 128.4 (d, J=5.0 Hz), 126.6 (d, J=3.2 Hz), 125.1 (d, J=3.6 Hz), 125.0 (m), 117.2, 116.9, 116.6, 116.3 (dd, J=13.4, 20.9 Hz), 116.2, 114.3 (dd, J=1.5, 20.9 Hz), 98.0, 97.7, 84.5, 84.4, 78.3, 78.3, 77.4, 71.5, 71.4, 68.8, 62.0, 61.9, 49.6, 49.6, 40.5, 40.5, 35.2, 35.1, 33.4, 29.2, 23.6, 23.5, 23.2, 23.1; HRMS (FAB) m/z: [M+Na$^+$] for C$_{28}$H$_{34}$FNO$_6$Na, 522.2262. found, 522.2267.

N-(4'-(((3R,4S,5R)-3,4-dihydroxy-5-methoxy-6,6-dimethyltetrahydro-2H-pyran-2-yl)oxy)-3''-(trifluoromethyl)-1,2,3,6-tetrahydro-[1,1':2',1''-terphenyl]-2-yl)acetamide (20b)

Followed same noviose coupling procedure as described above for 11a-p to afford 20b as a inseparable mixture of diastereomers. $^1$H NMR (500 MHz, CDCl$_3$) δ 7.65 (d, 1H, J=8.2 Hz), 7.56 (t, 1H, J=7.7 Hz), 7.49 (s, 1H), 7.45 (d, 1H, J=7.6 Hz), 7.32 (dd, 1H, J=3.0, 8.7 Hz), 7.08 (td, 1H, J=2.7, 8.6 Hz), 6.85 (dd, 1H, J=2.7, 8.5 Hz), 5.65 (m, 1H), 5.59 (m, 1H), 5.57 (d, ½H, J=2.4 Hz), 5.53 (d, ½H, J=2.3 Hz), 4.90 (t, 1H, J=8.2 Hz), 4.30 (m, 1H), 4.19 (dd, 1H, J=4.3, 8.2 Hz), 4.14 (m, 1H), 3.59 (s, 3/2H), 3.59 (s, 3/2H), 3.33 (d, 1H, J=9.0 Hz), 3.17 (s, 1H), 2.95 (s, 1H), 2.76 (m, 1H), 2.49 (m, 1H), 2.33 (m, 1H), 1.74 (m, 1H), 1.73 (s, 3/2H), 1.72 (s, 3/2H), 1.36 (s, 3/2H), 1.35 (s, 3/2H), 1.21 (s, 3/2H), 1.20 (s, 3/2H); $^{13}$C NMR (100 MHz, CDCl$_3$) δ 169.4, 169.4, 155.0, 154.8, 142.3, 141.8, 133.4, 133.3, 132.8, 132.6, 131.8 (dq, J=2.2, 32.5 Hz), 129.1, 128.6, 126.5, 125.9 (q, J=3.2, 7.0 Hz), 125.0, 124.2, 117.6, 117.0, 116.8, 98.1, 97.8, 84.5, 84.4, 78.4, 78.3, 71.3, 71.3, 68.7, 68.7, 61.9, 61.9, 49.4, 49.3, 40.5, 40.5, 35.1, 35.0, 33.1, 29.0, 29.0, 23.4, 23.4, 23.1, 23.0; HRMS (FAB) m/z: [M+Na$^+$] for C$_{29}$H$_{34}$F$_3$NO$_6$Na, Calcd, 572.2230. found, 572.2227.

Example 19

Synthesis of carbocyclic analogue N-(2-(5-((4-(benzyloxy)cyclohexyl)oxy)-3'-fluoro-[1,1'-biphenyl]-2-yl)ethyl)acetamide (24)

4-hydroxycyclohexyl 4-methylbenzenesulfonate (21)

To a solution of pyridine (4 g, 0.025 mol) in CHCl$_3$ (25 mL) was added Cyclohexanediol (2.5 g, 0.021 mol) at room temperature. This was then cooled to 0° C., and tosyl chloride (4.1 g, 0.021) added to the mixture. The reaction was stirred for 16 h under argon at room temperature. Upon completion of the reaction from TLC, the reaction mixture was poured into dilute HCl, and the solid precipitate collected by filtration, washed with water and dried (Na$_2$SO$_4$).

4-(benzyloxy)cyclohexyl 4-methylbenzenesulfonate (22)

To a solution of 21 (0.5 mg, 1.8 mmol) in acetonitrile (3 mL) was added sodium hydride (0.11 g, 2.7 mmol) at 0° C. A solution of benzyl bromide (0.48 mL, 2 mmol) in acetonitrile (2 mL) was then added to the mixture dropwise, under an argon atmosphere. The reaction was stirred for 16 h at room temperature. Upon completion, distilled water (10 mL) was added to the mixture and the organic layer extracted into ethyl acetate. The organic layers were combined, dried and concentrated to give a crude mixture that was purified by column chromatography (Silica gel, 10%-20% EtOAc in hexane) to give 22 (300 mg) as a white solid.

N-(2-(5-((4-(benzyloxy)cyclohexyl)oxy)-3'-fluoro-[1,1'-biphenyl]-2-yl)ethyl)acetamide (24)

To a solution of phenol 23 (45 mg, 0.16 mmol) in DMF (1 mL) was added potassium carbonate (30 mg, 0.19 mmol) and stirred at room temperature for 30 min, after which 22 (75 mg, 0.19 mmol) and TBAI (7 mg, 0.016 mmol) were added to the solution, and heated to reflux overnight. Upon completion, distilled water (5 mL) was added to the mixture and the organic layer extracted into ethyl acetate. After removal of the solvent on a rotor evaporator, the crude mixture was purified by column chromatography (Silica gel, 40% EtOAc in hexane) to give 24 (8 mg) as a white solid.

Synthesis of Phenol Core Intermediate 23

4-(benzyloxy)-2-hydroxybenzaldehyde (25)

2,4-dihydroxybenzaldehyde (10 g, 0.072 mol) was dissolved in acetonitrile (83 mL). To this solution was added NaHCO$_3$ (9.1 g, 0.10 mol) and stirred for 5 min. Benzyl bromide (12.9 mL, 0.10 mol) was added in under an argon atmosphere. The reaction was heated to reflux for 16 h. After cooling to room temperature, the reaction was quenched by addition of distilled water, and the organic layer extracted into dichloromethane (3×50 mL), and organic layers combined, washed with water and brine, dried (Na$_2$SO$_4$) and concentrated. The crude mixture was purified by column chromatography (Silica gel, 10%-20% EtOAc in hexane) to give 25 in 65% yield.

5-(benzyloxy)-2-formylphenyl trifluoromethanesulfonate (26)

A solution of 25 (1.1 g, 4.9 mmol) in freshly distilled dichloromethane (10 mL) was stirred at 0° C. Triethylamine (1.02 mL, 7.35 mmol) was added to this solution followed by triflic anhydride (1.38 mL, 6.35 mmol) over 5 min. Upon completion of the reaction from TLC, the reaction was quenched by addition of distilled water and extracted into dichloromethane (3×10 mL). The organic layers were combined and dried (Na$_2$SO$_4$). After removal of the solvent on a rotor evaporator, the crude brown mixture was purified by column chromatography (Silica gel, 10% EtOAc in hexane) to give 26 in 55% yield.

5-(benzyloxy)-3'-fluoro-[1,1'-biphenyl]-2-carbaldehyde (27)

A solution of 26 (246 mg, 0.68 mmol), boronic acid (92 mg, 0.75 mmol), Pd(PPh$_3$)$_4$ (70.4 mg, 0.068 mmol) and K$_2$CO$_3$ (0.169 g, 1.2 mmol) in anhydrous DMF (7 mL) in a sealed tube, was degassed with argon for 10 minutes at room temperature. After this, the reaction mixture was heated to reflux for 16 h. Upon completion of the reaction from TLC, the reaction was cooled to room temperature and quenched by addition of saturated NaHCO$_3$ and extracted into ethyl acetate (3×5 mL). The organic layers were combined and washed with brine, dried (Na$_2$SO$_4$), and concentrated. The crude brown mixture was purified by column chromatography (Silica gel, 20% EtOAc in hexane) to give the desired product.

(E)-5-(benzyloxy)-3'-fluoro-2-(2-nitrovinyl)-1,1'-biphenyl (28)

0.37 g, 1.2 mmol of 7 was added to a flask containing 3.3 mL nitromethane. Ammonium acetate (1.8 g, 2.2 mmol) was added to the solution and the resulting mixture stirred at 50° C. until the reaction was complete as evidenced by the disappearance of starting material on TLC. The reaction mixture was then cooled to room temperature and purified by silica gel column chromatography using 3:1 hexane:EtOAc mixture as eluent, giving the desired product in 93% yield.

2-(5-(benzyloxy)-3'-fluoro-[1,1'-biphenyl]-2-yl)ethanamine (29)

Nitrostyrene 28 (400 mg, 1.1 mmol) in freshly distilled THF (2 mL) was added dropwise to a solution of $LiAlH_4$ (87 mg, 2.2 mmol), at 0° C. under an argon atmosphere. Upon completion of the reaction (from TLC) the reaction was quenched by addition of water (45 µL), 3M NaOH (45 µL), and an additional 80 µL water, and 20 mL EtOAc. The resulting mixture was stirred at room temperature for 1 h, filtered through a plug of celite, washed with EtOAc, dried ($Na_2SO_4$) and concentrated to a crude brown mixture, which was purified by column chromatography (Silica gel, 10% MeOH in DCM) to give the desired product.

N-(2-(5-(benzyloxy)-3'-fluoro-[1,1'-biphenyl]-2-yl)ethyl)acetamide (30)

80 mg, 0.25 mmol of 29 was added to a 25 mL oven-dried flask containing 5 mL freshly distilled DCM, under argon atmosphere. Acetic anhydride (21 µL, 0.22 mmol) and triethyl amine (35 µL) were then added to the solution and the resultant mixture stirred at room temperature for 3 h. The reaction mixture was then quenched by addition of saturated ammonium chloride, and extracted into DCM. The combined organic layers were dried ($Na_2SO_4$) and concentrated to a crude mixture, which was purified by column chromatography (Silica gel, 3:1 hexane:EtOAc) to give the desired product.

N-(2-(3'-fluoro-5-hydroxy-[1,1'-biphenyl]-2-yl)ethyl)acetamide (23)

400 mg of 10 was added to a 10 mL round bottom flask containing methanol, and 10 mol % $Pd(OH)_2$ was added to the flask. This was subjected to degassing using a hydrogen balloon attached, for 10 min, and then left stirring at room temperature under a hydrogen atmosphere for 8 h. The reaction was filtered, and concentrated to give pure product 23 that was used without further purification.

Example 20

Synthesis of carbocyclic analogues N-(2-(5-((4-(benzyloxy)cyclohex-2-en-1-yl)oxy)-3'-fluoro-[1,1'-biphenyl]-2yl)ethyl)acetamide (36), and N-(2-(5-((4-(benzyloxy)-2,3-dihydroxycyclohexyl)oxy)-3'-fluoro-[1,1'-biphenyl]-2yl)ethyl)acetamide (37)

1,2-di(oxiran-2-yl)ethane (32)

To a solution of 1,5-hexadiene (5 g, 0.12 mol) in freshly distilled DCM (100 mL) at 0° C. was added mCPBA. (12.5 g, 0.146 mol, 70% by wt.) The suspension was stirred at room temperature for 2h. The reaction was washed with saturated $NaHCO_3$ solution, (4×80 mL) followed by brine. (100 mL) The organic layers were then dried ($Na_2SO_4$) and concentrated. The residue was purified by flash column chromatography using 5-20% EtOAc/hex as eluent, to give the desired product in 65% yield.

1,6-Heptadiene-3,5-diol (33)

To a stirred solution of tri-methylsulfonium iodide (6.12 g, 30 mmol) in dry THF (50 mL) at −10° C. was added dropwise butyllithium (14 mL, 2.5 M in hexane). The reaction mixture was stirred at −10° C. for 30 min, and a solution of diepoxide 32 (570 mg, 5 mmol) in dry THF (5 mL) was added. The reaction mixture was allowed to warm to room temperature, and the white suspension was stirred overnight. The mixture was treated with a saturated aqueous $NH_4Cl$ solution (15 mL), extracted with $CH_2Cl_2$ (3×10 mL), dried over $Na_2SO_4$, and concentrated. The crude product was purified on silica gel (pentane/ether 50/50) to yield the compound 33 (360 mg, 45% yield)

cyclohex-2-ene-1,4-diol (34)

To a stirred solution of 33 (190 mg, 1.3 mmol) in DCM (0.1M) was added Grubbs Catalyst, 2nd Generation. (22 mg, 0.026 mmol) The reaction mixture was heated to reflux for 2 h and was then concentrated under vacuum. The crude product was purified by column chromatography on silica gel with 50-100% EtOAc/hex to yield the desired compound.

4-(benzyloxy)cyclohex-2-en-1-ol (35)

To a solution of 34 (79 mg, 0.69 mmol) in DMF (1 mL) was added sodium hydride (14 mg, 0.62 mmol) at 0° C. Benzyl bromide (73 µL, 0.62 mmol) was added to the mixture dropwise, under an argon atmosphere. The reaction was stirred for 16 h at room temperature. Upon completion, distilled water (3 mL) was added to the mixture and the organic layer extracted into ethyl acetate. The organic layers were combined, dried and concentrated to give a crude mixture that was purified by column chromatography (Silica gel, 10%-20% EtOAc in hexane) to give 35 as an oil.

N-(2-(5-((4-(benzyloxy)cyclohex-2-en-1-yl)oxy)-3'-fluoro-[1,1'-biphenyl]-2yl)ethyl)acetamide (36)

To a solution of 35 (70 mg, 0.34 mmol) in freshly distilled THF (3 mL) at 0° C. was added triphenyl phosphine (180 mg, 0.68 mmol) and 23 (90 mg, 0.34 mmol). DIAD (0.135 mL, 0.68 mmol) was added to the mixture dropwise. The reaction was warmed to room temperature and stirred for 4 h. The reaction mixture was treated with saturated aqueous $NaHCO_3$ solution (2 mL), washed with water, followed by brine, dried over $Na_2SO_4$, and concentrated to give a crude mixture that was purified by column chromatography (30% 50% EtOAc in hexane) to give 36 as an oil.

N-(2-(5-((4-(benzyloxy)-2,3-dihydroxycyclohexyl)oxy)-3'-fluoro-[1,1'-biphenyl]-2yl)ethyl)acetamide (37)

To a solution of 36 (15 mg, 0.032 mmol) in a mixture of $THF/H_2O$, (1:1, 1 mL) was added catalytic amount of $OsO_4$ (0.0032 mmol) and NMO. (5.7 mg, 0.048 mmol) The resulting solution was stirred at room temperature overnight. THF was evaporated and the residue extracted with EtOAc. The organic layer was washed with saturated $NaHCO_3$ followed by saturated NH$_4$Cl, dried, (Na$_2$SO$_4$) concentrated and purified (50%-100% EtOAc in hexane) to give 37.

Example 21

Synthesis of carbocyclic analogue N-(2-(5-((4-(tert-butyl)cyclohexyl)oxy)-3'-fluoro-[1,1'-biphenyl]-2-yl)ethyl) acetamide (39)

4-(tert-butyl)cyclohexyl 4-methylbenzenesulfonate (38)

4-(tert-butyl)cyclohexan-1-ol (500 mg, 3 mmol) was dissolved in pyridine (50 mL) and stirred at room temperature for 30 min. Tosyl chloride (915 mg, 4.79 mmol) was added to the reaction mixture and allowed to stir overnight. The reaction was quenched by addition of water (50 mL) and extracted with ether. (3×20 mL) washed with saturated CuSO$_4$, water, saturated aqueous NaHCO$_3$, water, and dried, (Na$_2$SO$_4$) concentrated and purified (10% EtOAc in hexane) to give 38 as a white solid.

N-(2-(5-((4-(tert-butyl)cyclohexyl)oxy)-3'-fluoro-[1,1'-biphenyl]-2-yl)ethyl) acetamide (39)

To a solution of 38 (50 mg, 0.16 mmol) in anhydrous DMF (2 mL) was added K$_2$CO$_3$, (24 mg) 38 (44 mg, 0.16 mmol) and TBAI (6 mg). The solution mixture was heated to 80° C. for 4 days. Upon completion, distilled water (4 mL) was added to the mixture and the organic layer extracted into ethyl acetate. After removal of the solvent on a rotor evaporator, the crude mixture was purified by column chromatography (50% EtOAc in hexane) to give 39.

From the foregoing it will be seen that this invention is one well adapted to attain all ends and objectives herein-above set forth, together with the other advantages which are obvious and which are inherent to the invention. Since many possible embodiments may be made of the invention without departing from the scope thereof, it is to be understood that all matters herein set forth or shown in the accompanying drawings are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

The invention claimed is:

1. A compound according to Formula I, or a pharmaceutically acceptable salt thereof:

(I)

wherein
R$_1$ is hydrogen, hydroxy, halo, trifluoroalkyl, alkyl, alkenyl, alkynyl, carbocyclic, heterocyclic, aryl, aralkyl, carboxyl, amido, amino, alkoxy, sulfanyl, sulfenyl, sulfonyl, or ether;
R$_2$ is hydrogen, halo, hydroxy, trifluoromethyl, alkoxy, alkyl, alkenyl, alkynyl, carbocyclic, alkylcarbocyclic, alkylheterocyclic, heterocyclic, or —R$^9$—O—R$^{10}$, wherein
R$^9$ is a covalent bond or alkylene, and
R$^{10}$ is hydrogen, alkyl, C-amido or acyl; or
R$_2$ together with R$_3$ and the atoms to which they are attached form a carbocyclic ring with 5 to 7 ring members or a heterocyclic ring having 4 to 8 ring members with at least one heteroatom selected from oxygen or nitrogen;
R$_3$ is hydrogen, hydroxy, halo, trifluoroalkyl, alkyl, alkoxy, sulfanyl, or —R$^{11}$—O—R$^{12}$, wherein
R$^{11}$ is a covalent bond or alkylene, and
R$^{12}$ is alkyl, C-amido or acyl; or
R$_3$ together with R$_2$ and the atoms to which they are attached form a carbocyclic ring with 5 to 7 ring members or a heterocyclic ring having 4 to 8 ring members with at least one heteroatom selected from oxygen or nitrogen; or R$_3$ is absent when Y is =N—;
R$_4$ is hydrogen, hydroxy, alkyl, arylalkoxy, carboxyl, —R$^{13}$—O—R$^{14}$, or —R$^{13}$—R$^{15}$; and wherein
R$^{13}$ is a covalent bond or alkylene, and
R$^{14}$ is hydrogen, C-amido or acyl, and
R$^{15}$ is N-amido, —POR$^{16}$R$^{17}$, —SO$_2$R$^{18}$, or sulfonamido, and wherein
R$^{16}$, R$^{17}$, R$^{18}$ are independently alkoxy;
R$_5$ is hydrogen, hydroxy, alkyl, arylalkoxy, alkenyl, alkynyl, aryl, or aralkyl;
R$_6$ is hydrogen, hydroxy, sulfanyl, alkyl, alkenyl, alkynyl, aryl, arylalkyl, alkoxy, aryloxy, or arylalkoxy;
R$_7$ is hydrogen, hydroxyl, arylalkoxy, alkyl, or absent;
R$_8$ is hydrogen, hydroxyl, or arylalkoxy;
R$_{22}$ is hydrogen, hydroxy, amino, amido, cyano, alkoxy, halogen, trifluoroalkyl, alkyl, alkenyl, alkynyl, ester, nitro, carboxyl, aralkyl, aryl, carbocyclic, heterocyclic, trifluoromethyl, sulfonyl, sulfanyl, sulfenyl, ether, R$^{25}$—OR$^{26}$, or R$^{25}$—NHR$^{26}$; wherein
R$^{25}$ is a covalent bond or alkylene; and
R$^{26}$ is a hydrogen, alkyl, C-amido, or acyl;
R$_{23}$ is hydrogen, hydroxy, amino, amido, cyano, alkoxy, halogen, trifluoroalkyl, alkyl, alkenyl, alkynyl, ester, nitro, carboxyl, aralkyl, aryl, carbocyclic, heterocyclic, trifluoromethyl, sulfonyl, sulfanyl, sulfenyl, ether, R$^{27}$—OR$^{28}$, or R$^{27}$—NHR$^{28}$; wherein
R$^{27}$ is a covalent bond or alkylene and
R$^{28}$ is a hydrogen, alkyl, C-amido, or acyl; or
R$_{24}$ is hydrogen, hydroxy, amino, amido, cyano, alkoxy, halogen, trifluoroalkyl, alkyl, alkenyl, alkynyl, ester, nitro, carboxyl, aralkyl, aryl, carbocyclic, heterocyclic, trifluoromethyl, sulfonyl, sulfanyl, sulfenyl, ether, R$^{29}$—OR$^{30}$, or R$^{29}$—NHR$^{30}$, wherein
R$^{29}$ is a covalent bond or alkylene and
R$^{30}$ is a hydrogen, alkyl, C-amido, or acyl; or
X$_1$ is —CHR$^{19}$— or =CR$^{19}$=, and wherein R$^{19}$ is selected from hydrogen, halo, alkyl, alkenyl, or alkynyl; or X$_1$ together with X$_2$ form a carbocyclic ring having 3 to 7 ring members; or wherein X$_1$-X$_2$ is —C≡C—;
X$_2$ is —CHR$^{20}$— or =CR$^{20}$—, and wherein R$^{20}$ is selected from hydrogen, halo, alkyl, alkenyl, or alkynyl; or X$_2$ together with X$_1$ form a carbocyclic ring having 3 to 7 ring members; or wherein X$_1$-X$_2$ is —C≡C—;

$X_3$ is O or $CH_2$;
X is $=CR^{21}-$ or $=N-$, wherein
$R^{21}$ is hydrogen, halo, trifluoromethyl, alkyl, alkenyl, alkynyl, alkoxy, or hydroxy;
R' is H or alkyl;
R" is alkyl, alkoxy, haloalkyl, alkylcycloalkyl or alkylamidoalkyl;
Y is $=CR_3-$ or $=N-$;
Z is CH, or Z-$Z_1$ is $-C=C-$;
$Z_1$ is CH, O, or Z-$Z_1$ is $-C=C-$; and
n is 0, 1, 2, or 3.

2. The compound according to claim 1 wherein
$X_1$ is $-CHR^{19}-$ and
$R^{19}$ is hydrogen or alkyl; or
$X_1$ together with $X_2$ form a carbocyclic ring having 3 to 7 ring members; and
$X_2$ is $-CHR^{20}-$ and wherein
$R^{20}$ is hydrogen or alkyl; or
$X_2$ together with $X_1$ form a carbocyclic ring having 3 to 7 ring members.

3. The compound according to claim 1 wherein
R' is H,
R" is $CH_3$,
$X_1$ is $CH_2$, and
$X_2$ is $CH_2$.

4. The compound according to claim 1 wherein $R_4$ and $R_5$ are independently methyl or hydrogen.

5. The compound according to claim 1 wherein $R_6$ is selected from hydrogen, hydroxy, methoxy, sulfanyl, or alkyl.

6. The compound according to claim 1 wherein $R_7$ and $R_8$ are hydroxy.

7. The compound of claim 1 further defined by formula (II):

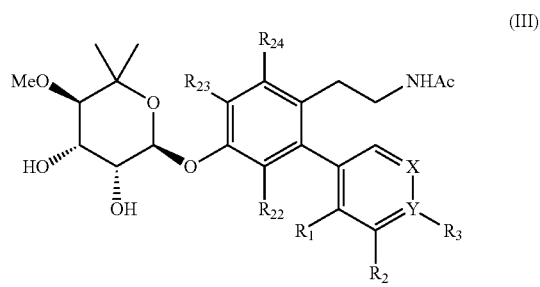

(II)

wherein
$R_1$ is hydrogen, halo, hydroxy, trifluoroalkyl, alkoxy, or sulfanyl;
$R_2$ is hydrogen, halo, hydroxy, trifluoromethyl, alkoxy, or alkyl, or $R_2$ together with $R_3$ and the atoms to which they are attached form a carbocyclic ring with 5 to 7 ring members or a heterocyclic ring having 4 to 8 ring members with at least one heteroatom selected from oxygen or nitrogen;
$R_3$ is hydrogen, halo, hydroxy, trifluoroalkyl, alkoxy, sulfanyl, alkyl; or $R_3$ together with $R_2$ and the atoms to which they are attached form a carbocyclic ring with 5 to 7 ring members or a heterocyclic ring having 4 to 8 ring members with at least one heteroatom selected from oxygen or nitrogen, or $R_3$ is absent when Y is $=N-$;
X is $=CR^{21}-$ or $=N-$, wherein $R^{21}$ is hydrogen, halo, or trifluoromethyl; and
Y is $=CR_3-$ or $=N-$;
or a pharmaceutically acceptable salt thereof.

8. The compound of claim 7 wherein
$R_1$ is hydrogen, halo, alkoxy, or sulfanyl;
$R_2$ is hydrogen, hydroxy, halo, trifluoromethyl, or alkoxy;
$R_3$ is hydrogen, hydroxy, halo, trifluoroalkyl, alkoxy, or sulfanyl;
X is $=CR^{21}-$, wherein $R^{21}$ is hydrogen, halo, or trifluoromethyl; and
Y is $=CR_3-$;
or a pharmaceutically acceptable salt thereof.

9. The compound of claim 1 further defined by formula (III):

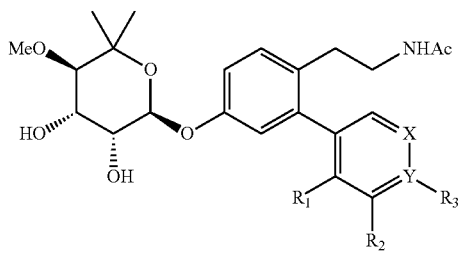

(III)

wherein one of $R_{22}$, $R_{23}$, and $R_{24}$ is not H;
or a pharmaceutically acceptable salt thereof.

10. The compound of claim 1 selected from the group consisting of
N-(2-(5-(((3R,4S,5R)-3,4-dihydroxy-5-methoxy-6,6-dimethyltetrahydro-2H-pyran-2-yl)oxy)-[1,1'-biphenyl]-2-yl)ethyl)acetamide (11a);
N-(2-(5-(((3R,4S,5R)-3,4-dihydroxy-5-methoxy-6,6-dimethyltetrahydro-2H-pyran-2-yl)oxy)-3'-fluoro-[1,1'-biphenyl]-2-yl)ethyl)acetamide (11b);
N-(2-(5-(((3R,4S,5R)-3,4-dihydroxy-5-methoxy-6,6-dimethyltetrahydro-2H-pyran-2-yl)oxy)-4'-fluoro-[1,1'-biphenyl]-2-yl)ethyl)acetamide (11c);
N-(2-(2'-chloro-5-(((3R,4S,5R)-3,4-dihydroxy-5-methoxy-6,6-dimethyltetrahydro-2H-pyran-2-yl)oxy)-[1,1'-biphenyl]-2-yl)ethyl)acetamide (11d);
N-(2-(3'-chloro-5-(((3R,4S,5R)-3,4-dihydroxy-5-methoxy-6,6-dimethyltetrahydro-2H-pyran-2-yl)oxy)-[1,1'-biphenyl]-2-yl)ethyl)acetamide (11e);
N-(2-(5-(((3R,4S,5R)-3,4-dihydroxy-5-methoxy-6,6-dimethyltetrahydro-2H-pyran-2-yl)oxy)-3'-(trifluoromethyl)-[1,1'-biphenyl]-2-yl)ethyl)acetamide (11f);
N-(2-(5-(((3R,4S,5R)-3,4-dihydroxy-5-methoxy-6,6-dimethyltetrahydro-2H-pyran-2-yl)oxy)-4'-(trifluoromethyl)-[1,1'-biphenyl]-2-yl)ethyl)acetamide (11g);
N-(2-(5-(((3R,4S,5R)-3,4-dihydroxy-5-methoxy-6,6-dimethyltetrahydro-2H-pyran-2-yl)oxy)-2'-(methylthio)-[1,1'-biphenyl]-2-yl)ethyl)acetamide (11h);
N-(2-(5-(((3R,4S,5R)-3,4-dihydroxy-5-methoxy-6,6-dimethyltetrahydro-2H-pyran-2-yl)oxy)-2'-methoxy-[1,1'-biphenyl]-2-yl)ethyl)acetamide (11i);
N-(2-(5-(((3R,4S,5R)-3,4-dihydroxy-5-methoxy-6,6-dimethyltetrahydro-2H-pyran-2-yl)oxy)-3'-methoxy-[1,1'-biphenyl]-2-yl)ethyl)acetamide (11j);
N-(2-(5-(((3R,4S,5R)-3,4-dihydroxy-5-methoxy-6,6-dimethyltetrahydro-2H-pyran-2-yl)oxy)-3'-methyl-[1,1'-biphenyl]-2-yl)ethyl)acetamide (11k);
N-(2-(5-(((3R,4S,5R)-3,4-dihydroxy-5-methoxy-6,6-dimethyltetrahydro-2H-pyran-2-yl)oxy)-3'-(morpholinomethyl)-[1,1'-biphenyl]-2-yl)ethyl)acetamide (11l);

N-(2-(5-(((3R,4S,5R)-3,4-dihydroxy-5-methoxy-6,6-dimethyltetrahydro-2H-pyran-2-yl)oxy)-4'-hydroxy-[1,1'-biphenyl]-2-yl)ethyl)acetamide (11m);

N-(2-(benzo[d][1,3]dioxol-5-yl)-4-(((3R,4S,5R)-3,4-dihydroxy-5-methoxy-6,6-dimethyltetrahydro-2H-pyran-2-yl)oxy)phenethyl)acetamide (11n);

N-(4-(((3R,4S,5R)-3,4-dihydroxy-5-methoxy-6,6-dimethyltetrahydro-2H-pyran-2-yl)oxy)-2-(pyridin-3-yl)phenethyl)acetamide (11o);

N-(4-(((3R,4S,5R)-3,4-dihydroxy-5-methoxy-6,6-dimethyltetrahydro-2H-pyran-2-yl)oxy)-2-(pyridin-4-yl)phenethyl)acetamide (11p);

N-(4'-(((3R,4S,5R)-3,4-dihydroxy-5-methoxy-6,6-dimethyltetrahydro-2H-pyran-2-yl)oxy)-3''-fluoro-1,2,3,6-tetrahydro-[1,1':2',1''-terphenyl]-2-yl)acetamide (20a);

N-(4'-(((3R,4S,5R)-3,4-dihydroxy-5-methoxy-6,6-dimethyltetrahydro-2H-pyran-2-yl)oxy)-3''-(trifluoromethyl)-1,2,3,6-tetrahydro-[1,1':2',1''-terphenyl]-2-yl)acetamide (20b);

N-(2-(5-((4-(benzyloxy)cyclohexyl)oxy)-3'-fluoro-[1,1'-biphenyl]-2-yl)ethyl)acetamide (24);

N-(2-(5-((4-(benzyloxy)cyclohex-2-en-1-yl)oxy)-3'-fluoro-[1,1'-biphenyl]-2-yl)ethyl)acetamide (36);

N-(2-(5-((4-(benzyloxy)-2,3-dihydroxycyclohexyl)oxy)-3'-fluoro-[1,1'-biphenyl]-2-yl)ethyl)acetamide (37);

N-(2-(5-((4-(tert-butyl)cyclohexyl)oxy)-3'-fluoro-[1,1'-biphenyl]-2-yl)ethyl)acetamide (39);

N-(2-(3'-fluoro-5-((4-(piperidin-4-yl)cyclohexyl)oxy)-[1,1'-biphenyl]-2-yl)ethyl)acetamide (40);

N-(2-(5-(((3R,4S,5R)-3,4-dihydroxy-5-methoxy-6,6-dimethyltetrahydro-2H-pyran-2-yl)oxy)-3'-fluoro-6-hydroxy-[1,1'-biphenyl]-2-yl)ethyl)acetamide (41);

N-(2-(5-(((3R,4S,5R)-3,4-dihydroxy-5-methoxy-6,6-dimethyltetrahydro-2H-pyran-2-yl)oxy)-3'-fluoro-3-methoxy-[1,1'-biphenyl]-2-yl)ethyl)acetamide (42); and N-(2-(5-(((3R,4S,5R)-3,4-dihydroxy-5-methoxy-6,6-dimethyltetrahydro-2H-pyran-2-yl)oxy)-3'-fluoro-4-methyl-[1,1'-biphenyl]-2-yl)ethyl)acetamide (43);

or a pharmaceutically salt thereof.

11. The compound claim 10 which is
N-(2-(5-(((3R,4S,5R)-3,4-dihydroxy-5-methoxy-6,6-dimethyltetrahydro-2H-pyran-2-yl)oxy)-3'-fluoro-[1,1'-biphenyl]-2-yl)ethyl)acetamide (11b);

N-(2-(5-(((3R,4S,5R)-3,4-dihydroxy-5-methoxy-6,6-dimethyltetrahydro-2H-pyran-2-yl)oxy)-4'-fluoro-[1,1'-biphenyl]-2-yl)ethyl)acetamide (11c);

N-(2-(2'-chloro-5-(((3R,4S,5R)-3,4-dihydroxy-5-methoxy-6,6-dimethyltetrahydro-2H-pyran-2-yl)oxy)-[1,1'-biphenyl]-2-yl)ethyl)acetamide (11d);

N-(2-(3'-chloro-5-(((3R,4S,5R)-3,4-dihydroxy-5-methoxy-6,6-dimethyltetrahydro-2H-pyran-2-yl)oxy)-[1,1'-biphenyl]-2-yl)ethyl)acetamide (11e);

N-(2-(5-(((3R,4S,5R)-3,4-dihydroxy-5-methoxy-6,6-dimethyltetrahydro-2H-pyran-2-yl)oxy)-3'-(trifluoromethyl)-[1,1'-biphenyl]-2-yl)ethyl)acetamide (11f); or N-(2-(5-(((3R,4S,5R)-3,4-dihydroxy-5-methoxy-6,6-dimethyltetrahydro-2H-pyran-2-yl)oxy)-4'-(trifluoromethyl)-[1,1'-biphenyl]-2-yl)ethyl)acetamide (11g);

or a pharmaceutically salt thereof.

12. The compound of claim 11 which is
N-(2-(5-(((3R,4S,5R)-3,4-dihydroxy-5-methoxy-6,6-dimethyltetrahydro-2H-pyran-2-yl)oxy)-3'-fluoro-[1,1'-biphenyl]-2-yl)ethyl)acetamide (11b);

N-(2-(3'-chloro-5-(((3R,4S,5R)-3,4-dihydroxy-5-methoxy-6,6-dimethyltetrahydro-2H-pyran-2-yl)oxy)-[1,1'-biphenyl]-2-yl)ethyl)acetamide (11e); or N-(2-(5-(((3R,4S,5R)-3,4-dihydroxy-5-methoxy-6,6-dimethyltetrahydro-2H-pyran-2-yl)oxy)-3'-(trifluoromethyl)-[1,1'-biphenyl]-2-yl)ethyl)acetamide (11f);

or a pharmaceutically salt thereof.

13. A pharmaceutical composition comprising a therapeutically effective amount of a compound or pharmaceutically acceptable salt of claim 1 and a pharmaceutically acceptable carrier.

14. A method for treating or preventing diabetic peripheral neuropathy in a subject in need thereof comprising administering to the subject a therapeutically effective amount of a compound or pharmaceutically acceptable salt of claim 7.

15. The method of claim 14, wherein the compound exhibits neuroprotective effects by upregulation of Hsp70.

16. The method of claim 14, wherein the composition is administered in an amount effective to alleviate or prevent symptoms of neuronal glucotoxicity.

17. The method of claim 16, wherein the composition is administered in an amount effective to alleviate symptoms of neuronal glucotoxicity.

18. The compound of claim 1, further defined by the formula IV, or a pharmaceutically acceptable salt thereof:

(IV)

wherein
$R_1$ is hydrogen, hydroxy, halo, trifluoroalkyl, alkyl, alkenyl, alkynyl, carbocyclic, heterocyclic, aryl, aralkyl, carboxyl, amido, amino, alkoxy, trifluoromethyl, sulfanyl, sulfenyl, sulfonyl, or ether;

$R_2$ is hydrogen, halo, hydroxy, trifluoromethyl, alkoxy, alkyl, alkenyl, alkynyl, carbocyclic, alkylcarbocyclic, alkylheterocyclic, heterocyclic, or $-R^9-O-R^{10}$, wherein
$R^9$ is a covalent bond or alkylene, and
$R^{10}$ is hydrogen, alkyl, C-amido or acyl; or
$R_2$ together with $R_3$ and the atoms to which they are attached form a carbocyclic ring with 5 to 7 ring members or a heterocyclic ring having 4 to 8 ring members with at least one heteroatom selected from oxygen or nitrogen;

$R_3$ is hydrogen, hydroxy, halo, trifluoroalkyl, alkyl, alkoxy, sulfanyl, or $-R^{11}-O-R^{12}$, wherein
$R^{11}$ is a covalent bond or alkylene, and
$R^{12}$ is alkyl, C-amido or acyl; or
$R_3$ together with $R_2$ and the atoms to which they are attached form a carbocyclic ring with 5 to 7 ring members or a heterocyclic ring having 4 to 8 ring members with at least one heteroatom selected from oxygen or nitrogen; or $R_3$ is absent when Y is =N—;

$R_4$ is hydrogen, hydroxy, alkyl, arylalkoxy, carboxyl, $-R^{13}-O-R^{14}$, or $-R^{13}-R^{15}$; and wherein R¹³ is a covalent bond or alkylene, and R¹⁴ is hydrogen, C-amido or acyl, and R¹⁵ is N-amido, —POR¹⁶R¹⁷, —SO₂R¹⁸, or sulfonamido, and wherein R¹⁶, R¹⁷, R¹⁸ are independently alkoxy;

$R_5$ is hydrogen, hydroxy, alkyl, alkenyl, alkynyl, aryl, or aralkyl;

$R_6$ is hydrogen, hydroxy, sulfanyl, alkyl, alkenyl, alkynyl, aryl, arylalkyl, alkoxy, aryloxy, or arylalkoxy;

$R_7$ is hydrogen or hydroxyl;

$R_8$ is hydrogen or hydroxyl;

$X_1$ is —CHR¹⁹— or —CR¹⁹=, and wherein

R¹⁹ is selected from hydrogen, halo, alkyl, alkenyl, or alkynyl; or $X_1$ together with $X_2$ form a carbocyclic ring having 3 to 7 ring members; or wherein $X_1$-$X_2$ is —C≡C—;

$X_2$ is —CHR²⁰— or =CR²⁰—, and wherein

R²⁰ is selected from hydrogen, halo, alkyl, alkenyl, or alkynyl; or $X_2$ together with $X_1$ form a carbocyclic ring having 3 to 7 ring members; or wherein $X_1$-$X_2$ is —C≡C—;

X is =CR²¹— or =N—, wherein

R²¹ is hydrogen, halo, trifluoromethyl, alkyl, alkenyl, alkynyl, alkoxy, or hydroxy;

R' is H or alkyl;

R" is alkyl, alkoxy, haloalkyl, alkylcycloalkyl or alkylamidoalkyl;

Y is =CR₃— or =N—; and n is 0, 1, 2, or 3.

19. The compound of claim 12 wherein the compound is:

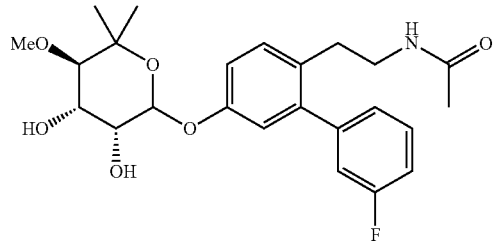 [SMILES: CO[C@@H]1[C@@H](O)[C@@H](O)C(Oc2ccc(CCNC(C)=O)c(-c3cccc(F)c3)c2)OC1(C)C]

or a pharmaceutically acceptable salt thereof.

* * * * *